(12) United States Patent
Dominguez et al.

(10) Patent No.: US 11,851,446 B2
(45) Date of Patent: *Dec. 26, 2023

(54) PROBES FOR IMAGING HUNTINGTIN PROTEIN

(71) Applicant: CHDI Foundation, Inc., New York, NY (US)

(72) Inventors: Celia Dominguez, Los Angeles, CA (US); John Wityak, Carlsbad, CA (US); Jonathan Bard, New York, NY (US); Alex Kiselyov, New York, NY (US); Christopher John Brown, Abingdon (GB); Michael Edward Prime, Abingdon (GB); Peter David Johnson, Oxfordshire (GB); Daniel Clark-Frew, Wantage (GB)

(73) Assignee: CHDI Foundation, Inc., New York, NY (US)

( * ) Notice: Subject to any disclaimer, the term of this patent is extended or adjusted under 35 U.S.C. 154(b) by 89 days.

This patent is subject to a terminal disclaimer.

(21) Appl. No.: 17/353,627

(22) Filed: Jun. 21, 2021

(65) Prior Publication Data
US 2021/0380608 A1 Dec. 9, 2021

Related U.S. Application Data

(63) Continuation of application No. 15/507,203, filed as application No. PCT/US2015/047401 on Aug. 28, 2015, now Pat. No. 11,104,691.

(60) Provisional application No. 62/043,590, filed on Aug. 29, 2014.

(51) Int. Cl.
C07D 519/00 (2006.01)
C07D 471/04 (2006.01)
A61K 51/04 (2006.01)

(52) U.S. Cl.
CPC ........ C07D 519/00 (2013.01); A61K 51/0455 (2013.01); A61K 51/0459 (2013.01); C07D 471/04 (2013.01)

(58) Field of Classification Search
CPC .............. C07D 519/00; C07D 471/04; A61K 51/0455; A61K 51/0459
USPC ..................................................... 424/1.89
See application file for complete search history.

(56) References Cited

U.S. PATENT DOCUMENTS

| | | |
|---|---|---|
| 10,137,211 B2 | 11/2018 | Dominguez et al. |
| 10,479,802 B2 | 11/2019 | Dominguez et al. |
| 10,765,764 B2 | 9/2020 | Dominguez et al. |
| 10,907,197 B2 | 2/2021 | Dominguez et al. |
| 11,059,836 B2 | 7/2021 | Dominguez et al. |
| 11,071,793 B2 | 7/2021 | Dominguez et al. |
| 11,104,691 B2 | 8/2021 | Dominguez et al. |
| 11,344,637 B2 | 5/2022 | Dominguez et al. |
| 2004/0023972 A1 | 2/2004 | Sundermann et al. |
| 2010/0173930 A1 | 7/2010 | Muci et al. |
| 2010/0216994 A1 | 8/2010 | Tanifuji et al. |
| 2011/0065727 A1 | 3/2011 | De Peretti et al. |
| 2011/0171739 A1 | 7/2011 | Kemp et al. |
| 2012/0083474 A1 | 4/2012 | Berthelot et al. |
| 2017/0056535 A1 | 3/2017 | Dominguez et al. |
| 2017/0281804 A1 | 10/2017 | Dominguez et al. |
| 2017/0283436 A1 | 10/2017 | Dominguez et al. |
| 2017/0283439 A1 | 10/2017 | Dominguez et al. |
| 2017/0292150 A1 | 10/2017 | Dominguez et al. |
| 2019/0167821 A1 | 6/2019 | Dominguez et al. |
| 2020/0102328 A1 | 4/2020 | Dominguez et al. |
| 2021/0060187 A1 | 3/2021 | Dominguez et al. |
| 2021/0379211 A1 | 12/2021 | Dominguez et al. |

FOREIGN PATENT DOCUMENTS

| | | | |
|---|---|---|---|
| EP | 1326613 | 6/2004 | |
| EP | 2216052 | 8/2010 | |
| JP | 2013-237655 | 11/2013 | |
| WO | WO 2008/091195 | 7/2008 | |
| WO | WO-2010011964 A2 * | 1/2010 | ......... A61K 51/0406 |
| WO | WO 2014/076021 | 5/2014 | |
| WO | WO 2014/139882 | 9/2014 | |
| WO | WO 2015/044095 | 4/2015 | |

OTHER PUBLICATIONS

Bergstrom et al. Positron emission tomography microdosing: a new concept with application in tracer and early clinical drug development. Eur. J. Clin. Pharmacol. 2003; 59:357-366.

Burchak, et al. Combinatorial discovery of fluorescent pharmacophores by multicomponent reactions in droplet arrays. J Am Chem Soc. Jul. 6, 2011;133(26):10058-61. doi: 10.1021/ja204016e. Epub Jun. 14, 2011.

CAS RN 1484907-42-7, STN Entry Date Dec. 2, 2013.
CAS RN 1489276-60-9, STN Entry Date Dec. 7, 2013.
CAS RN 1492736-72-7, STN Entry Date Dec. 12, 2013.
CAS RN 1493480-32-2, STN Entry Date Dec. 13, 2013.
CAS RN 1497064-29-5, STN Entry Date Dec. 18, 2013.
CAS RN 1503015-17-5, STN Entry Date Dec. 26, 2013.

(Continued)

Primary Examiner — Michael G. Hartley
Assistant Examiner — Sean R Donohue
(74) Attorney, Agent, or Firm — Sheppard Mullin Richter & Hampton LLP

(57) ABSTRACT

Provided are imaging agents comprising a compound of Formula I, or a pharmaceutically acceptable salt thereof, and methods of their use.

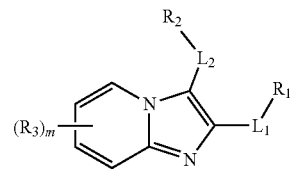

(I)

9 Claims, No Drawings

(56) References Cited

OTHER PUBLICATIONS

Extended European Search Report and Opinion dated Mar. 20, 2018 for EP Application No. 15836261.6. 9 pages.
Guchhait, et al. An efficient, regioselective, versatile synthesis of N-fused 2- and 3-aminoimidazoles via Ugi-type multicomponent reaction mediated by zirconium(IV) chloride in polyethylene glycol-400. Synlett. 2009; 4:628-632.
International Search Report & Written Opinion dated Dec. 4, 2015 for PCT/US2015/047401. 8 pages.
Patani, et al. Bioisosterism: a rational approach in drug design. Chem. Rev. 1996; 96:3147-3176.
Puttaraju et al. Iodine-catalyzed three component reaction: a novel synthesis of 2-aryl-imidazo [1, 2-a] pyridine scaffolds. RSC Adv. 2013; 3.43:20883-20890.
Yousefi et al. Development of an Improved Radioiodinated 2-Phenylimidazo[1,2-a]Pyridine for Non-Invasive Imaging of Amyloid Plaques. Med. Chem. Commun. 2012, 3, 775-779.
Zhang, et al. Synthesis and evaluation of two positron-labeled nitric oxide synthase inhibitors, S-[11C]methylisothiourea and S-(2-[18F]fluoroethyl)isothiourea, as potential positron emission tomography tracers. J. Med. Chem. Dec. 20, 1996;39(26):5110-8.
Zhuang, et al. Structure-activity relationship of imidazo[1,2-a]pyridines as ligands for detecting beta-amyloid plaques in the brain. J. Med. Chem. Jan. 16, 2003;46(2):237-43.

* cited by examiner

PROBES FOR IMAGING HUNTINGTIN PROTEIN

CROSS REFERENCE TO RELATED APPLICATIONS

This application is a continuation of U.S. application Ser. No. 15/507,203, filed Feb. 27, 2017, which is a U.S. National Stage Application under 35 U.S.C. § 371 of PCT Application No. PCT/US2015/047401, filed Aug. 28, 2015, which claims priority to U.S. Provisional Application No. 62/043,590, filed Aug. 29, 2014, which are incorporated herein by reference for all purposes.

The advent of molecular imaging approaches such as positron emission tomography (PET) and single photon emission computed tomography (SPECT) has enabled measurements of molecular and cellular mechanisms throughout the body in preclinical and clinical settings. Such measurements have widespread diagnostic utility and their use for evaluation of treatment responses and to assist drug development is expanding rapidly. The recent introduction of high-resolution molecular imaging technology is considered by many experts as a major breakthrough that will potentially lead to a revolutionary paradigm shift in health care and revolutionize clinical practice.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

Many new molecular probes labeled with positron-emitting radionuclides and associated PET imaging assays are under development to target, detect, visualize, and quantify various extracellular and intracellular molecules and processes associated with diseases such as cancer, heart disease, and neurological disorders. For instance, several types of agents have been synthesized and evaluated for imaging amyloid β (Aβ) plaques in patients with Alzheimer's disease (AD) including, arylbenzothiazoles, stilbenes, imidazopyridines, pyridylbenzothiazoles, pyridylbenzoxazoles and pyridylbenzofurans (Swahn et al., *Bioorganic & Medicinal Chemistry Letters*, 20 (2010) 1976-1980). Furthermore, styrylbenzimidazole (SBIM) derivatives have been developed as agents for imaging neurofibrillary tangles (NFT), composed of hyperphosphorylated tau protein, in patients with AD. In binding experiments using recombinant tau and amyloid $\beta_{1\text{-}42}$ ($A\beta_{1\text{-}42}$) aggregates, 4-[(E)-2-(6-iodo-1H-benzimidazol-2-yl)ethenyl]-N,N-dimethylaniline (SBIM-3) showed higher affinity for the tau aggregates than $A\beta_{1\text{-}42}$ aggregates (ratio of $K_d$ values was 2.73). In vitro autoradiography and fluorescent staining, [$^{121}$I]SBIM-3 (or SBIM-3) bound NFT in sections of AD brain tissue. In biodistribution experiments using normal mice, all [$^{125}$I] SBIM derivatives showed high initial uptake into (3.20-4.11% ID/g at 2 min after the injection) and rapid clearance from (0.12-0.33% ID/g at 60 min after the injection) the brain (Matsumura et al., *Bioorganic & Medicinal Chemistry*, 21 (2013) 3356-3362).

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. It belongs to a family of neurodegenerative diseases caused by mutations in which an expanded CAG repeat tract results in long stretches of polyglutamine (polyQ) in the encoded protein. This family also includes dentatorubral-pallidoluysian atrophy (DRPLA), spinal and bulbar muscular atrophy (SBMA) and the spinocerebellar ataxias (SCAs). Apart from their polyQ repeats, the proteins involved are unrelated, and although they are all widely expressed in the central nervous system and peripheral tissues, they lead to characteristic patterns of neurodegeneration. In HD, the selective neurodegeneration of the γ-aminobutyric acid-releasing spiny-projection neurons of the striatum is predominant, although loss of neurons in many other brain regions has also been reported. In the unaffected population, the number of CAG repeats in the $IT_{15}$ gene that encodes the HD protein huntingtin (HTT protein) varies from 6 to 35; repeats of 36 or more define an HD allele. The length of the CAG expansion is inversely correlated with age of disease onset, with cases of juvenile onset characterized by expansions of more than 60 repeats. HD has a prevalence of 5-10 cases per 100,000 worldwide, which makes it the most common inherited neurodegenerative disorder. HTT protein is a 348-kDa multidomain protein that contains a polymorphic glutamine/proline-rich domain at its amino-terminus. The longer polyQ domain seems to induce conformational changes in the protein, which causes it to form intracellular aggregates that, in most cases, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

Several clinical trials are investigating means to alleviate or reduce symptoms and slow progression in clinically diagnosed HD. Consistent with other medical conditions, treatments might be ideally initiated at or before the earliest signs of disease. There are at least two primary challenges to the design of clinical trials for pre-HD: selection of participants who are most likely to show measurable change over the course of a clinical trial, and development of outcome measures that are sensitive to interventions and can demonstrate variation over the natural history of pre-HD. In order to meet these and other challenges to preventive clinical trials, indicators of very early disease are required.

In view of the central role of the accumulation of aggregated forms of HTT protein in the pathogenesis of HD, there is a need for molecular probes that bind to such abnormalities with high sensitivity and specificity, for molecular imaging in the living subject using PET. The compounds described herein meet this and other needs.

Provided is an imaging agent comprising a compound of Formula I,

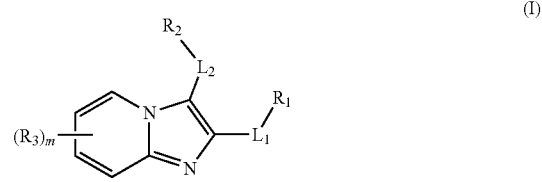

(I)

or a pharmaceutically acceptable salt thereof, wherein
$L_1$ is —CH═CH— or $L_1$ is absent;
$R_1$ is chosen from phenyl or heteroaryl, each of which is optionally substituted with one, two, or three groups independently chosen from
cyano,
halo, heteroaryl,
lower alkyl,
lower alkyl substituted with one or two substituents independently chosen from
lower alkoxy substituted with heteroaryl,
—C(O)O-lower alkyl,
hydroxyl,
lower alkynyloxy,
lower alkoxy, and
lower alkoxy substituted with one or two substituents independently chosen from
halo,
heterocycloalkyl,
heteroaryl,
heteroaryl substituted with lower alkoxy,
optionally substituted amino,
alkyl substituted with heteroaryl, and
alkyl substituted with heteroaryl substituted with lower alkoxy; or $R_1$ is phenyl substituted with two groups, which taken together with the carbon atoms to which they are bonded form a heterocycloalkenyl ring wherein said phenyl is further optionally substituted with a substituent chosen from
halo,
heteroaryl, and
optionally substituted amino;

$L_2$ is —N($R_4$)— or $L_2$ is absent;

$R_2$ is chosen from
hydrogen,
lower alkyl, and
lower alkyl substituted with lower alkoxy, amino, (alkyl)amino, (dialkyl)amino, or hydroxy;

for each occurrence, $R_3$ is independently chosen from
halo,
cyano,
lower alkoxy,
lower alkyl optionally substituted with amino, (alkyl)amino, or di(alkyl)amino, and
ethynyl optionally substituted with tri(alkyl)silyl;

$R_4$ is chosen from hydrogen and lower alkyl; and m is 0, 1, or 2, wherein the compound of Formula I, or a pharmaceutically acceptable salt thereof, is labeled with one or more positron-emitting radionuclides.

Also provided is a method of generating diagnostic images in an individual comprising administering an effective amount of an imaging agent described herein to an individual, and generating an image of at least a part of said individual.

As used in the present specification, the following words, phrases and symbols are generally intended to have the meanings as set forth below, except to the extent that the context in which they are used indicates otherwise. The following abbreviations and terms have the indicated meanings throughout:

A dash ("—") that is not between two letters or symbols is used to indicate a point of attachment for a substituent. For example, —CONH$_2$ is attached through the carbon atom.

As used herein the terms "group", "radical" or "fragment" refer to a functional group or fragment of a molecule attachable to a bond or other fragments of molecules.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

When a moiety is defined as being optionally substituted, it may be substituted as itself or as part of another moiety. For example, if $R^x$ is defined as "$C_{1-6}$ alkyl or $OC_{1-6}$ alkyl, wherein $C_{1-6}$ alkyl is optionally substituted with halogen", then both the $C_{1-6}$ alkyl group alone and the $C_{1-6}$ alkyl that makes up part of the $OC_{1-6}$ alkyl group may be substituted with halogen.

The term "alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and tert-butyl; "propyl" includes n-propyl and isopropyl. "Lower alkyl" refers to alkyl groups having 1 to 6 carbons.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 6 carbons. By "cycloalkoxy" is meant a cycloalkyl group that is likewise attached through an oxygen bridge.

"Alkynyl" refers to an unsaturated branched or straight-chain alkyl group having the indicated number of carbon atoms (e.g., 2 to 8 or 2 to 6 carbon atoms) and at least one carbon-carbon triple bond derived by the removal of two molecules of hydrogen from adjacent carbon atoms of the corresponding alkyl. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl). "Lower alkynyl" refers to alkynyl groups having 2 to 6 carbons.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl" regardless of the point of attachment (e.g., both quinolin-5- yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond derived by the removal of one molecule of hydrogen from adjacent carbon atoms of the corresponding cycloalkyl. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group.

The term "halo" includes fluoro, chloro, bromo, and iodo, and the term "halogen" includes fluorine, chlorine, bromine, and iodine.

"Haloalkyl" includes straight and branched carbon chains having the indicated number of carbon atoms (e.g., 1 to 6 carbon atoms) substituted with at least one halogen atom. In instances wherein the haloalkyl group contains more than one halogen atom, the halogens may be the same (e.g., dichloromethyl) or different (e.g., chlorofluoromethyl). Examples of haloalkyl groups include, but are not limited to, chloromethyl, dichloromethyl, trichloromethyl, fluoromethyl, difluoromethyl, trifluoromethyl, chlorofluoromethyl, 2-fluoroethyl, 2,2-difluoroethyl, 2,2,2-trifluoroethyl, 1,2-difluoroethyl, 2-chloroethyl, 2,2-dichloroethyl, 2,2,2-trichloroethyl, 1,2-dichloroethyl, pentachloroethyl, and pentafluoroethyl.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,3,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzimidazole, benzotriazole, benzofuran, benzoxazole, benzisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, cycloalkenyl, aryl, heterocycloalkyl, heterocycloalkenyl, and heteroaryl, unless otherwise expressly defined, refer respectively to alkyl, cycloalkyl, cycloalkenyl, aryl, heterocycloalkyl, heterocycloalkenyl, and heteroaryl, wherein one or more (such as up to 5, for example, up to 3) hydrogen atoms are replaced by a substituent independently chosen from:

—$R^a$, —$OR^b$, —$O(C_1$-$C_2$ alkyl)O— (e.g., methylenedioxy-), —$SR^b$, guanidine (—NHC(=NH)$NH_2$), guanidine wherein one or more of the guanidine hydrogens are replaced with a $C_1$-$C_4$alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^c$ $CONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;

$R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —N($C_1$-$C_4$ alkyl)($C_1$-$C_4$ alkylheteroaryl), —NH($C_1$-$C_4$ alkylphenyl), cyano, nitro, oxo (as substituent for heteroaryl), —$CO_2H$, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH (phenyl), —$NHSO_2$($C_1$-$C_4$ alkyl), —$NHSO_2$(phenyl), and —$NHSO_2$($C_1$-$C_4$ haloalkyl)

The term "substituted amino" refers to the group —NHR$^d$ or —NR$^d$R$^d$ where each R$^d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—R$^a$, —OR$^b$, —O($C_1$-$C_2$ alkyl)O— (e.g., methylenedioxy-), —SR$^b$, guanidine, guanidine wherein one or more of the guanidine hydrogens are replaced with a lower-alkyl group, —NR$^b$R$^c$, halo, cyano, nitro, —COR$^b$, —$CO_2$R$^b$, —CONR$^b$R$^c$, —OCOR$^b$, —OCO$_2$R$^a$, —OCONR$^b$R$^c$, —NR$^c$COR$^b$, —NR$^c$CO$_2$R$^a$, —NR$^c$CONR$^b$R$^c$, —$CO_2$R$^b$, —CONR$^b$R$^a$, —NR$^c$COR$^b$, —SOR$^a$, —$SO_2$R$^a$, —$SO_2$NR$^b$R$^c$, and —NR$^c$$SO_2$R$^a$, where R$^a$ is chosen from optionally substituted $C_1$-$C_6$ alkyl, optionally substituted aryl, and optionally substituted heteroaryl;

R$^b$ is chosen from H, optionally substituted $C_1$-$C_6$ alkyl, optionally substituted aryl, and optionally substituted heteroaryl; and R$^c$ is chosen from hydrogen and optionally substituted $C_1$-$C_4$ alkyl;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —O$C_1$-$C_4$ alkylheteroaryl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —N($C_1$-$C_4$ alkyl) ($C_1$-$C_4$ alkylheteroaryl), —NH($C_1$-$C_4$ alkylphenyl), cyano, nitro, oxo (as a substituent for heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH (phenyl), —$NHSO_2$($C_1$-$C_4$ alkyl), —$NHSO_2$(phenyl), and —$NHSO_2$($C_1$-$C_4$ haloalkyl).

The term "substituted amino" also refers to the group —NR$^c$R$^f$ wherein R$^c$ and R$^f$, together with the nitrogen to which they are bound, form an optionally substituted 5- to 7-membered nitrogen-containing, non-aromatic, heterocycle which optionally contains 1 or 2 additional heteroatoms chosen from nitrogen, oxygen, and sulfur.

"Aminocarbonyl" encompasses a group of the formula —(C=O)(optionally substituted amino) wherein substituted amino is as described herein.

Compounds described herein include, but are not limited to, their optical isomers, racemates, and other mixtures thereof. In those situations, the single enantiomers or diastereoisomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. The term "isomers" refers to different compounds that have the same molecular formula. The term "stereoisomers" refers to isomers that differ only in the way the atoms are arranged in space. The term "enantiomers" refers to stereoisomers that are non-superimposable mirror images of each other. A 1:1 mixture of a pair of enantiomers is a "racemic" mixture. The symbol "(±)" may be used to designate a racemic mixture where appropriate. The term "diastereoisomers" refers to stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line.

Where compounds described herein exist in various tautomeric forms, the term "compound" includes all tautomeric forms of the compound. Such compounds also include crystal forms including polymorphs and clathrates. Similarly, the term "salt" includes all tautomeric forms and crystal forms of the compound. The term "tautomers" refers to structurally distinct isomers that interconvert by tautomerization.

Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Pharmaceutically acceptable forms of the compounds recited herein include pharmaceutically acceptable salts, and mixtures thereof. In some embodiments, the compounds described herein are in the form of pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, haloalkanoate such as trifluoroacetate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The term "administering", as used herein in conjunction with a diagnostic agent, such as, for example, a positron-emitter labeled compound described herein, means administering directly into or onto a target tissue or to administer the diagnostic agent systemically to a patient whereby the diagnostic agent is used to image the tissue or a pathology associated with the tissue to which it is targeted. "Administering" a composition may be accomplished by injection, infusion, or by either method in combination with other known techniques.

The term "Curie" (Ci) is a unit of measurement of radioactivity. One Ci refers to that amount of any radioactive material that will decay at a rate of $3.7 \times 10^{10}$ disintegrations per second. The term "milliCurie" (mCi) refers to 10-3 Curie. It is understood that the International System (SI) unit of radioactivity, the Becquerel, is equal to one disintegration/second. Thus one Becquerel=$2.7 \times 10^{-11}$ Curie.

The term "diagnostic imaging", as used herein, refers to the use of electromagnetic radiation to produce images of internal structures of the human or animal body for the purpose of diagnosis.

The term "effective amount" of a compound, as used herein, is a predetermined amount calculated to achieve a desired effect such as an amount sufficient to enable the acquisition of a desired image of the target organ of an individual. In some instances the target organ is the brain.

The term "huntingtin protein" or "HTT protein", as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "HTT protein aggregate", as used herein refers to an insoluble fibrous amyloid comprising mis-folded HTT protein molecules.

The term "β-amyloid aggregate", as used herein refers to an insoluble fibrous amyloid comprising mis-folded β-amyloid protein molecules.

The term "imaging agent", as used herein, refers to a compound as described herein labeled with one or more positron-emitting isotopes or radionuclides. A positron-emitter labeled compound need only be enriched with a detectable isotope to a degree that permits detection with a technique suitable for the particular application.

The term "pathologic process", as used herein, refers to an altered endogenous biological process that may be associated with the aberrant production and/or functioning of proteins, peptides, RNA and other substances associated with such biological process.

The term "PET imaging", as used herein, refers to the use of a positron-emitter labeled compound to produce images of internal structures of the human or animal body.

The term "pharmaceutical composition" refers to a composition comprising at least one imaging agent described herein, whereby the composition is amenable to investigation for a specified, efficacious outcome in a mammal (for example, without limitation, a human). Those of ordinary skill in the art will understand and appreciate the techniques appropriate for determining whether a composition has a desired efficacious outcome based upon the needs of the artisan.

The term "positron-emitting radionuclide", as used herein, refers to a radioactive isotope that exhibits a particular type of radioactive decay referred to as β+ decay, in which a proton inside a radionuclide nucleus is converted into a neutron while releasing a positron and an electron neutrino ($v_e$). Some examples of positron-emitting radionuclides include $^{15}O$, $^{13}N$, $^{11}C$, $^{18}F$, $^{76}Br$, and $^{124}I$. These radionuclides have half-lives of about 2, 10, 20, 110 minutes, 16 hours, and 4.2 days respectively.

The term "tomography", as used herein, refers to a process of imaging by sections. The images may be looked at individually, as a series of two-dimensional slices or together, as a computer-generated three-dimensional representation.

Provided is an imaging agent comprising a compound of Formula I, (I)

[chemical structure]

or a pharmaceutically acceptable salt thereof, wherein
$L_1$ is —CH=CH— or $L_1$ is absent;
$R_1$ is chosen from phenyl or heteroaryl, each of which is optionally substituted with one, two, or three groups independently chosen from
  cyano,
  halo,
  heteroaryl,
  lower alkyl,
  lower alkyl substituted with one or two substituents independently chosen from
    lower alkoxy substituted with heteroaryl,
    —C(O)O-lower alkyl,
    hydroxyl,
    lower alkynyloxy,
    lower alkoxy, and
    lower alkoxy substituted with one or two substituents independently chosen from
      halo,
      heterocycloalkyl,
      heteroaryl,
      heteroaryl substituted with lower alkoxy,
      optionally substituted amino,
      alkyl substituted with heteroaryl, and
      alkyl substituted with heteroaryl substituted with lower alkoxy; or
$R_1$ is phenyl substituted with two groups, which taken together with the carbon atoms, to which they are bonded form a heterocycloalkenyl ring wherein said phenyl is further optionally substituted with a substituent chosen from
  halo,
  heteroaryl, and
  optionally substituted amino;
$L_2$ is —N($R_4$)— or $L_2$ is absent;
$R_2$ is chosen from
  hydrogen,
  lower alkyl, and
  lower alkyl substituted with lower alkoxy, amino, (alkyl)amino, (dialkyl)amino, or hydroxy; or for each occurrence, $R_3$ is independently chosen from
halo,
cyano,
lower alkoxy,
lower alkyl optionally substituted with amino, (alkyl)amino, or di(alkyl)amino, and
ethynyl optionally substituted with tri(alkyl)silyl;
$R_4$ is chosen from hydrogen and lower alkyl; and
m is 0, 1, or 2,
wherein the compound of Formula I, or a pharmaceutically acceptable salt thereof, is labeled with one or more positron-emitting radionuclides.

In some embodiments, $L_1$ is absent.
In some embodiments, $L_1$ is —CH═CH—.
In some embodiments, $R_1$ is

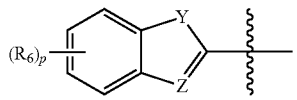

wherein
Y is chosen from O, $NR_7$, and S;
$R_7$ is chosen from hydrogen and lower alkyl;
Z is chosen from CH and N;
for each occurrence, $R_6$ is chosen from halo, hydroxyl, lower alkoxy, and lower alkoxy substituted with halo, heteroaryl, or optionally substituted amino; and
p is chosen from 0, 1 and 2.

In some embodiments, Y is $NR_7$ and Z is N. In some embodiments, Y is $NR_7$ and $R_7$ is chosen from hydrogen and methyl.

In some embodiments, Y is O and Z is CH.
In some embodiments, Y is S and Z is N.
In some embodiments, Y is O and Z is N.
In some embodiments, p is 0.
In some embodiments, p is 1. In some embodiments, $R_6$ is chosen from bromo, fluoro, methoxy, hydroxyl, 2-fluoroethoxy, pyridine-3-ylmethoxy, aminomethoxy, (methylamino)ethoxy, and (dimethylamino)ethoxy.

In some embodiments, $R_1$ is heteroaryl substituted with (5-methoxypyrazin-2-yl)methoxy, 5-methoxypyrazin-2-yl)methoxy, 5-(tert-butoxycarbonyl), or (5-methoxypyridin-2-yl)methoxy. In some embodiments, $R_1$ is heteroaryl substituted with (5-methoxypyrazin-2-yl)methoxy, 5-methoxypyrazin-2-yl)methoxy, or 5-(tert-butoxycarbonyl).

In some embodiments, $R_1$ is chosen from 5-fluoro-1-benzofuran-2-yl, 5-methoxy-1-benzofuran-2-yl, 5-hydroxy-1-benzofuran-2-yl, 5-(2-fluoroethoxy)-1-benzofuran-2-yl, 6-methoxy-1-benzofuran-2-yl, 5-bromo-1-benzofuran-2-yl, 5-methoxy-1-methyl-1H-1,3-benzodiazol-2-yl, 5-methoxy-1H-1,3-benzodiazol-2-yl, 6-methoxy-1-methyl-1H-1,3-benzodiazol-2-yl, 5-(pyridine-3-yl)methoxy-1-benzofuran-2-yl, 6-methoxy-1,3-benzothiazole-2-yl, 5-methoxy-1,3-benzoxazol-2-yl, 5-[2-(dimethylamino)ethoxy]-1-benzofuran-2-yl, and 5-[(5-methoxypyridin-2-yl)methoxy]pyrazine-2-yl.
In some embodiments, $R_1$ is chosen from 5-fluoro-1-benzofuran-2-yl, 5-methoxy-1-benzofuran-2-yl, 5-hydroxy-1-benzofuran-2-yl, 5-(2-fluoroethoxy)-1-benzofuran-2-yl, 6-methoxy-1-benzofuran-2-yl, 5-bromo-1-benzofuran-2-yl, 5-methoxy-1-methyl-1H-1,3-benzodiazol-2-yl, 5-methoxy-1H-1,3-benzodiazol-2-yl, 6-methoxy-1-methyl-1H-1,3-benzodiazol-2-yl, 5-(pyridine-3-yl)methoxy-1-benzofuran-2-yl, 6-methoxy-1,3-benzothiazole-2-yl, 5-methoxy-1,3-benzoxazol-2-yl, and 5-[2-(dimethylamino)ethoxy]-1-benzofuran-2-yl.

In some embodiments, $R_1$ is chosen from phenyl optionally substituted with one, two, or three groups independently chosen from
cyano,
halo,
heterocycloalkyl,
heteroaryl,
lower alkyl,
lower alkyl substituted with one or two substituents independently chosen from
lower alkoxy substituted with heteroaryl,
—C(O)O-lower alkyl,
hydroxyl,
lower alkynyloxy,
lower alkoxy, and
lower alkoxy substituted with one or two substituents independently chosen from
halo,
heteroaryl,
heteroaryl substituted with lower alkoxy,
optionally substituted amino,
alkyl substituted with heteroaryl, and
alkyl substituted with heteroaryl substituted with lower alkoxy.

In some embodiments, $R_1$ is phenyl optionally substituted with one, two, or three groups independently chosen from methoxy, pyridine-3-ylmethoxy, pyrazin-2-yl, cyano, (5-methoxypyrazin-2-yl)methoxy, (prop-2-yn-1-yloxy), 5H,6H-imdazo[2,1-b][1,3]thiazol-3-ylmethoxy, and [(5-methoxypyridin-2-yl)methyl]amino.

In some embodiments, $R_1$ is 4-methoxyphenyl, 3-(pyridine-3-ylmethoxy)phenyl, 4-(pyridine-3-ylmethoxy)phenyl, 3-(pyrazin-2-yl)phenyl, 4-(pyrazin-2-yl)phenyl, 4-cyanophenyl, 4-[(5-methoxypyrazin-2-yl)methoxy]phenyl, and 4-(prop-2-yn-1-yloxy)phenyl.

In some embodiments, $R_1$ is chosen from 5-(tert-butoxycarbonyl)-4,5,6,7-tetrahydrofuro[3,2-c]pyridin-2-yl, 2,3-dihydro-1,4,-benzodioxin-6-yl, 5-bromofuran-2-yl, 1-benzofuran-5-yl,11-methoxy-7-thia-2,5-diazatricyclo[6.4.0.0$^{2,6}$]dodeca-1(12),3,5,8,10-pentaen-4-yl and 10-methoxy-7-thia-2,5-diazatricyclo[6.4.0.0$^{2,6}$]dodeca-1(12),3,5,8,10-pentaen-4-yl.

In some embodiments, $L_2$ is absent.
In some embodiments, $L_2$ is absent and $R_2$ is hydrogen.
In some embodiments, $L_2$ is absent and $R_2$ is lower alkyl or lower alkyl substituted with lower alkoxy, amino, (alkyl)amino or (dialkyl)amino.

In some embodiments, $L_2$ is —$N(R_4)$—. In some embodiments, $L_2$ is —$N(R_4)$— and $R_4$ is hydrogen or methyl. In some embodiments, $L_2$ is —$N(R_4)$— and $R_2$ is chosen from hydrogen, lower alkyl and lower alkyl substituted with hydroxy, lower alkoxy, amino, (alkyl)amino or (dialkyl)amino. In some embodiments, $L_2$ is —$N(R_4)$— and $R_2$ is chosen from hydrogen, methyl, 2-methoxyethyl, 2-hydroxyethyl, and 2-(dimethylamino)ethyl.

In some embodiments, m is 0.
In some embodiments, m is 1. In some embodiments, $R_3$ is chosen from bromo, chloro, fluoro, aminomethyl, 2-(trimethylsilyl)ethynyl, ethynyl, methoxy, and cyano. In some embodiments, $R_3$ is chosen from bromo, chloro, fluoro, methoxy, and cyano. In some embodiments, $R_3$ is cyano.

Also provided is an imaging agent wherein the compound is chosen from 2-(5-fluoro-1-benzofuran-2-yl)-N-methylimidazo[1,2-a] pyridin-3-amine;
2-(5-methoxy-1-benzofuran-2-yl)-N-methylimidazo[1,2-a] pyridin-3-amine;
6-fluoro-2-(5-methoxy-1-benzofuran-2-yl)-N-methylimidazo[1,2-a]pyridin-3-amine;
7-fluoro-2-(5-methoxy-1-benzofuran-2-yl)-N-methylimidazo[1,2-a]pyridin-3-amine;
2-(5-methoxy-1-benzofuran-2-yl)-3-(methylamino)imidazo [1,2-a]pyridine-7-carbonitrile;
2-[6-fluoro-3-(methylamino)imidazo[1,2-a]pyridin-2-yl]-1-benzofuran-5-ol;
2-(5-methoxy-1-benzofuran-2-yl)-N-(2-methoxyethyl)imidazo[1,2-a]pyridin-3-amine;
2-[7-fluoro-3-(methylamino)imidazo[1,2-a]pyridin-2-yl]-1-benzofuran-5-ol;
2-{3-[(2-hydroxyethyl)amino]imidazol[1,2-a]pyridin-2-yl}-1-benzofuran-5-ol;
2-(5-hydroxy-1-benzofuran-2-yl)-3-(methylamino)imidazo [1,2-a]pyridine-7-carbonitrile;
2-[5-(2-fluoroethoxy)-1-benzofuran-2-yl]-3-(methylamino) imidazo[1,2-a]pyridine-7-carbonitrile;
2-(4-methoxyphenyl)-3-(methylamino)imidazo[1,2-a]pyridine-7-carbonitrile;
2-(6-methoxy-1-benzofuran-2-yl)-3-(methylamino)imidazo [1,2-a]pyridine-7-carbonitrile;
7-methoxy-2-(5-methoxy-1-benzofuran-2-yl)-N-methylimidazo[1,2-a]pyridin-3-amine;
3-(methylamino)-2-[3-(pyridin-3-ylmethoxy)phenyl]imidazo[1,2-a]pyridine-7-carbonitrile;
3-(methylamino)-2-[4-(pyridin-3-ylmethoxy)phenyl]imidazo[1,2-a]pyridine-7-carbonitrile;
7-chloro-2-(5-methoxy-1-benzofuran-2-yl)-N-methylimidazo[1,2-a]pyridin-3-amine;
7-bromo-2-(5-methoxy-1-benzofuran-2-yl)-N-methylimidazo[1,2-a]pyridin-3-amine;
2-(5-methoxy-1-benzofuran-2-yl)-3-(methylamino)imidazo [1,2-a]pyridine-6-carbonitrile;
2-(5-bromo-1-benzofuran-2-yl)-3-(methylamino)imidazo[1, 2-a]pyridine-7-carbonitrile;
3-(methylamino)-2-[3-(pyrazin-2-yl)phenyl]imidazo[1,2-a] pyridine-7-carbonitrile;
3-(methylamino)-2-[4-(pyrazin-2-yl)phenyl]imidazo[1,2-a] pyridine-7-carbonitrile;
2-[(E)-2-(4-methoxyphenyl)ethenyl]-3-(methylamino)imidazo[1,2-a]pyridine-7-carbonitrile;
2-(5-methoxy-1-benzofuran-2-yl)-3-[(2-methoxyethyl) amino]imidazo[1,2-a]pyridine-7-carbonitrile;
2-(2,3-dihydro-1,4-benzodioxin-6-yl)-3-(methylamino)imidazo[1,2-a]pyridine-7-carbonitrile;
2-(5-bromofuran-2-yl)-3-(methylamino)imidazo[1,2-a]pyridine-7-carbonitrile;
2-(4-cyanophenyl)-3-(methylamino)imidazo[1,2-a]pyridine-7-carbonitrile;
2-(1-benzofuran-5-yl)-3-(methylamino)imidazo[1,2-a]pyridine-7-carbonitrile;
3-(methylamino)-2-[4-(prop-2-yn-1-yloxy)phenyl]imidazo [1,2-a]pyridine-7-carbonitrile;
2-(5-fluoro-1-benzofuran-2-yl)-3-(methylamino)imidazo[1, 2-a]pyridine-7-carbonitrile;
2-{3-[(5-methoxypyrazin-2-yl)methoxy]phenyl}-3-(methylamino)imidazo[1,2-a]pyridine-7-carbonitrile;
2-{5-[(5-methoxypyrazin-2-yl)methoxy]pyridin-2-yl}-3-(methylamino)imidazo[1,2-a]pyridine-7-carbonitrile;
3-(dimethylamino)-2-(5-methoxy-1-benzofuran-2-yl)imidazo[1,2-a]pyridine-7-carbonitrile;

2-(5-methoxy-1-methyl-1H-1,3-benzodiazol-2-yl)-3-(methylamino)imidazo[1,2-a]pyridine-7-carbonitrile;
2-(6-methoxy-1,3-benzothiazol-2-yl)-3-(methylamino)imidazo[1,2-a]pyridine-7-carbonitrile;
2-(5-methoxy-1,3-benzoxazol-2-yl)-3-(methylamino)imidazo[1,2-a]pyridine-7-carbonitrile;
2-(5-methoxy-1H-1,3-benzodiazol-2-yl)-3-(methylamino) imidazo[1,2-a]pyridine-7-carbonitrile;
2-(5-methoxy-1-benzofuran-2-yl)imidazo[1,2-a]pyridine-7-carbonitrile;
2-(6-methoxy-1-methyl-1H-1,3-benzodiazol-2-yl)-3-(methylamino)imidazo[1,2-a]pyridine-7-carbonitrile;
3-(methylamino)-2-[5-(pyridin-3-ylmethoxy)-1-benzofuran-2-yl]imidazo[1,2-a]pyridine-7-carbonitrile;
3-amino-2-[5-(2-fluoroethoxy)-1-benzofuran-2-yl]imidazo [1,2-a]pyridine-7-carbonitrile;
3-amino-2-(5-methoxy-1-benzofuran-2-yl)imidazo[1,2-a] pyridine-7-carbonitrile;
2-(5-methoxy-1-benzofuran-2-yl)-3-(methoxymethyl)imidazo[1,2-a]pyridine-7-carbonitrile;
3-[(dimethylamino)methyl]-2-(5-methoxy-1-benzofuran-2-yl)imidazo[1,2-a]pyridine-7-carbonitrile;
2-{5-[2-(dimethylamino)ethoxy]-1-benzofuran-2-yl}-3-(methylamino)imidazo[1,2-a]pyridine-7-carbonitrile;
3-(methylamino)-2-{4-[(pyridin-3-ylmethoxy)methyl] phenyl}imidazo[1,2-a]pyridine-7-carbonitrile;
3-{[2-(dimethylamino)ethyl]amino}-2-(5-methoxy-1-benzofuran-2-yl)imidazo[1,2-a]pyridine-7-carbonitrile tert-butyl 2-[7-cyano-3-(methylamino)imidazo[1,2-a]pyridin-2-yl]-4H,5H,6H,7H-furo[3,2-c]pyridine-5-carboxylate;
7-(aminomethyl)-2-(5-methoxy-1-benzofuran-2-yl)-N-methylimidazo[1,2-a]pyridin-3-amine;
3-(methylamino)-2-{3-[(pyridin-3-ylmethoxy)methyl] phenyl}imidazo[1,2-a]pyridine-7-carbonitrile;
2-{4-[(5-methoxypyrazin-2-yl)methoxy]phenyl}-3-(methylamino)imidazo[1,2-a]pyridine-7-carbonitrile;
2-{6-[(5-methoxypyrazin-2-yl)methoxy]pyridin-3-yl}-3-(methylamino)imidazo[1,2-a]pyridine-7-carbonitrile;
2-(5-methoxy-1-benzofuran-2-yl)-N-methyl-7-[2-(trimethylsilyl)ethynyl]imidazo[1,2-a]pyridin-3-amine;
7-ethynyl-2-(5-methoxy-1-benzofuran-2-yl)-N-methylimidazo[1,2-a]pyridin-3-amine;
2-(4-{1[(5-methoxypyridin-2-yl)methyl]amino}phenyl)-3-(methylamino)imidazo[1,2-a]pyridine-7-carbonitrile;
2-(4-{5H,6H-imidazo[2,1-b][1,3]thiazol-3-ylmethoxy}phenyl)-3-(methylamino)imidazo[1,2-a]pyridine-7-carbonitrile;
2-{10-methoxy-7-thia-2,5-diazatricyclo[6.4.0.0$^{2,6}$]dodeca-1 (12),3,5,8,10-pentaen-4-yl}-3-(methylamino)imidazo[1, 2-a]pyridine-7-carbonitrile;
2-{11-methoxy-7-thia-2,5-diazatricyclo[6.4.0.0$^{2,6}$]dodeca-1 (12),3,5,8,10-pentaen-4-yl}-3-(methylamino)imidazo[1, 2-a]pyridine-7-carbonitrile; and
2-{5-[(5-methoxypyridin-2-yl)methoxy]pyrazin-2-yl}-3-(methylamino)imidazo[1,2-a]pyridine-7-carbonitrile,
or a pharmaceutically acceptable salt thereof, wherein the compound of Formula I, or a pharmaceutically acceptable salt thereof, is labeled with one or more positron-emitting radionuclides.

Also provided is an imaging agent wherein the compound is chosen from
2-(5-fluoro-1-benzofuran-2-yl)-N-methylimidazo[1,2-a] pyridin-3-amine;
2-(5-methoxy-1-benzofuran-2-yl)-N-methylimidazo[1,2-a] pyridin-3-amine;
6-fluoro-2-(5-methoxy-1-benzofuran-2-yl)-N-methylimidazo[1,2-a]pyridin-3-amine;

7-fluoro-2-(5-methoxy-1-benzofuran-2-yl)-N-methylimidazo[1,2-a]pyridin-3-amine;
2-(5-methoxy-1-benzofuran-2-yl)-3-(methylamino)imidazo[1,2-a]pyridine-7-carbonitrile;
2-[6-fluoro-3-(methylamino)imidazo[1,2-a]pyridin-2-yl]-1-benzofuran-5-ol;
2-(5-methoxy-1-benzofuran-2-yl)-N-(2-methoxyethyl)imidazo[1,2-a]pyridin-3-amine;
2-[7-fluoro-3-(methylamino)imidazo[1,2-a]pyridin-2-yl]-1-benzofuran-5-ol;
2-{3-[(2-hydroxyethyl)amino]imidazo[1,2-a]pyridin-2-yl}-1-benzofuran-5-ol;
2-(5-hydroxy-1-benzofuran-2-yl)-3-(methylamino)imidazo[1,2-a]pyridine-7-carbonitrile;
2-[5-(2-fluoroethoxy)-1-benzofuran-2-yl]-3-(methylamino)imidazo[1,2-a]pyridine-7-carbonitrile;
2-(4-methoxyphenyl)-3-(methylamino)imidazo[1,2-a]pyridine-7-carbonitrile;
2-(6-methoxy-1-benzofuran-2-yl)-3-(methylamino)imidazo[1,2-a]pyridine-7-carbonitrile;
7-methoxy-2-(5-methoxy-1-benzofuran-2-yl)-N-methylimidazo[1,2-a]pyridin-3-amine;
3-(methylamino)-2-[3-(pyridin-3-ylmethoxy)phenyl]imidazo[1,2-a]pyridine-7-carbonitrile;
3-(methylamino)-2-[4-(pyridin-3-ylmethoxy)phenyl]imidazo[1,2-a]pyridine-7-carbonitrile;
7-chloro-2-(5-methoxy-1-benzofuran-2-yl)-N-methylimidazo[1,2-a]pyridin-3-amine;
7-bromo-2-(5-methoxy-1-benzofuran-2-yl)-N-methylimidazo[1,2-a]pyridin-3-amine;
2-(5-methoxy-1-benzofuran-2-yl)-3-(methylamino)imidazo[1,2-a]pyridine-6-carbonitrile;
2-(5-bromo-1-benzofuran-2-yl)-3-(methylamino)imidazo[1,2-a]pyridine-7-carbonitrile;
3-(methylamino)-2-[3-(pyrazin-2-yl)phenyl]imidazo[1,2-a]pyridine-7-carbonitrile;
3-(methylamino)-2-[4-(pyrazin-2-yl)phenyl]imidazo[1,2-a]pyridine-7-carbonitrile;
2-[(E)-2-(4-methoxyphenyl)ethenyl]-3-(methylamino)imidazo[1,2-a]pyridine-7-carbonitrile;
2-(5-methoxy-1-benzofuran-2-yl)-3-[(2-methoxyethyl)amino]imidazo[1,2-a]pyridine-7-carbonitrile;
2-(2,3-dihydro-1,4-benzodioxin-6-yl)-3-(methylamino)imidazo[1,2-a]pyridine-7-carbonitrile;
2-(5-bromofuran-2-yl)-3-(methylamino)imidazo[1,2-a]pyridine-7-carbonitrile;
2-(4-cyanophenyl)-3-(methylamino)imidazo[1,2-a]pyridine-7-carbonitrile;
2-(1-benzofuran-5-yl)-3-(methylamino)imidazo[1,2-a]pyridine-7-carbonitrile;
3-(methylamino)-2-[4-(prop-2-yn-1-yloxy)phenyl]imidazo[1,2-a]pyridine-7-carbonitrile;
2-(5-fluoro-1-benzofuran-2-yl)-3-(methylamino)imidazo[1,2-a]pyridine-7-carbonitrile;
2-{3-[(5-methoxypyrazin-2-yl)methoxy]phenyl}-3-(methylamino)imidazo[1,2-a]pyridine-7-carbonitrile;
2-{5-[(5-methoxypyrazin-2-yl)methoxy]pyridin-2-yl}-3-(methylamino)imidazo[1,2-a]pyridine-7-carbonitrile;
3-(dimethylamino)-2-(5-methoxy-1-benzofuran-2-yl)imidazo[1,2-a]pyridine-7-carbonitrile;
2-(5-methoxy-1-methyl-1H-1,3-benzodiazol-2-yl)-3-(methylamino)imidazo[1,2-a]pyridine-7-carbonitrile;
2-(6-methoxy-1,3-benzothiazol-2-yl)-3-(methylamino)imidazo[1,2-a]pyridine-7-carbonitrile;
2-(5-methoxy-1,3-benzoxazol-2-yl)-3-(methylamino)imidazo[1,2-a]pyridine-7-carbonitrile;
2-(5-methoxy-1H-1,3-benzodiazol-2-yl)-3-(methylamino)imidazo[1,2-a]pyridine-7-carbonitrile;
2-(5-methoxy-1-benzofuran-2-yl)imidazo[1,2-a]pyridine-7-carbonitrile;
2-(6-methoxy-1-methyl-1H-1,3-benzodiazol-2-yl)-3-(methylamino)imidazo[1,2-a]pyridine-7-carbonitrile;
3-(methylamino)-2-[5-(pyridin-3-ylmethoxy)-1-benzofuran-2-yl]imidazo[1,2-a]pyridine-7-carbonitrile;
3-amino-2-[5-(2-fluoroethoxy)-1-benzofuran-2-yl]imidazo[1,2-a]pyridine-7-carbonitrile;
3-amino-2-(5-methoxy-1-benzofuran-2-yl)imidazo[1,2-a]pyridine-7-carbonitrile;
2-(5-methoxy-1-benzofuran-2-yl)-3-(methoxymethyl)imidazo[1,2-a]pyridine-7-carbonitrile;
3-[(dimethylamino)methyl]-2-(5-methoxy-1-benzofuran-2-yl)imidazo[1,2-a]pyridine-7-carbonitrile;
2-{5-[2-(dimethylamino)ethoxy]-1-benzofuran-2-yl}-3-(methylamino)imidazo[1,2-a]pyridine-7-carbonitrile;
3-(methylamino)-2-{4-[(pyridin-3-ylmethoxy)methyl]phenyl}imidazo[1,2-a]pyridine-7-carbonitrile;
3-{[2-(dimethylamino)ethyl]amino}-2-(5-methoxy-1-benzofuran-2-yl)imidazo[1,2-a]pyridine-7-carbonitrile
tert-butyl 2-[7-cyano-3-(methylamino)imidazo[1,2-a]pyridin-2-yl]-4H,5H,6H,7H-furo[3,2-c]pyridine-5-carboxylate;
7-(aminomethyl)-2-(5-methoxy-1-benzofuran-2-yl)-N-methylimidazo[1,2-a]pyridin-3-amine;
3-(methylamino)-2-{3-[(pyridin-3-ylmethoxy)methyl]phenyl}imidazo[1,2-a]pyridine-7-carbonitrile;
2-{4-[(5-methoxypyrazin-2-yl)methoxy]phenyl}-3-(methylamino)imidazo[1,2-a]pyridine-7-carbonitrile;
2-{6-[(5-methoxypyrazin-2-yl)methoxy]pyridin-3-yl}-3-(methylamino)imidazo[1,2-a]pyridine-7-carbonitrile;
2-(5-methoxy-1-benzofuran-2-yl)-N-methyl-7-[2-(trimethylsilyl)ethynyl]imidazo[1,2-a]pyridin-3-amine;
7-ethynyl-2-(5-methoxy-1-benzofuran-2-yl)-N-methylimidazo[1,2-a]pyridin-3-amine;
2-(4-{[(5-methoxypyridin-2-yl)methyl]amino}phenyl)-3-(methylamino)imidazo[1,2-a]pyridine-7-carbonitrile;
2-(4-{5H,6H-imidazo[2,1-b][1,3]thiazol-3-ylmethoxy}phenyl)-3-(methylamino)imidazo[1,2-a]pyridine-7-carbonitrile;
2-{10-methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile; and
2-{11-methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile,
or a pharmaceutically acceptable salt thereof, wherein the compound of Formula I, or a pharmaceutically acceptable salt thereof, is labeled with one or more positron-emitting radionuclides.

The compounds of Formula I, or a pharmaceutically acceptable salt thereof are labeled with one or more positron-emitting radionuclides. Suitable positron-emitting radionuclides that may be incorporated in the compounds described herein, but are not limited to, $^{11}$C, $^{13}$N, $^{15}$O, $^{18}$F, $^{52}$Fe, $^{62}$Cu, $^{64}$Cu, $^{68}$Ga, $^{74}$As, $^{82}$R$^b$, $^{89}$Zr, $^{122}$I, and $^{124}$I. In some embodiments, the one or more positron-emitting radionuclides are selected from: $^{11}$C, $^{13}$N, $^{15}$, $^{18}$F, $^{76}$Br, and $^{124}$I. In some embodiments the one or more positron-emitting radionuclides are selected from $^{11}$C, $^{13}$N, $^{15}$, and $^{18}$F.

Non-metal radionuclides may be covalently linked to the compounds described herein by a reaction well known from the state of art. When the radionuclide is a metallic positron-emitter, it is understood that labeling may require the use of a chelating agent. Such chelating agents are well known from the state of the art.

A PET imaging agent may be labelled with the positron emitter $^{11}$C or $^{18}$F. Methods for the introduction of $^{11}$C may include, but are not limited to, alkylation with [$^{11}$C]iodomethane or [$^{11}$C]methyl triflate. Carbon-11 has a half-life of approximately 20 minutes, thus $^{11}$C needs to be generated in an on-site cyclotron, and is generally produced as [$^{11}$C]carbon dioxide. The [$^{11}$C]carbon dioxide is converted to the chemical species appropriate for the radiosynthesis (generally [$^{11}$C]iodomethane or the like), and the synthesis of the radiopharmaceutical is completed and used on-site in a PET imaging study after the appropriate radiochemical purity and specific activity have been determined. Typical methods of introducing $^{18}$F may include but are not limited to displacement of a halide, tosylate, or other leaving group with [$^{18}$F]tetrabutylamonium fluoride or [$^{18}$F]potassium fluoride kryptofix-222. Fluorine-18 has a half life of approximately 110 minutes, thus synthesis of [$^{18}$F]radiopharmaceuticals need not necessarily have to occur at the site of the cyclotron nor proximal to the PET imaging study center. General methods for the introduction of these positron emitters are described in the literature (Miller et al., *Angewandte Chemie International Edition*, 47 (2008), 8998-9033).

Provided are methods of generating diagnostic images in an individual comprising administering an effective amount of an imaging agent described herein to an individual, and generating an image of at least a part of the individual.

Also provided are methods of generating diagnostic images in a biological sample comprising contacting the biological sample with an effective amount of an imaging agent described herein and generating an image of the positron-emitter labeled compound associated with the biological sample. In this method both the contacting and the generating may be conducted in vitro, alternatively the contacting is in vivo and the generating in vitro.

Also provided are methods for detecting the presence or absence of a neurodegenerative pathologic process associated with huntingtin protein (HTT protein) in an individual comprising: administering an effective amount of a positron-emitter labeled compound described herein; generating an image to detect the presence or absence of HTT protein aggregates in the brain of the individual; and detecting the presence or absence of the pathologic process. In some embodiments, the HTT protein aggregates are present in the basal ganglia of the brain of the individual. In some embodiments, the pathologic process is Huntington's disease (HD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Also provided are diagnostic methods of using the imaging agents to monitor disease progression in a patient by quantifying the change in levels of the target aggregates in the patient.

Also provided are methods for detecting the presence or absence of a neurodegenerative pathologic process associated with huntingtin protein (HTT protein) in an individual comprising: administering an effective amount of a positron-emitter labeled compound described herein; generating an image to detect the presence or absence of HTT protein aggregates in the individual; and detecting the presence or absence of the pathologic process. In some embodiments, the HTT protein monomers or aggegates are present in the brain, liver, heart, or muscle of said individual. In some embodiments, the HTT protein aggregates are present in the basal ganglia, cortex, hippocampus, or brain stem of the brain of the individual. In some embodiments, the pathologic process is Huntington's disease (HD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Also provided are methods for detecting the presence or absence of a neurodegenerative pathologic process associated with β-amyloid protein in an individual comprising: administering an effective amount of a positron-emitter labeled compound described herein; generating an image to detect the presence or absence of β-amyloid protein aggregates in the individual; and detecting the presence or absence of the pathologic process. In some embodiments, the β-amyloid protein monomers or aggegates are present in the brain, liver, heart, or muscle of said individual. In some embodiments, the β-amyloid protein aggregates are present in the basal ganglia, cortex, hippocampus, or brain stem of the brain of the individual. In some embodiments, the pathologic process is Alzheimer's Disease (AD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Provided herein are compounds having suitable HTT protein aggregate or β-amyloid protein aggregate binding kinetics to function as efficient imaging agents for HTT protein aggregates or β-amyloid protein aggregates. The requirements of the compounds of the invention to function as efficient imaging agents for HTT protein aggregates are: 1) a high affinity for HTT protein aggregates; 2) a low affinity for nearby structures; 3) slow dissociation kinetics from HTT protein aggregates, which may conveniently be expressed as the dissociation rate constant $k_{diss}$ as defined in the following equation, wherein A and B refer to the HTT protein aggregate and the imaging agent, and $k_{assn}$ is the association rate constant.

$$d[AB]/dt = k_{assn}[A][B] - k_{diss}[AB]$$

The part of the brain most affected by HD, and thus most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

The term basal ganglia, refers to a group of subcortical nuclei responsible primarily for motor control, as well as other roles such as motor learning, executive functions and behaviors, and emotions. Disruption of the basal ganglia network forms the basis for several movement disorders. Normal function of the basal ganglia requires fine tuning of neuronal excitability within each nucleus to determine the exact degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

Provided are methods for imaging part of the brain of an individual involving administering a positron-emitter labeled compound described herein to the individual, e.g. into the individual's vascular system, from where it passes through the blood-brain barrier, and then generating an image of at least the part of the individual's brain to which the compound has distributed.

Also provided are pharmaceutical compositions comprising an effective amount of a positron-emitter labeled compound described herein, or a salt thereof, together with one or more pharmaceutically-acceptable adjuvants, excipients or diluents.

An imaging agent or pharmaceutical composition thereof may be administered to a patient in need of treatment via any suitable route. Routes of administration may include, for example, parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

An imaging agent or pharmaceutical composition thereof may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

Also provided are uses of positron-emitter labeled compounds described herein for the manufacture of an imaging agent for use in a method of diagnosis of an individual.

Provided are methods of generating diagnostic images comprising proton emission tomography (PET). PET involves the administration of a positron-emitting radionuclide tracer to an individual. Once the tracer has had sufficient time to associate with the target of interest, the individual is placed within a scanning device comprising a ring of scintillation detectors. An emitted positron travels through the individual's tissue for a short (isotope-dependent) distance, until it interacts with an electron. The interaction annihilates both the electron and the positron, producing a pair of photons moving in approximately opposite directions. These are detected when they reach a scintillator in the scanning device. Photons that do not arrive in pairs are ignored.

Also provided are methods of generating diagnostic images comprising PET with concurrent computed tomography imaging (PET/CT), or with concurrent magnetic resonance imaging (PET/MRI). Computed tomography uses X-rays to show the structure of the brain, while magnetic resonance imaging uses magnetic fields and radio waves.

Other uses of the disclosed imaging agents and methods will become apparent to those skilled in the art based upon, inter alia, a review of this disclosure.

As will be recognized, the steps of the methods described herein need not be performed any particular number of times or in any particular sequence. Additional objects, advantages and novel features of the disclosure will become apparent to those skilled in the art upon examination of the following examples thereof, which are intended to be illustrative and not intended to be limiting.

EXAMPLES

General Experimental Details

Commercially available reagents and solvents (HPLC grade) were used without further purification. $^1$H NMR spectra were recorded on a Bruker DRX 500 MHz spectrometer or a Bruker DPX 250 MHz spectrometer in deuterated solvents. Chemical shifts ($\delta$) are in parts per million. SCX chromatography was performed with Biotage Isolute Flash SCX-2 loading the sample in methanol and eluting with methanol then 5% ammonia in methanol.

Analytical HPLC-MS (METCR1278), was performed on Shimadzu LCMS-2010EV systems using reverse phase Atlantis dC18 columns (3 µm, 2.1×50 mm), gradient 5-100% B (A=water/0.1% formic acid, B=acetonitrile/0.1% formic acid) over 3 minutes injection volume 3 µL, flow=1.0 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively, (METCR1416) analytical HPLC-MS on Shimadzu LCMS-2010EV systems using reverse phase Water Atlantis dC18 columns (3 µm, 2.1×100 mm), gradient 5-100% B (A=water/0.1% formic acid, B=acetonitrile/0.1% formic acid) over 7 minutes, injection volume 3 µL, flow=0.6 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 µM, 2.1 mm×100 mm at a column temperature of 40° C., gradient 5-100% B (A=water/0.1% formic acid; B=acetonitrile/0.1% formic acid) over 5.3 minutes, then 100% B for 0.5 minute, flow=0.6 mL/minute. UV spectra were recorded at 215 nm using a Waters Acquity photo diode array. Mass spectra were obtained over the range m/z 150 to 850 at a sampling rate of 5 scans per second using a Waters SQD. Data were integrated and reported using Waters MassLynx and OpenLynx software.

All example compounds display an LC purity of >95% unless stated otherwise.

Method 1

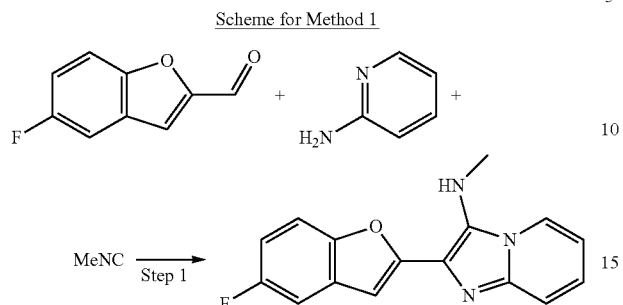

Scheme for Method 1

Step 1, Method 1: 2-(5-Fluoro-1-benzofuran-2-yl)-N-methylimidazo[1,2-a]pyridin-3-amine To a solution of pyridin-2-amine (0.20 g, 2 mmol) and 5-fluorobenzofuran-2-carboxaldehyde (0.35 g, 2 mmol) in methanol (10 mL) was added methyl isocyanide (0.09 mL, 1.9 mmol), followed by acetic acid (0.5 mL). The reaction was stirred at room temperature for 4 days. 1 M sodium hydroxide (5 mL) was added and the methanol was evaporated. Water (10 mL) was added, the mixture washed with ethyl acetate and acidified with 1 M hydrochloric acid. The precipitate was filtered off, and then washed with water and ethyl acetate to give the title compound 0.26 g (46% yield) as a yellow solid.

Example 1, Method 1: 2-(5-Fluoro-1-benzofuran-2-yl)-N-methylimidazo[1,2-a]pyridin-3-amine $\delta_H$ NMR (500 MHz, DMSO) 8.28 (d, J=6.85 Hz, 1H), 7.64 (dd, J=4.26, 8.98 Hz, 1H), 7.43-7.53 (m, 2H), 7.18-7.27 (m, 2H), 7.12 (dt, J=2.66, 9.25 Hz, 1H), 6.88-6.97 (m, 1H), 5.06 (q, J=5.48 Hz, 1H), 2.83 (d, J=5.48 Hz, 3H). Tr(METCR1416)=3.08 min (ES$^+$) (M+H)$^+$282.

The following examples were prepared using Method 1 described above:

TABLE 1

| Ex. | Structure | Mol. Weight | IUPAC Name | LCMS data |
|---|---|---|---|---|
| 1 | 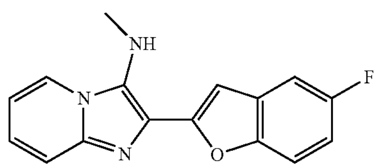 [SMILES: CNc1c(-c2cc3cc(F)ccc3o2)nc2ccccn12] | 281.28 | 2-(5-Fluoro-1-benzofuran-2-yl)-N-methylimidazo[1,2-a]pyridin-3-amine | Tr(METCR1416) = 3.08 min, (ES$^+$) (M + H)$^+$ 282 |
| 2 | 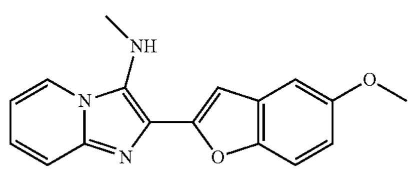 [SMILES: CNc1c(-c2cc3cc(OC)ccc3o2)nc2ccccn12] | 293.32 | 2-(5-Methoxy-1-benzofuran-2-yl)-N-methylimidazo[1,2-a]pyridin-3-amine | Tr(METCR1416) = 3 min, (ES$^+$) (M + H)$^+$ 294 |
| 3 | 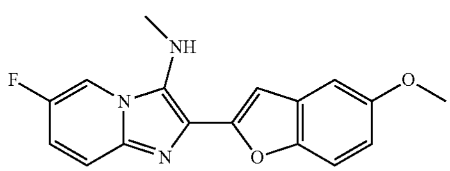 [SMILES: CNc1c(-c2cc3cc(OC)ccc3o2)nc2ccc(F)cn12] | 311.31 | 6-Fluoro-2-(5-methoxy-1-benzofuran-2-yl)-N-methylimidazo[1,2-a]pyridin-3-amine | Tr(METCR1416) = 3.48 min, (ES$^+$) (M + H)$^+$ 312 |
| 4 | 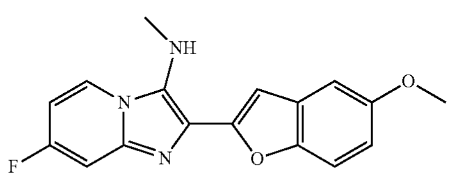 [SMILES: CNc1c(-c2cc3cc(OC)ccc3o2)nc2cc(F)ccn12] | 311.31 | 7-Fluoro-2-(5-methoxy-1-benzofuran-2-yl)-N-methylimidazo[1,2-a]pyridin-3-amine | Tr(METCR1416) = 3.27 min, (ES$^+$) (M + H)$^+$ 312 |
| 5 | 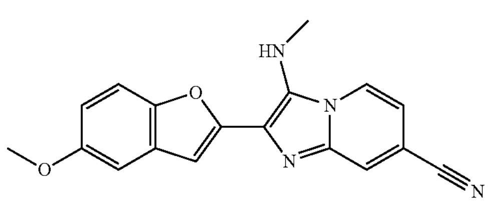 [SMILES: CNc1c(-c2cc3cc(OC)ccc3o2)nc2cc(C#N)ccn12] | 318.33 | 2-(5-Methoxy-1-benzofuran-2-yl)-3-(methylamino)imidazo[1,2-a]pyridine-7-carbonitrile | Tr(METCR1416) = 4.09 min, (ES$^+$) (M + H)$^+$ 319 |

TABLE 1-continued

| Ex. | Structure | Mol. Weight | IUPAC Name | LCMS data |
|---|---|---|---|---|
| 6 | 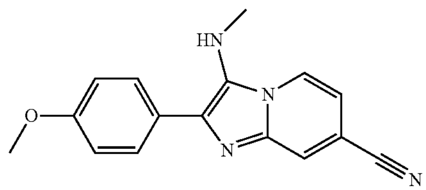 [SMILES: CNc1c(-c2ccc(OC)cc2)nc2cc(C#N)ccn12] | 278.31 | 2-(4-Methoxyphenyl)-3-(methylamino)imidazo[1,2-a]pyridine-7-carbonitrile | Tr(MET-uHPLC-AB-101) = 2.17 min, (ES⁺) (M + H)⁺ 279 |
| 7 | 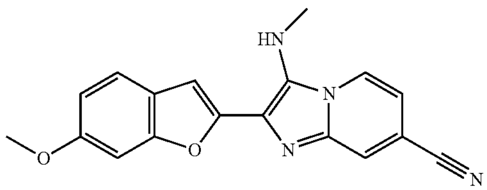 [SMILES: CNc1c(-c2cc3ccc(OC)cc3o2)nc2cc(C#N)ccn12] | 318.33 | 2-(6-Methoxy-1-benzofuran-2-yl)-3-(methylamino)imidazo[1,2-a]pyridine-7-carbonitrile | Tr(MET-uHPLC-AB-101) = 3.09 min, (ES⁺) (M + H)⁺ 319 |
| 8 | 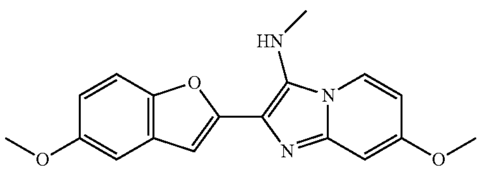 | 323.35 | 7-Methoxy-2-(5-methoxy-1-benzofuran-2-yl)-N-methylimidazo[1,2-a]pyridin-3-amine | Tr(MET-uHPLC-AB-101) = 1.92 min, (ES⁺) (M + H)⁺ 324 |
| 9 | 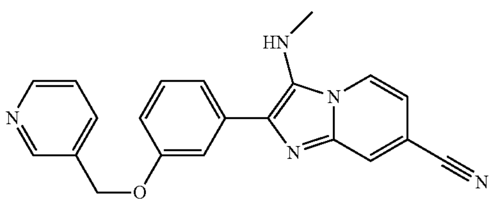 [SMILES: CNc1c(-c2cccc(OCc3cccnc3)c2)nc2cc(C#N)ccn12] | 355.39 | 3-(Methylamino)-2-[3-(pyridin-3-ylmethoxy)phenyl]imidazo[1,2-a]pyridine-7-carbonitrile | Tr(MET-uHPLC-AB-101) = 1.81 min, (ES⁺) (M + H)⁺ 356 |
| 10 | 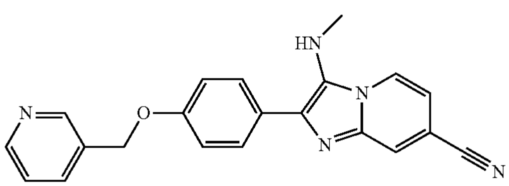 [SMILES: CNc1c(-c2ccc(OCc3cccnc3)cc2)nc2cc(C#N)ccn12] | 355.39 | 3-(Methylamino)-2-[4-(pyridin-3-ylmethoxy)phenyl]imidazo[1,2-a]pyridine-7-carbonitrile | Tr(MET-uHPLC-AB-101) = 1.64 min, (ES⁺) (M + H)⁺ 356 |
| 11 | 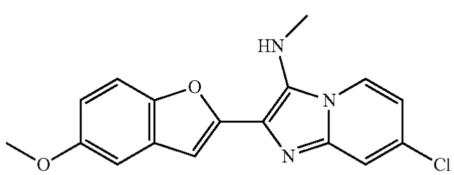 [SMILES: CNc1c(-c2cc3cc(OC)ccc3o2)nc2cc(Cl)ccn12] | 327.77 | 7-Chloro-2-(5-methoxy-1-benzofuran-2-yl)-N-methylimidazo[1,2-a]pyridin-3-amine | Tr(MET-uHPLC-AB-101) = 2.71 min, (ES⁺) (M + H)⁺ 328 |
| 12 | 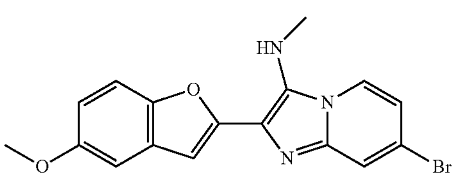 [SMILES: CNc1c(-c2cc3cc(OC)ccc3o2)nc2cc(Br)ccn12] | 372.22 | 7-Bromo-2-(5-methoxy-1-benzofuran-2-yl)-N-methylimidazo[1,2-a]pyridin-3-amine | Tr(MET-uHPLC-AB-101) = 2.84 min, (ES⁺) (M + H)⁺ 372/374 |
| 13 | 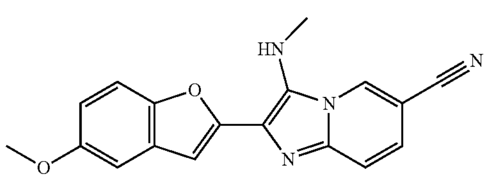 [SMILES: CNc1c(-c2cc3cc(OC)ccc3o2)nc2ccc(C#N)cn12] | 318.33 | 2-(5-Methoxy-1-benzofuran-2-yl)-3-(methylamino)imidazo[1,2-a]pyridine-6-carbonitrile | Tr(MET-uHPLC-AB-101) = 3.03 min, (ES⁺) (M + H)⁺ 319 |

TABLE 1-continued

| Ex. | Structure | Mol. Weight | IUPAC Name | LCMS data |
|---|---|---|---|---|
| 14 | 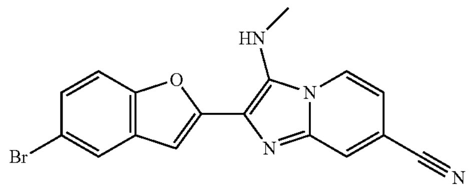 [SMILES: CNc1c(-c2cc3cc(Br)ccc3o2)nc2cc(C#N)ccn12] | 367.20 | 2-(5-Bromo-1-benzofuran-2-yl)-3-(methylamino)imidazo[1,2-a]pyridine-7-carbonitrile | Tr(MET-uHPLC-AB-101) = 3.62 min, (ES$^+$) (M + H)$^+$ 367/369 |
| 15 | 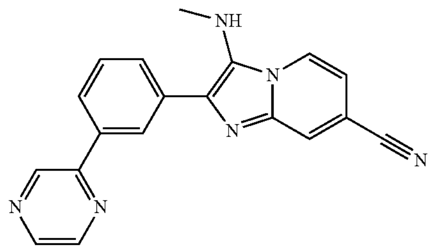 [SMILES: CNc1c(-c2cccc(-c3cnccn3)c2)nc2cc(C#N)ccn12] | 326.35 | 3-(Methylamino)-2-[3-(pyrazin-2-yl)phenyl]imidazo[1,2-a]pyridine-7-carbonitrile | Tr(MET-uHPLC-AB-101) = 2.42 min, (ES$^+$) (M + H)$^+$ 327 |
| 16 | 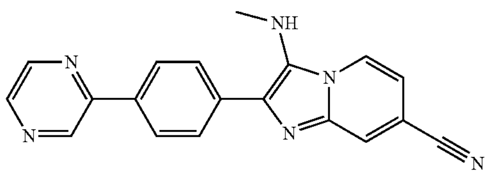 [SMILES: CNc1c(-c2ccc(-c3cnccn3)cc2)nc2cc(C#N)ccn12] | 326.35 | 3-(Methylamino)-2-[4-(pyrazin-2-yl)phenyl]imidazo[1,2-a]pyridine-7-carbonitrile | Tr(MET-uHPLC-AB-101) = 2.39 min, (ES$^+$) (M + H)$^+$ 327 |
| 17 | 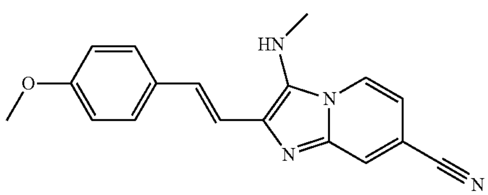 [SMILES: CNc1c(/C=C/c2ccc(OC)cc2)nc2cc(C#N)ccn12] | 304.35 | 2-[(E)-2-(4-Methoxyphenyl)ethenyl]-3-(methylamino)imidazo[1,2-a]pyridine-7-carbonitrile | Tr(MET-uHPLC-AB-101) = 2.51 min, (ES$^+$) (M + H)$^+$ 305 |
| 18 | 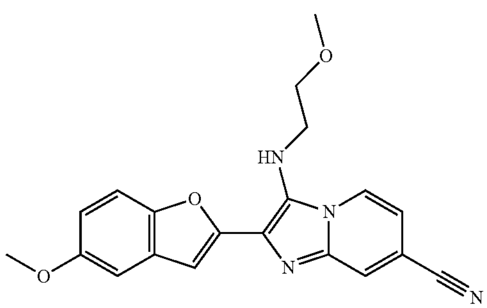 [SMILES: COCCNc1c(-c2cc3cc(OC)ccc3o2)nc2cc(C#N)ccn12] | 362.38 | 2-(5-Methoxy-1-benzofuran-2-yl)-3-[(2-methoxyethyl)amino]imidazo[1,2-a]pyridine-7-carbonitrile | Tr(MET-uHPLC-AB-101) = 3.18 min, (ES$^+$) (M + H)$^+$ 363, |
| 19 | 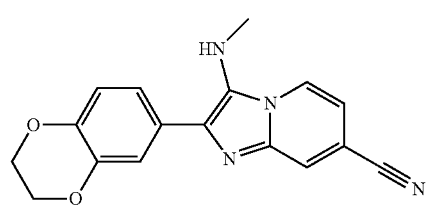 [SMILES: CNc1c(-c2ccc3c(c2)OCCO3)nc2cc(C#N)ccn12] | 306.32 | 2-(2,3-Dihydro-1,4-benzodioxin-6-yl)-3-(methylamino)imidazo[1,2-a]pyridine-7-carbonitrile | Tr(MET-uHPLC-AB-101) = 2.22 min, (ES$^+$) (M + H)$^+$ 307 |
| 20 | 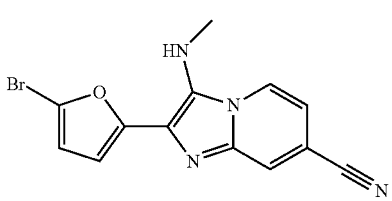 [SMILES: CNc1c(-c2ccc(Br)o2)nc2cc(C#N)ccn12] | 317.14 | 2-(5-Bromofuran-2-yl)-3-(methylamino)imidazo[1,2-a]pyridine-7-carbonitrile | Tr(MET-uHPLC-AB-101) = 2.85 min, (ES$^+$) (M + H)$^+$ 317/319 |

TABLE 1-continued

| Ex. | Structure | Mol. Weight | IUPAC Name | LCMS data |
|---|---|---|---|---|
| 21 | 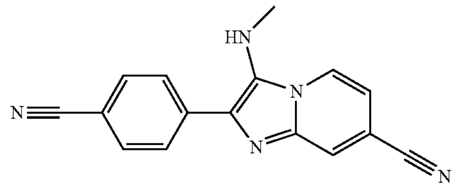 [SMILES: CNc1c(-c2ccc(C#N)cc2)nc2cc(C#N)ccn12] | 273.29 | 2-(4-Cyanophenyl)-3-(methylamino)imidazo[1,2-a]pyridine-7-carbonitrile | Tr(MET-uHPLC-AB-101) = 2.65 min, (ES+) (M + H)+ 274 |
| 22 | 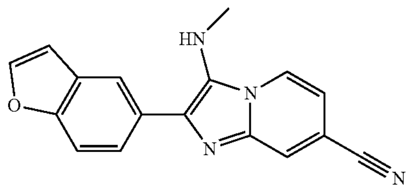 [SMILES: CNc1c(-c2ccc3occc3c2)nc2cc(C#N)ccn12] | 288.30 | 2-(1-Benzofuran-5-yl)-3-(methylamino)imidazo[1,2-a]pyridine-7-carbonitrile | Tr(MET-uHPLC-AB-101) = 2.48 min, (ES+) (M + H)+ 289 |
| 23 | 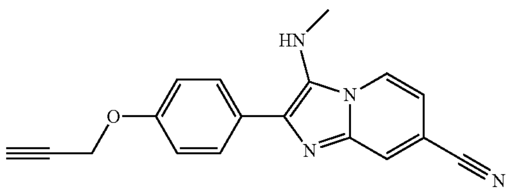 [SMILES: C#CCOc1ccc(-c2nc3cc(C#N)ccn3c2NC)cc1] | 302.33 | 3-(Methylamino)-2-[4-(prop-2-yn-1-yloxy)phenyl]imidazo[1,2-a]pyridine-7-carbonitrile | Tr(MET-uHPLC-AB-101) = 2.46 min, (ES+) (M + H)+ 303 |
| 24 | 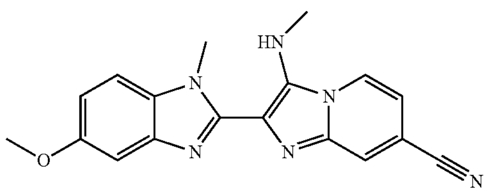 [SMILES: CNc1c(-c2nc3cc(OC)ccc3n2C)nc2cc(C#N)ccn12] | 332.36 | 2-(5-Methoxy-1-methyl-1H-1,3-benzodiazol-2-yl)-3-(methylamino)imidazo[1,2-a]pyridine-7-carbonitrile | Tr(MET-uHPLC-AB-101) = 1.96 min, (ES+) (M + H)+ 333 |
| 25 | 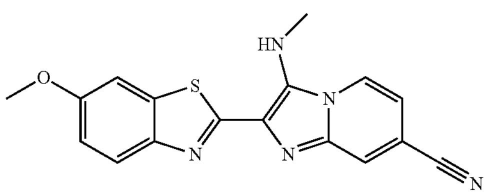 [SMILES: CNc1c(-c2nc3ccc(OC)cc3s2)nc2cc(C#N)ccn12] | 335.38 | 2-(6-Methoxy-1,3-benzothiazol-2-yl)-3-(methylamino)imidazo[1,2-a]pyridine-7-carbonitrile | Tr(MET-uHPLC-AB-101) = 3.52 min, (ES+) (M + H)+ 336 |
| 26 | 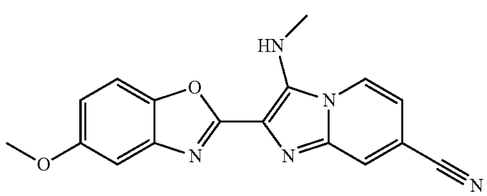 [SMILES: CNc1c(-c2nc3cc(OC)ccc3o2)nc2cc(C#N)ccn12] | 319.32 | 2-(5-Methoxy-1,3-benzoxazol-2-yl)-3-(methylamino)imidazo[1,2-a]pyridine-7-carbonitrile | Tr(MET-uHPLC-AB-101) = 2.98 min, (ES+) (M + H)+ 320 |
| 27 | 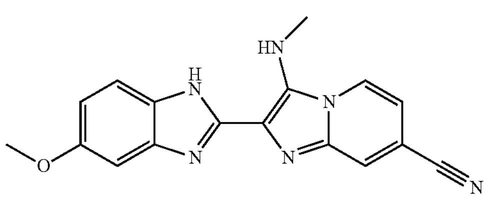 [SMILES: CNc1c(-c2nc3cc(OC)ccc3[nH]2)nc2cc(C#N)ccn12] | 318.33 | 2-(5-Methoxy-1H-1,3-benzodiazol-2-yl)-3-(methylamino)imidazo[1,2-a]pyridine-7-carbonitrile | Tr(MET-uHPLC-AB-101) = 1.87 min, (ES+) (M + H)+ 319 |
| 28 | 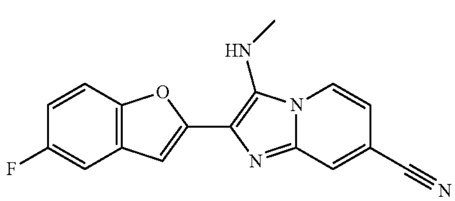 [SMILES: CNc1c(-c2cc3cc(F)ccc3o2)nc2cc(C#N)ccn12] | 306.29 | 2-(5-Fluoro-1-benzofuran-2-yl)-3-(methylamino)imidazo[1,2-a]pyridine-7-carbonitrile | Tr(MET-uHPLC-AB-101) = 3.22 min, (ES+) (M + H)+ 307 |

Method 2

Scheme for Method 2

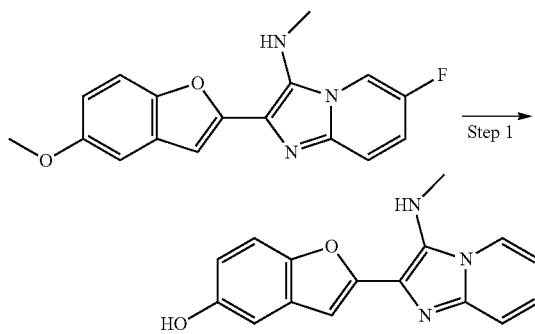

Step 1, Method 2: 2-[6-Fluoro-3-(methylamino) imidazo[1,2-a]pyridin-2-yl]-1-benzofuran-5-ol 6-Fluoro-2-(5-methoxy-1-benzofuran-2-yl)-N-methyl-imidazo[1,2-a]pyridin-3-amine (prepared according to Method 1, 0.25 g, 0.8 mmol) was dissolved in dichloromethane (10 mL). 1 M boron tribromide in dichloromethane (2.4 mL, 2.4 mmol) was added and the reaction stirred at room temperature for 1 hour. The reaction was quenched with methanol and the volatiles evaporated. The residue was dissolved in water and treated with saturated aqueous sodium bicarbonate. The resulting precipitate was filtered and recrystallized from 1:1 ethanol:water to give the title compound 0.08 g (33% yield) as a yellow powder.

Example 1, Method 2: 2-[6-Fluoro-3-(methylamino) imidazo[1,2-a]pyridin-2-yl]-1-benzofuran-5-ol $\delta_H$NMR (500 MHz, DMSO) 8.85 (br. s., 1H), 7.81 (d, J=5.83 Hz, 2H), 7.48 (d, J=8.83 Hz, 1H), 7.36 (s, 1H), 7.05 (d, J=2.36 Hz, 1H), 6.84 (dd, J=2.21, 8.83 Hz, 1H), 2.86 (s, 3H). Tr(METCR1416)=2.91 m=(ES$^+$) (M+H)$^+$ 298.

The following examples were prepared using Method 2 described above.

TABLE 2

| Ex. | Structure | Mol. Weight | IUPAC Name | LCMS data |
|---|---|---|---|---|
| 1 | 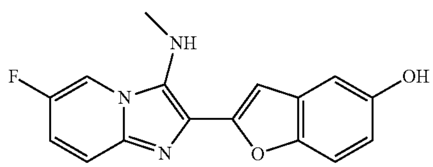 [SMILES: CNc1c(-c2cc3cc(O)ccc3o2)nc2ccc(F)cn12] | 297.29 | 2-[6-Fluoro-3-(methylamino)imidazo[1,2-a]pyridin-2-yl]-1-benzofuran-5-ol | Tr(METCR1416) = 2.91 min, (ES$^+$) (M + H)$^+$ 298 |
| 2 | 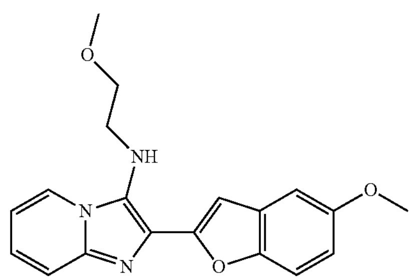 [SMILES: COCCNc1c(-c2cc3cc(OC)ccc3o2)nc2ccccn12] | 337.37 | 2-(5-Methoxy-1-benzofuran-2-yl)-N-(2-methoxyethyl)imidazo[1,2-a]pyridin-3-amine | Tr(METCR1416) = 2.96 min, (ES$^+$) (M + H)$^+$ 338 |
| 3 | 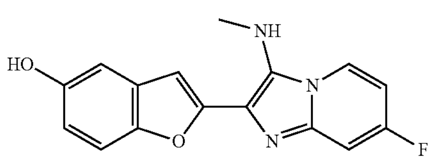 [SMILES: CNc1c(-c2cc3cc(O)ccc3o2)nc2cc(F)ccn12] | 297.29 | 2-[7-Fluoro-3-(methylamino)imidazo[1,2-a]pyridin-2-yl]-1-benzofuran-5-ol | Tr(METCR1416) = 2.69 min, (ES$^+$) (M + H)$^+$ 298 |
| 4 | 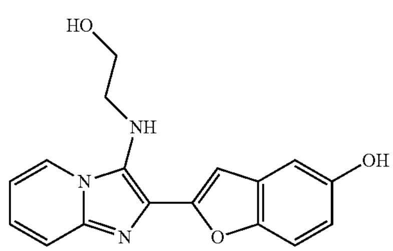 [SMILES: OCCNc1c(-c2cc3cc(O)ccc3o2)nc2ccccn12] | 309.32 | 2-{3-[(2-Hydroxyethyl)amino]imidazo[1,2-a]pyridin-2-yl}-1-benzofuran-5-ol | Tr(METCR1416) = 2.24 min, (ES$^+$) (M + H)$^+$ 310 |

TABLE 2-continued

| Ex. | Structure | Mol. Weight | IUPAC Name | LCMS data |
|---|---|---|---|---|
| 5 | 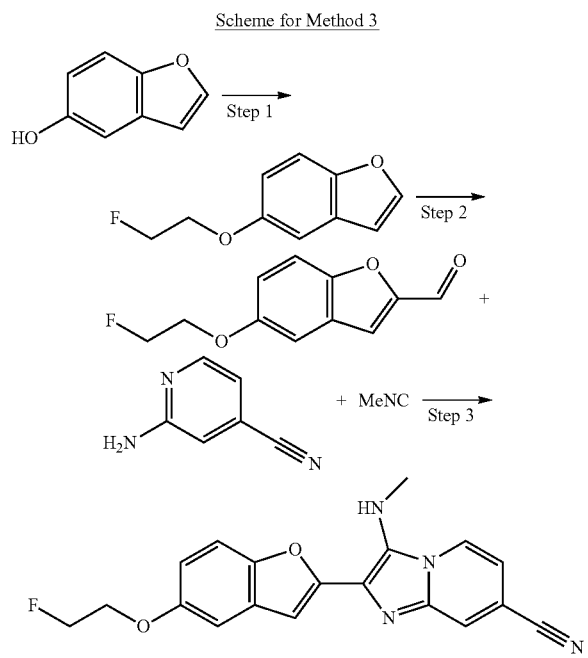 | 304.31 | 2-(5-Hydroxy-1-benzo-furan-2-yl)-3-(methylamino)imidazo[1,2-a]pyridine-7-carbonitrile | Tr(METCR1416) = 3.46 min, (ES+) (M + H)+ 305 |

Method 3

Scheme for Method 3

Step 1, Method 3: 5-(2-Fluoroethoxy)-1-benzofuran

To a stirred solution of 1-benzofuran-5-ol (275 mg, 2.05 mmol) in N,N-dimethylformamide (5 mL) was added 1-bromo-2-fluoroethane (306 µL, 4.10 mmol) and potassium carbonate (567 mg, 4.10 mmol) and the mixture was heated to 60° C. for 18 hours. A further portion of 1-bromo-2-fluoroethane (150 µL, 2.00 mmol) was added and the reaction was stirred at 60° C. for 4 hours. Further potassium carbonate (273 mg, 2.00 mmol) was added and the mixture was stirred at room temperature for 72 hours. Further potassium carbonate (273 mg, 2.00 mmol) was added and the mixture was heated to 80° C. for 5 hours. The mixture was cooled to room temperature and water (10 mL) was added. The mixture was then extracted with ethyl acetate (3×10 mL) and the organic extracts were combined, dried, concentrated and purified by FCC (silica, 10-90% dichloromethane in heptane) to give the title compound 343 mg (93% yield) as a colorless oil. $\delta_H$ (500 MHz, DMSO) 7.94 (d, J=2.1 Hz, 1H), 7.49 (d, J=8.9 Hz, 1H), 7.20 (d, J=2.5 Hz, 1H), 6.93 (dd, J=8.9, 2.5 Hz, 1H), 6.88 (s, 1H), 4.86-4.67 (m, 2H), 4.34-4.15 (m, 2H). Tr(METCR1278)=1.87 min, (ES+) (M+H)+181.

Step 2, Method 3: 5-(2-Fluoroethoxy)-1-benzofuran-2-carboxaldehyde

To a solution of 5-(2-fluoroethoxy)-1-benzofuran (250 mg, 1.39 mmol) in tetrahydrofuran (5 mL) cooled to −78° C. was added drop-wise 1.6 M n-butyllithium in hexanes (1.3 mL, 2.08 mmol). The resulting mixture was stirred for a further 10 minutes before anhydrous N,N-dimethylformamide (0.16 mL, 1.67 mmol) was added drop-wise. The reaction was allowed to warm to room temperature before water (5 mL) was added and the mixture extracted with ethyl acetate (2×10 mL), dried and concentrated. Purification by FCC (silica, 0-50% dichloromethane in heptane) gave the title compound 0.216 g (74% yield) as an orange-yellow solid. $\delta_H$NMR (500 MHz, DMSO) 9.83 (s, 1H), 7.91 (s, 1H), 7.67 (d, J=9.1 Hz, 1H), 7.40 (d, J=2.6 Hz, 1H), 7.23 (dd, J=9.1, 2.7 Hz, 1H), 4.89-4.60 (m, 2H), 4.44-4.07 (m, 2H). Tr(METCR1278)=1.73 min, (ES+) (M+H)+ 209.

Step 3, Method 3: 2-[5-(2-Fluoroethoxy)-1-benzofuran-2-yl]-3-(methylamino)imidazo[1,2-a]pyridine-7-carbonitrile To a solution of 5-(2-fluoroethoxy)-1-benzofuran-2-carbaldehyde (150 mg, 0.72 mmol) and 4-cyano-2-aminopyridine (86 mg, 0.72 mmol) in methanol (5 mL) was added methyl isocyanide (0.03 mL, 0.68 mmol), followed by acetic acid (0.5 mL). The mixture was stirred for 5 days, 1 M hydrochloric acid (5 mL) was added and the methanol carefully removed by rotary evaporation. The resulting mixture was neutralised with aqueous sodium bicarbonate, then extracted with dichloromethane (3×10 mL), dried, filtered and concentrated. Purification by FCC (silica, 2% methanol in dichloromethane) and recrystallisation from acetonitrile containing a minimum of DMSO, gave the title compound 30 mg (10% yield) as bright orange crystals.

Example 1, Method 3: 2-[5-(2-Fluoroethoxy)-1-benzofuran-2-yl]-3-(methylamino)imidazo[1,2-a]pyridine-7-carbonitrile $\delta_H$ NMR (250 MHz, DMSO) 8.41 (dd, J=0.88, 7.20 Hz, 1H), 8.23 (dd, J=0.93, 1.50 Hz, 1H), 7.56 (d, J=8.93 Hz, 1H), 7.42-7.11 (m, 3H), 6.95 (dd, J=2.61, 8.91 Hz, 1H), 5.46 (q, J=5.40 Hz, 1H), 5.06-4.54 (m, 2H), 4.50-4.08 (m, 2H), 2.88 (d, J=5.44 Hz, 3H). Tr(MET-uHPLC-AB-101)=3.11 min, (ES+) (M+H)+351.

The following example was prepared using Method 3 described above:

TABLE 3

| Ex. | Structure | Mol. Weight | IUPAC Name | LCMS data |
|---|---|---|---|---|
| 1 | 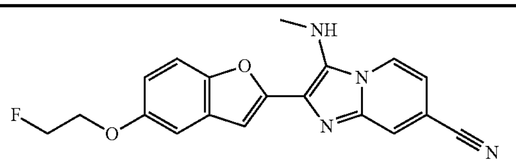 | 350.35 | 2-[5-(2-Fluoroethoxy)-1-benzofuran-2-yl]-3-(methylamino)imidazo[1,2-a]pyridine-7-carbonitrile | Tr(MET-uHPLC-AB-101) = 3.11 min, (ES+) (M + H)+ 351 |

Method 4

Scheme for Method 4

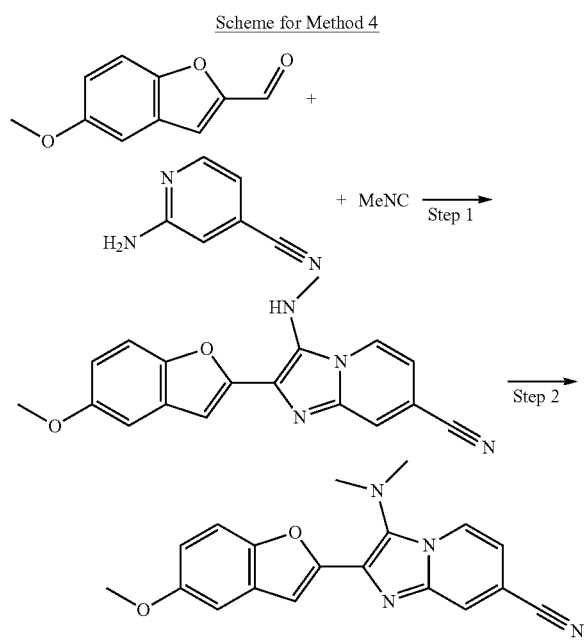

Step 1, Method 4: 2-(5-Methoxy-1-benzofuran-2-yl)-3-(methylamino)imidazo[1,2-a]pyridine-7-carbonitrile 5-Methoxy-1-benzofuran-2-carbaldehyde (300 mg, 1.70 mmol) and 2-aminoisonicotinonitrile (203 mg, 1.70 mmol) were dissolved in methanol (10 mL). Acetic acid (1 mL) and methyl isocyanide (76 μL, 1.70 mmol) were added and the mixture stirred at room temperature. After 3 days the reaction mixture was filtered and the yellow precipitate washed with methanol (3×10 mL) and dried under suction to give the title compound 256 mg (46% yield) as an orange powder. $\delta_H$ NMR (500 MHz, DMSO) 8.41 (d, J=7.15 Hz, 1H), 8.22 (br. s, 1H), 7.54 (d, J=8.89 Hz, 1H), 7.25 (s, 1H), 7.20 (d, J=2.56 Hz, 1H), 7.18 (dd, J=1.56, 7.15 Hz, 1H), 6.91 (dd, J=2.61, 8.89 Hz, 1H), 5.43 (q, J=5.44 Hz, 1H), 3.81 (s, 3H), 2.89 (d, J=5.46 Hz, 3H). Tr(METCR1278)=1.94 min, (ES+) (M+H)+ 319.

Step 2, Method 4: 3-(Dimethylamino)-2-(5-methoxy-1-benzofuran-2-yl)imidazo[1,2-a]pyridine-7-carbonitrile 2-(5-Methoxy-1-benzofuran-2-yl)-3-(methylamino)imidazo[1,2-a]pyridine-7-carbonitrile (98%, 30 mg, 0.09 mmol) was dissolved in N,N-dimethylformamide (1 mL) and treated with sodium hydride (60% in mineral oil, 6 mg, 0.14 mmol). The mixture was stirred at room temperature for 10 minutes then treated with methyl iodide (50 μL of a solution comprising 60 μL methyl iodide in 500 μL N,N-dimethylformamide, 0.09 mmol). The mixture was stirred at room temperature for 16 hours, then quenched by the addition of water (2 mL) and extracted with ethyl acetate (2×3 mL). Combined organic extracts were washed with water (1 mL) and brine (1 mL), then dried, filtered and concentrated. Purification by preparative HPLC (acetonitrile-water-0.1% formic acid) gave the title compound 8 mg (25% yield) as an orange powder.

Example 1, Method 4: 3-(Dimethylamino)-2-(5-methoxy-1-benzofuran-2-yl)imidazo[1,2-a]pyridine-7-carbonitrile $\delta_H$ NMR (500 MHz, DMSO) 8.44 (dd, J=0.73, 7.10 Hz, 1H), 8.29 (s, 1H), 7.59 (d, J=8.90 Hz, 1H), 7.29 (d, J=0.59 Hz, 1H), 7.26-7.22 (m, 2H), 6.94 (dd, J=2.62, 8.91 Hz, 1H), 3.81 (s, 3H), 2.94 (s, 6H). Tr(MET-uHPLC-AB-101)=3.63 min, (ES+) (M+H)+333.

The following example was prepared using Method 4 described above:

TABLE 4

| Ex. | Structure | Mol. Weight | IUPAC Name | LCMS data |
|---|---|---|---|---|
| 1 | 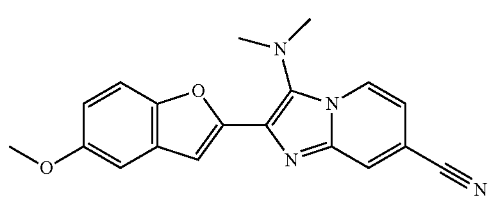 [SMILES: COc1ccc2oc(-c3nc4cc(C#N)ccn4c3N(C)C)cc2c1] | 332.36 | 3-(Dimethylamino)-2-(5-methoxy-1-benzofuran-2-yl)imidazo[1,2-a]pyridine-7-carbonitrile | Tr(MET-uHPLC-AB-101) = 3.63 min, (ES+) (M + H)+ 333 |

Method 5

Scheme for Method 5

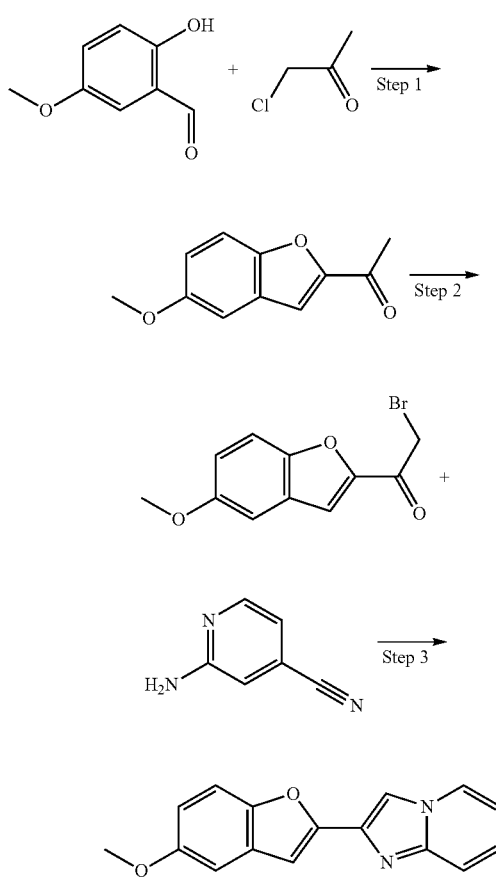

Step 1, Method 5:
1-(5-Methoxy-1-benzofuran-2-yl)ethan-1-one

2-Hydroxy-5-methoxybenzaldehyde (8.26 mL, 65.7 mmol) was added drop-wise to a suspension of potassium carbonate (10.9 g, 78.9 mmol) in acetone (200 mL). 1-Chloropropan-2-one (6.03 mL, 75.6 mmol) was added drop-wise over 5 minutes and the mixture heated to reflux for 3 hours. The reaction mixture was cooled to room temperature and filtered. The filter cake was washed with additional acetone (2×30 mL) and the filtrate concentrated. Purification by FCC (silica, 25-50% ethyl acetate in heptane) gave the title compound 11.6 g (90% yield) as a yellow powder. $^6$H NMR (500 MHz, DMSO) 7.78 (d, J=0.71 Hz, 1H), 7.61 (d, J=9.07 Hz, 1H), 7.28 (d, J=2.61 Hz, 1H), 7.13 (dd, J=2.66, 9.06 Hz, 1H), 3.81 (s, 3H), 2.54 (s, 3H). Tr(METCR1278)=1.75 min, (ES$^+$) (M+H)$^+$ 191.

Step 2, Method 5: 2-Bromo-1-(5-methoxy-1-benzofuran-2-yl)ethan-1-one 1-(5-Methoxy-1-benzofuran-2-yl)ethan-1-one (50 mg, 0.25 mmol) was dissolved in tetrahydrofuran (2 mL) and cooled to 0° C. N,N,N-trimethylanilinium tribromide (95 mg, 0.25 mmol) was added portion-wise over 2 minutes and the mixture stirred for 1 hour, warming slowly to room temperature. The reaction was quenched by the addition of saturated aqueous sodium bicarbonate (5 mL). The mixture was extracted with methyl tert-butyl ether (10 mL). The organic layer was separated and washed with brine (10 mL), then dried, filtered and concentrated to give the title compound 52 mg (62% yield) as a yellow gum. $\delta_H$ NMR (500 MHz, DMSO) 8.03-7.93 (m, 1H), 7.65 (d, J=9.09 Hz, 1H), 7.33 (d, J=2.60 Hz, 1H), 7.18 (dd, J=2.66, 9.08 Hz, 1H), 4.80 (s, 2H), 3.82 (s, 3H). Tr(METCR1278)=1.92 min, (ES$^+$) (M+H)$^+$269/271, 81%.

Step 3, Method 5: 2-(5-Methoxy-1-benzofuran-2-yl)imidazo[1,2-a]pyridine-7-carbonitrile 2-Bromo-1-(5-methoxy-1-benzofuran-2-yl)ethan-1-one (48 mg, 0.18 mmol) and 2-aminoisonicotinonitrile (21 mg, 0.18 mmol) were dissolved in acetone (5 mL) and stirred at room temperature for 16 hours. The reaction mixture was concentrated and the residue suspended in saturated aqueous sodium bicarbonate. The precipitate was collected by filtration and dried under suction. The crude product was triturated in 2:1 acetonitrile:DMSO (1 mL) and collected by filtration. The solid was washed with water (1 mL) and dried under suction to give the title compound 6 mg (12% yield) as an off-white powder.

Example 1, Method 5: 2-(5-Methoxy-1-benzofuran-2-yl)imidazo[1,2-a]pyridine-7-carbonitrile $\delta_H$ NMR (500 MHz, DMSO) 8.74 (d, J=6.96 Hz, 1H), 8.61 (s, 1H), 8.38 (s, 1H), 7.55 (d, J=8.88 Hz, 1H), 7.34 (s, 1H), 7.27 (d, J=7.00 Hz, 1H), 7.22 (d, J=2.38 Hz, 1H), 6.94 (dd, J=2.48, 8.92 Hz, 1H), 3.81 (s, 3H). Tr(MET-uHPLC-AB-101)=3.06 min, (ES$^+$) (M+H)$^+$290.

The following example was prepared using Method 5 described above:

TABLE 5

| Ex. | Structure | Mol. Weight | IUPAC Name | LCMS data |
|---|---|---|---|---|
| 1 | 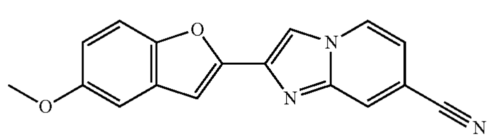 [SMILES: COc1ccc2oc(-c3cn4ccc(C#N)cc4n3)cc2c1] | 289.29 | 2-(5-Methoxy-1-benzofuran-2-yl)imidazo[1,2-a]pyridine-7-carbonitrile | Tr(MET-uHPLC-AB-101) = 3.06 min, (ES$^+$) (M + H)$^+$ 290 |

Method 6

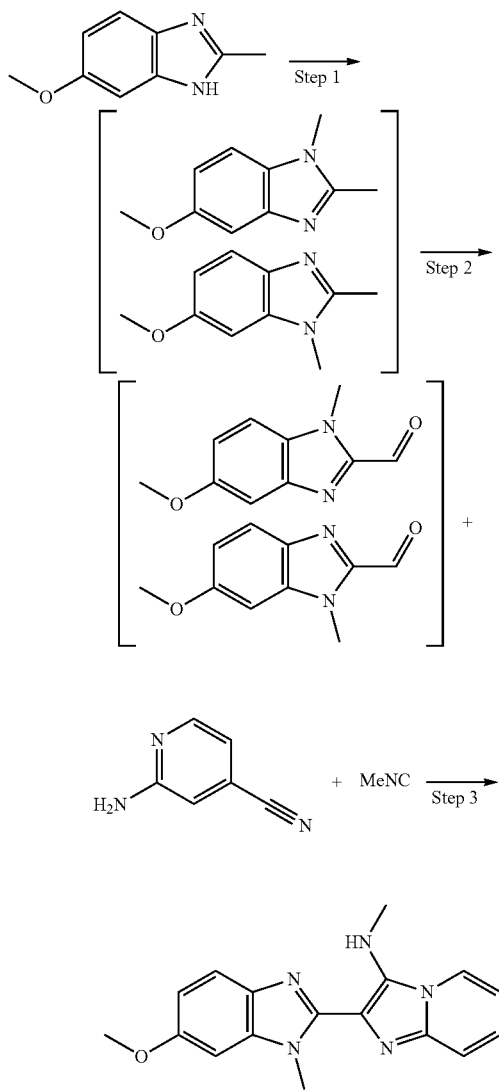

Step 1, Method 6: 5-Methoxy-1,2-dimethyl-1H-1,3-benzodiazole and 6-methoxy-1,2-dimethyl-1H-1,3-benzodiazole 5-Methoxy-2-methyl-1H-1,3-benzodiazole (500 mg, 3.08 mmol) was dissolved in anhydrous N,N-dimethylformamide (10 mL) and cooled to 0° C. The solution was treated with sodium hydride (60% in mineral oil, 185 mg, 4.62 mmol) and stirred at 0° C. for 20 minutes. Methyl iodide (191 µL, 3.08 mmol) was added, and the mixture was stirred at room temperature for 1 hour. The reaction mixture was quenched by the addition of water (10 mL) and extracted with ethyl acetate (2×15 mL). Combined organic extracts were washed with water (2×10 mL) and brine (2×10 mL), dried, filtered and concentrated. Purification by FCC (silica, 12-100% ethyl acetate in heptane then 10% methanol in dichloromethane) gave a 1:1 mixture of the title compounds 212 mg (40% yield) as a brown powder. $\delta_H$ NMR (500 MHz, chloroform) 7.55 (d, J=8.72 Hz, 1H), 7.19 (d, J=2.33 Hz, 1H), 7.15 (d, J=8.73 Hz, 1H), 6.89 (dd, J=2.37, 8.73 Hz, 1H), 6.86 (dd, J=2.39, 8.72 Hz, 1H), 6.75 (d, J=2.33 Hz, 1H), 3.87 (s, 3H), 3.85 (s, 3H), 3.69 (s, 3H), 3.67 (s, 3H), 2.58 (s, 3H), 2.57 (s, 3H). Tr(METCR1278)=0.77 min, (ES$^+$) (M+H)$^+$177.

Step 2, Method 6: 5-Methoxy-1-methyl-1H-1,3-benzodiazole-2-carbaldehyde and 6-methoxy-1-methyl-1H-1,3-benzodiazole-2-carbaldehyde A 1:1 mixture of 5-methoxy-1,2-dimethyl-1H-1,3-benzodiazole and 6-methoxy-1,2-dimethyl-1H-1,3-benzodiazole (212 mg, 1.20 mmol) and selenium dioxide (167 mg, 1.50 mmol) were suspended in dioxane (10 mL) in a sealed tube and heated to 110° C. for 3 hours. The reaction mixture was filtered through celite, eluting with dioxane until the filtrate ran colourless. The filtrate was concentrated to give a 1:1 mixture of the title compounds (186 mg, 81% yield) as a brown powder. $^6$H NMR (500 MHz, DMSO) 9.98 (s, 1H), 9.92 (s, 1H), 7.74 (d, J=8.97 Hz, 1H), 7.67 (d, J=9.02 Hz, 1H), 7.32 (d, J=2.34 Hz, 1H), 7.24 (d, J=2.35 Hz, 1H), 7.15 (dd, J=2.40, 9.02 Hz, 1H), 7.01 (dd, J=2.41, 8.97 Hz, 1H), 4.08 (s, 6H), 3.88 (s, 3H), 3.83 (s, 3H). Tr(METCR1278)=1.00 min, (ES$^+$) (M+H$_3$O)$^+$209.

Step 3, Method 6: 2-(6-Methoxy-1-methyl-1H-1,3-benzodiazol-2-yl)-3-(methylamino)imidazo[1,2-a]pyridine-7-carbonitrile A 1:1 mixture of 5-methoxy-1-methyl-1H-1,3-benzodiazole-2-carbaldehyde and 6-methoxy-1-methyl-1H-1,3-benzodiazole-2-carbaldehyde (186 mg, 0.98 mmol), 2-aminoisonicotinonitrile (116 mg, 0.98 mmol) and scandium triflate (24 mg, 0.05 mmol) were dissolved in trifluoroethanol (3 mL). Methyl isocyanide (44 µL, 0.98 mmol) was added and the mixture heated to 160° C. under microwave irradiation for 10 minutes. The reaction mixture was quenched with 1 M hydrochloric acid (2 mL) and concentrated. The residual aqueous suspension was neutralised with saturated aqueous sodium bicarbonate (until effervescence ceased) and extracted with ethyl acetate (2×10 mL). Combined organic extracts were washed with brine (10 mL), dried, filtered and concentrated. FCC (silica, 12-100% ethyl acetate in cyclohexane) gave a mixture of two regioisomers. Purification by preparative HPLC (acetonitrile-water-0.1% formic acid) gave the title compound 16 mg (25% yield) as an orange powder.

Example 1, Method 6: 2-(6-Methoxy-1-methyl-1H-1,3-benzodiazol-2-yl)-3-(methylamino)imidazo[1,2-a]pyridine-7-carbonitrile $\delta_H$ NMR (500 MHz, DMSO) 8.47 (d, J=7.23 Hz, 1H), 8.28 (s, 1H), 7.58 (d, J=8.74 Hz, 1H), 7.18 (d, J=2.29 Hz, 1H), 7.15 (dd, J=1.57, 7.21 Hz, 1H), 6.88 (dd, J=2.37, 8.74 Hz, 1H), 6.74 (d, J=5.77 Hz, 1H), 4.26 (s, 3H), 3.86 (s, 3H), 2.98 (d, J=5.79 Hz, 3H). Tr(MET-uHPLC-AB-101)=2.05 min, (ES$^+$) (M+H)$^+$333.

The following example was prepared using Method 6 described above:

TABLE 6

| Ex. | Structure | Mol. Weight | IUPAC Name | LCMS data |
|---|---|---|---|---|
| 1 | 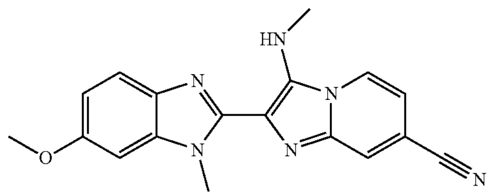 [SMILES: CNc1c(-c2nc3ccc(OC)cc3n2C)nc2cc(C#N)ccn12] | 332.36 | 2-(6-Methoxy-1-methyl-1H-1,3-benzodiazol-2-yl)-3-(methylamino)imidazo[1,2-a]pyridine-7-carbonitrile | Tr(MET-uHPLC-AB-101) = 2.05 min, (ES$^+$) (M + H)$^+$ 333 |

Method 7

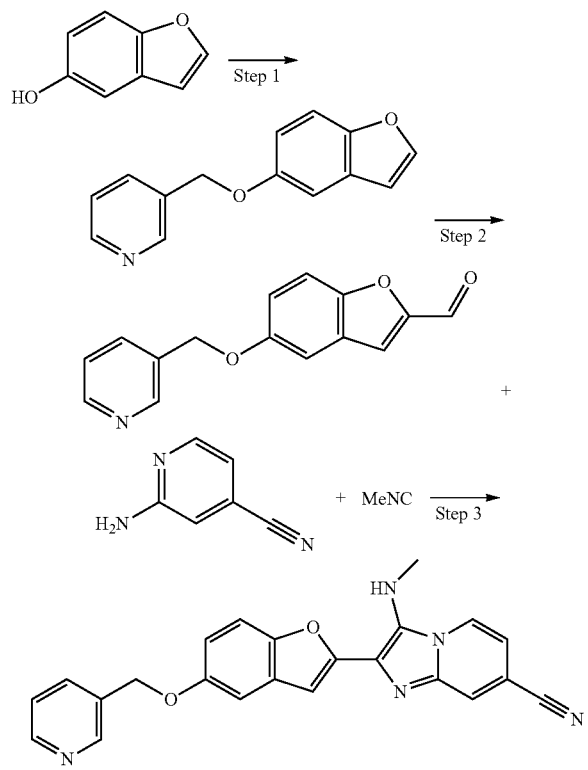

Scheme for Method 7

Step 1, Method 7:
3-[(1-Benzofuran-5-yloxy)methyl]pyridine

A solution of 1-benzofuran-5-ol in anhydrous N,N-dimethylformamide (2 mL) was added drop-wise over 5 minutes to a suspension of sodium hydride (60% in mineral oil, 168 mg, 4.21 mmol) in anhydrous N,N-dimethylformamide (2 mL) at 0° C. The mixture was stirred at 0° C. for 15 minutes before the addition of a solution of 3-(bromomethyl)pyridine hydrobromide (469 mg, 1.85 mmol) in anhydrous N,N-dimethylformamide (3 mL). The mixture was stirred at room temperature for 18 hours, then quenched by the addition of water (5 mL) and extracted with ethyl acetate (3×15 mL). Combined organic extracts were washed with brine (3×10 mL), dried, filtered and concentrated to give the title compound 376 mg (99% yield) as a brown solid. $\delta_H$ NMR (500 MHz, chloroform) 8.71 (d, J=1.76 Hz, 1H), 8.59 (dd, J=1.47, 4.83 Hz, 1H), 7.81 (d, J=7.83 Hz, 1H), 7.61 (d, J=2.14 Hz, 1H), 7.41 (d, J=8.91 Hz, 1H), 7.34 (dd, J=4.85, 7.79 Hz, 1H), 7.13 (d, J=2.56 Hz, 1H), 6.98 (dd, J=2.58, 8.91 Hz, 1H), 6.71 (dd, J=0.69, 2.06 Hz, 1H), 5.12 (s, 2H). Tr(METCR1278)=1.39 min, (ES$^+$) (M+H)$^+$226.

Step 2, Method 7: 5-(Pyridin-3-ylmethoxy)-1-benzofuran-2-carbaldehyde

3-[(1-Benzofuran-5-yloxy)methyl]pyridine (370 mg, 1.64 mmol) was dissolved in anhydrous tetrahydrofuran (8 mL) under nitrogen and cooled to −78° C. 1.6 M n-butyllithium in hexanes (1.54 mL, 2.46 mmol) was added drop-wise over 5 minutes and the solution stirred for 30 minutes. Anhydrous N,N-dimethylformamide (318 μL, 4.11 mmol) was then added and the mixture stirred for 18 hours. The reaction mixture was quenched by the addition of water (10 mL) and extracted with ethyl acetate (3×15 mL). The combined organic extracts were washed with brine (3×10 mL), then dried, filtered and concentrated. Purification by FCC (silica, 12-100% ethyl acetate in heptane) gave the title compound 52 mg (13% yield) as a white powder. $\delta_H$ NMR (500 MHz, DMSO) 9.83 (s, 1H), 8.71 (d, J=1.74 Hz, 1H), 8.56 (dd, J=1.54, 4.79 Hz, 1H), 7.96-7.85 (m, 2H), 7.68 (d, J=9.09 Hz, 1H), 7.50 (d, J=2.58 Hz, 1H), 7.44 (dd, J=4.80, 7.47 Hz, 1H), 7.29 (dd, J=2.65, 9.08 Hz, 1H), 5.22 (s, 2H). Tr(METCR1278)=1.29 min, (ES$^+$) (M+H)$^+$254.

Step 3, Method 7: 3-(Methylamino)-2-[5-(pyridin-3-ylmethoxy)-1-benzofuran-2-yl]imidazo[1,2-a]pyridine-7-carbonitrile 5-(Pyridin-3-ylmethoxy)-1-benzofuran-2-carbaldehyde (50 mg, 0.20 mmol) and 2-aminoisonicotinonitrile (24 mg, 0.20 mmol) were dissolved in methanol (2 mL). Acetic acid (0.2 mL) and methyl isocyanide (9 μL, 0.20 mmol) were added and the mixture stirred at room temperature for 16 hours. The reaction mixture was quenched with 1 M hydrochloric acid (2 mL) and concentrated. A precipitate formed, which was collected by filtration. The solid was washed with methyl tert-butyl ether (5 mL) and dried under suction. This powder was then partitioned between ethyl acetate and saturated aqueous sodium bicarbonate. The mixture was extracted with ethyl acetate (3×10 mL). The combined organic extracts were washed with brine (2×10 mL), dried, filtered and concentrated to give the title compound 8 mg (10% yield) as a yellow powder.

Example 1, Method 7: 3-(Methylamino)-2-[5-(pyridin-3-ylmethoxy)-1-benzofuran-2-yl]imidazo[1,2-a]pyridine-7-carbonitrile $\delta_H$ NMR (500 MHz, DMSO) 8.71 (d, J=1.71 Hz, 1H), 8.55 (dd, J=1.53, 4.79 Hz, 1H), 8.45-8.36 (m, 1H), 8.22 (s, 1H), 7.91 (d, J=7.89 Hz, 1H), 7.56 (d, J=8.89 Hz, 1H), 7.44 (dd, J=4.80, 7.63 Hz, 1H), 7.32 (d, J=2.55 Hz, 1H), 7.28-7.24 (m, 1H), 7.18 (dd, J=1.57, 7.15 Hz, 1H), 7.02 (dd, J=2.60, 8.89 Hz, 1H), 5.44 (q, J=5.44 Hz, 1H), 5.21 (s, 2H), 2.89 (d, J=5.46 Hz, 3H). Tr(MET-uHPLC-AB-101)=2.23 min, (ES$^+$) (M+H)$^+$396.

The following example was prepared using Method 7 described above:

TABLE 7

| Ex. | Structure | Mol. Weight | IUPAC Name | LCMS data |
|---|---|---|---|---|
| 1 | 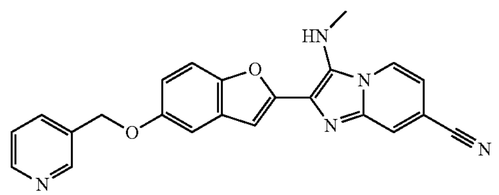 [SMILES: CNc1c(-c2cc3cc(OCc4cccnc4)ccc3o2)nc2cc(C#N)ccn12] | 395.41 | 3-(Methylamino)-2-[5-(pyridin-3-ylmethoxy)-1-benzofuran-2-yl]imidazo[1,2-a]pyridine-7-carbonitrile | Tr(MET-uHPLC-AB-101) = 2.23 min, (ES$^+$) (M + H)$^+$ 396 |

Method 8

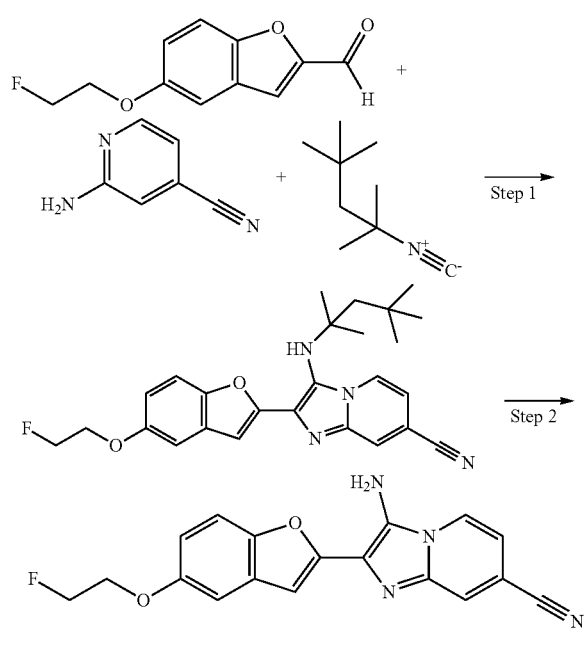

Scheme for Method 8

Step 1, Method 8: 2-[5-(2-Fluoroethoxy)-1-benzofuran-2-yl]-3-[(2,4,4-trimethylpentan-2-yl)amino]imidazo[1,2-a]pyridine-7-carbonitrile Prepared according to method 3, using 2,4,4-trimethylpentan-2-yl isocyanide. $\delta_H$ NMR (500 MHz, DMSO) 8.55 (d, J=7.2 Hz, 1H), 8.26 (s, 1H), 7.52 (d, J=8.9 Hz, 1H), 7.37 (s, 1H), 7.25 (d, J=2.4 Hz, 1H), 7.20 (d, J=7.2 Hz, 1H), 6.98 (dd, J=8.9, 2.5 Hz, 1H), 4.77 (dt, J=48.0, 3.7 Hz, 2H), 4.65 (s, 1H), 4.35-4.18 (m, 2H), 1.72 (s, 2H), 1.06 (s, 9H), 1.05 (s, 6H). Tr(METCR1278)=2.58 min, (ES$^+$) (M+H)$^+$ 449, 86%.

Step 2, Method 8: 3-Amino-2-[5-(2-fluoroethoxy)-1-benzofuran-2-yl]imidazo[1,2-a]pyridine-7-carbonitrile 2-[5-(2-Fluoroethoxy)-1-benzofuran-2-yl]-3-[(2,4,4-trimethylpentan-2-yl)amino]imidazo[1,2-a]pyridine-7-carbonitrile (86%, 1.50 g, 2.88 mmol) was dissolved in 4 M hydrochloric acid in dioxane (10 mL), instantly forming a yellow precipitate. Water (1 mL) was added and the reaction mixture was stirred at room temperature. After 30 minutes, the solid was partitioned between ethyl acetate and saturated aqueous sodium bicarbonate (1:1, ca. 100 mL) and extracted with further ethyl acetate (3×50 mL) and then dichloromethane (3×50 mL). The aqueous layer was filtered (GF/F paper), washed with methyl tert-butyl ether (10 mL) and dried under suction to give the title compound 264 mg (28% yield) as a yellow-orange powder.

Example 1, Method 8: 3-Amino-2-[5-(2-fluoroethoxy)-1-benzofuran-2-yl]imidazo[1,2-a]pyridine-7-carbonitrile $\delta_H$ NMR (500 MHz, DMSO) 8.34 (d, J=7.2 Hz, 1H), 8.10 (s, 1H), 7.54 (d, J=8.9 Hz, 1H), 7.19 (d, J=2.5 Hz, 1H), 7.16 (s, 1H), 7.10 (dd, J=7.2, 1.5 Hz, 1H), 6.92 (dd, J=8.9, 2.6 Hz, 1H), 6.41 (s, 2H), 4.85-4.70 (m, 2H), 4.34-4.22 (m, 2H). Tr(MET-uHPLC-AB-101)=2.78 min, (ES$^+$) (M+H)$^+$337.

The following examples were prepared using Method 8 described above.

TABLE 8

| Ex. | Structure | Mol. Weight | IUPAC Name | LCMS data |
|---|---|---|---|---|
| 1 | 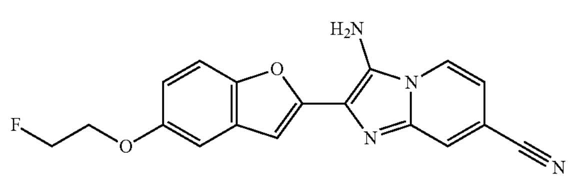 [SMILES: N#Cc1ccn2c(N)c(-c3cc4cc(OCCF)ccc4o3)nc2c1] | 336.32 | 3-Amino-2-[5-(2-fluoroethoxy)-1-benzofuran-2-yl]imidazo[1,2-a]pyridine-7-carbonitrile | Tr(MET-uHPLC-AB-101) = 2.78 min, (ES$^+$) (M + H)$^+$ 337 |

TABLE 8-continued

| Ex. | Structure | Mol. Weight | IUPAC Name | LCMS data |
|---|---|---|---|---|
| 2 | 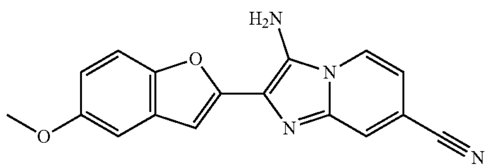 [SMILES: COc1ccc2oc(-c3nc4cc(C#N)ccn4c3N)cc2c1] | 304.30 | 3-Amino-2-(5-methoxy-1-benzofuran-2-yl)imidazo[1,2-a]pyridine-7-carbonitrile | Tr(MET-uHPLC-AB-101) = 2.75 min, (ES$^+$) (M + H)$^+$ 305 |

Method 9

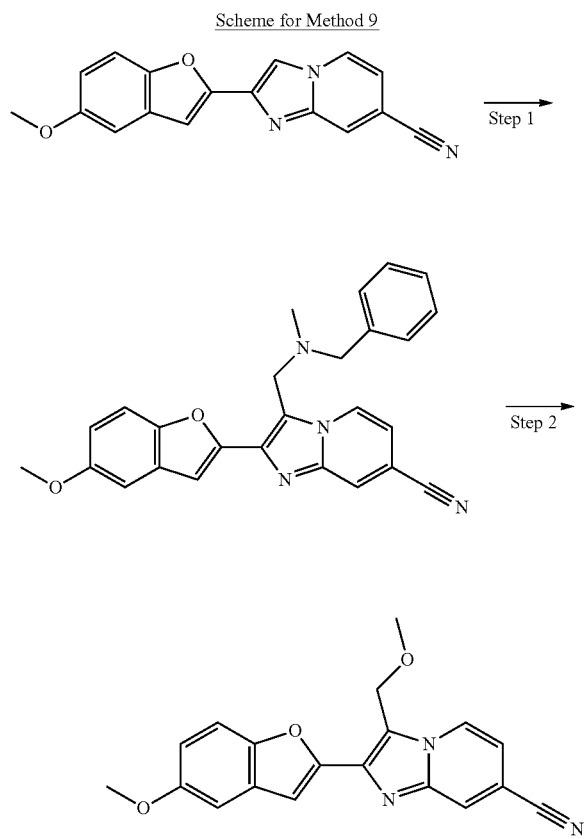

Scheme for Method 9

Step 1, Method 9: 3-{[Benzyl(methyl)amino]methyl}-2-(5-methoxy-1-benzofuran-2-yl)imidazo[1,2-a]pyridine-7-carbonitrile 2-(5-Methoxy-1-benzofuran-2-yl)imidazo[1,2-a]pyridine-7-carbonitrile (prepared according to Method 5, 50 mg, 0.17 mmol) was suspended in acetic acid (2 mL) and treated with 37% aqueous formaldehyde (13 µL, 0.17 mmol). N-Methyl-benzylamine (22 µL, 0.17 mmol) was added and the mixture heated to 70° C. for 18 hours. The reaction mixture was cooled to room temperature and basified with saturated aqueous sodium bicarbonate. The solution was extracted with ethyl acetate (2×10 mL), dried, filtered and concentrated. The material was dissolved in 2:1 acetonitrile: DMSO (2 mL); on standing a precipitate formed. The solid was collected by filtration, washed with methyl tert-butyl ether (2×5 mL) and dried under vacuum to give the title compound 20 mg (27% yield) as a yellow powder. $S_H$ NMR (500 MHz, DMSO) 8.64 (d, J=7.1 Hz, 1H), 8.37 (s, 1H), 7.57 (d, J=8.9 Hz, 1H), 7.37 (s, 1H), 7.34 (dd, J=7.1, 1.6 Hz, 1H), 7.30-7.17 (m, 6H), 6.96 (dd, J=8.9, 2.6 Hz, 1H), 4.36 (s, 2H), 3.82 (s, 3H), 3.61 (s, 2H), 2.12 (s, 3H). Tr(METCR1278)=1.60 min, (ES$^+$) (M+H)$^+$423.

Step 2, Method 9: 2-(5-Methoxy-1-benzofuran-2-yl)-3-(methoxymethyl)imidazo[1,2-a]pyridine-7-carbonitrile 3-{[Benzyl(methyl)amino]methyl}-2-(5-methoxy-1-benzofuran-2-yl)imidazo[1,2-a]pyridine-7-carbonitrile (20 mg, 0.05 mmol) was suspended in 1,2-dichloroethane (2 mL) and treated with 1-chloroethyl chloroformate (20 µL, 0.19 mmol). The mixture was heated to 55° C. for 18 hours. The reaction mixture was concentrated to dryness and the residue then dissolved in methanol (5 mL). The solution was heated to 50° C. for 90 minutes. The reaction mixture was concentrated to dryness to give a yellow powder. The powder was dissolved in methanol (1 mL) and the product precipitated with a single drop of water. The solid was collected by filtration and washed with methyl tert-butyl ether (5 mL), then dried under suction to give the title compound 7 mg (44% yield) as an off-white powder.

Example 1, Method 9: 2-(5-Methoxy-1-benzofuran-2-yl)-3-(methoxymethyl)imidazo[1,2-a]pyridine-7-carbonitrile $\delta_H$ NMR (500 MHz, DMSO) 8.70-8.57 (m, 1H), 8.50-8.35 (m, 1H), 7.60 (d, J=8.9 Hz, 1H), 7.39 (s, 1H), 7.34 (dd, J=7.1, 1.6 Hz, 1H), 7.24 (d, J=2.6 Hz, 1H), 6.96 (dd, J=8.9, 2.6 Hz, 1H), 5.20 (s, 2H), 3.81 (s, 3H), 3.36 (s, 3H). Tr(MET-uHPLC-AB-101)=3.26 mic, (ES$^+$) (M+H)$^+$ 334.

The following examples were prepared using Method 9 described above.

TABLE 9

| Ex. | Structure | Mol. Weight | IUPAC Name | LCMS data |
|---|---|---|---|---|
| 1 | 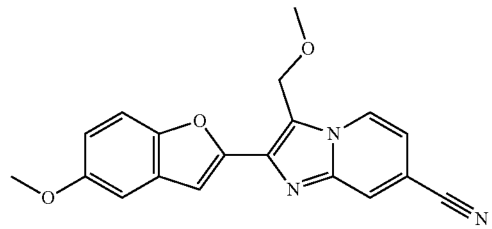 [SMILES: COCc1c(-c2cc3cc(OC)ccc3o2)nc2cc(C#N)ccn12] | 333.34 | 2-(5-Methoxy-1-benzofuran-2-yl)-3-(methoxymethyl)imidazo[1,2-a]pyridine-7-carbonitrile | Tr(MET-uHPLC-AB-101) = 3.26 min, (ES+) (M + H)+ 334 |
| 2 | 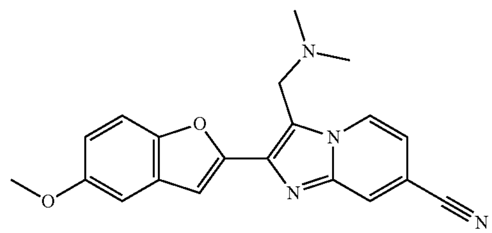 [SMILES: COc1ccc2oc(-c3nc4cc(C#N)ccn4c3CN(C)C)cc2c1] | 346.38 | 3-[(Dimethylamino)methyl]-2-(5-methoxy-1-benzofuran-2-yl)imidazo[1,2-a]pyridine-7-carbonitrile | Tr(MET-uHPLC-AB-101) = 1.65 min, (ES+) (M + H)+ 347 |

Method 10

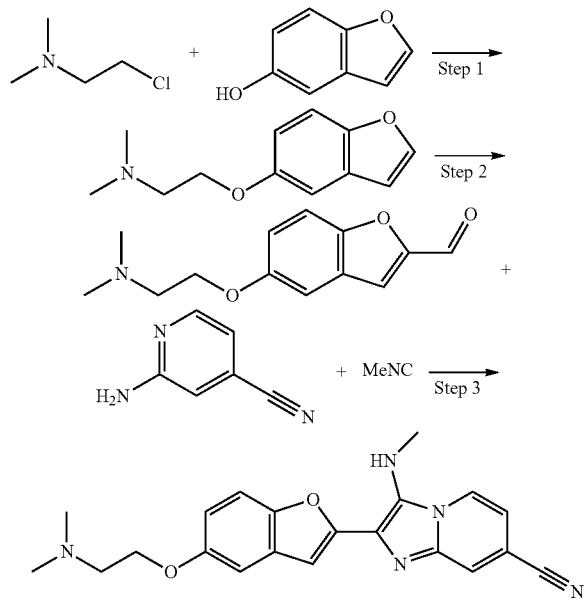

Scheme for Method 10

Step 1, Method 10: [2-(1-Benzofuran-5-yloxy)ethyl]dimethylamine

1-Benzofuran-5-ol (100 mg, 0.75 mmol) was dissolved in N,N-dimethylformamide (3 mL) and treated with potassium carbonate (309 mg, 2.24 mmol) and 2-chloro-N,N-dimethylethanamine hydrochloride (107 mg, 0.75 mmol). The reaction mixture was stirred at room temperature for 16 hours then heated to 60° C. for 5 hours. The reaction mixture was then concentrated and the residue was partitioned between ethyl acetate (10 mL) and water (10 mL). The layers were separated and the aqueous extracted with ethyl acetate (10 mL). The combined organic extracts were washed with brine (10 mL), dried, filtered and concentrated. The residue was purified using an SCX column to give the title compound 67 mg (44% yield) as an orange oil. $\delta_H$ NMR (500 MHz, chloroform) 7.59 (d, J=2.1 Hz, 1H), 7.38 (d, J=8.9 Hz, 1H), 7.07 (d, J=2.5 Hz, 1H), 6.93 (dd, J=8.9, 2.6 Hz, 1H), 6.70 (dd, J=2.1, 0.8 Hz, 1H), 4.10 (t, J=5.8 Hz, 2H), 2.76 (t, J=5.8 Hz, 2H), 2.36 (s, 6H). Tr(METCR1278)=0.91 min, (ES+) (M+H)+206.

Step 2, Method 10: 5-[2-(Dimethylamino)ethoxy]-1-benzofuran-2-carbaldehyde

[2-(1-Benzofuran-5-yloxy)ethyl]dimethylamine (65 mg, 0.32 mmol) was dissolved in anhydrous tetrahydrofuran (3 mL) under nitrogen and cooled to −78° C. 1.6 M n-Butyllithium in hexanes (300 μL, 0.48 mmol) was added dropwise over 2 minutes and the mixture stirred at −78° C. for 10 minutes. A light yellow precipitate formed. N,N-dimethylformamide (50 μL, 0.63 mmol) was added and the mixture allowed to warm to room temperature and stirred for 45 minutes. The reaction mixture was then quenched with water (10 mL) and extracted with ethyl acetate (3×10 mL). Combined organic extracts were washed with brine (10 mL), dried, filtered and concentrated to give the title compound 67 mg (46% yield) as a yellow oil. Tr(METCR1278)=0.98 min, (ES+) (M+H)+ 234.

Step 3, Method 10: 2-{5-[2-(Dimethylamino)ethoxy]-1-benzofuran-2-yl}-3-(methylamino)imidazo[1,2-a]pyridine-7-carbonitrile 5-[2-(Dimethylamino)ethoxy]-1-benzofuran-2-carbaldehyde (65 mg, 0.14 mmol) and 2-aminoisonicotinonitrile (17 mg, 0.14 mmol) were dissolved in methanol (2 mL). Acetic acid (0.2 mL) and methyl isocyanide (7 μL, 0.14 mmol) were added and the mixture stirred at room temperature for 22 hours. The reaction mixture was quenched with 1 M hydrochloric acid (1 mL) and stirred at room temperature for 10 minutes. The organic solvents were removed in vacuo and the aqueous neutralised with saturated aqueous sodium bicarbonate. The solution was extracted with ethyl acetate (3×10 mL). Combined organic extracts were washed with brine (10 mL), dried, filtered and concentrated. Purification by preparative HPLC (acetonitrile-water-0.1% formic acid) then by SCX column gave the title compound 5 mg (9% yield) as a yellow powder.

Example 1, Method 10: 2-{5-[2-(Dimethylamino)ethoxy]-1-benzofuran-2-yl}-3-(methylamino)imidazo[1,2-a]pyridine-7-carbonitrile $\delta_H$ NMR (500 MHz, DMSO) 8.41 (d, J=7.2 Hz, 1H), 8.22 (s, 1H), 7.53 (d, J=8.9 Hz, 1H), 7.25 (s, 1H), 7.21 (d, J=2.5 Hz, 1H), 7.18 (dd, J=7.2, 1.6 Hz, 1H), 6.91 (dd, J=8.9, 2.6 Hz, 1H), 5.44 (q, J=5.5 Hz, 1H), 4.09 (t, J=5.9 Hz, 2H), 2.88 (d, J=5.5 Hz, 3H), 2.69-2.61 (m, 2H), 2.24 (s, 6H). Tr(MET-uHPLC-AB-101)=1.69 min, (ES$^+$) (M+H)$^+$376.

The following example was prepared using Method 10 described above:

mmol) were dissolved in dichloromethane (2 mL). A solution of potassium hydroxide (404 mg, 7.2 mmol) in water (2 mL) was added, followed by tributylammonium chloride (20 mg, 0.07 mmol) and the mixture was heated to reflux for 16 hours. The reaction mixture was diluted with dichloromethane (10 mL) then washed with water (10 mL) and brine (10 mL). The dichloromethane layer was dried, filtered and concentrated. The residue was purified by FCC (silica, 20%-100% ethyl acetate in heptane) to give the title compound 52 mg (31% yield) as a colourless oil. $S_H$ NMR (500 MHz, chloroform) 10.02 (s, 1H), 8.70-8.59 (m, 1H), 8.59-8.53 (m, 1H), 7.88 (d, J=8.1 Hz, 2H), 7.73 (d, J=7.8 Hz, 1H), 7.53 (d, J=8.0 Hz, 2H), 7.32 (dd, J=7.8, 4.9 Hz, 1H), 4.66 (s, 2H), 4.62 (s, 2H). Tr(METCR1278)=1.09 min, (ES$^+$) (M+H)$^+$ 228.

TABLE 10

| Ex. | Structure | Mol. Weight | IUPAC Name | LCMS data |
| --- | --- | --- | --- | --- |
| 1 | 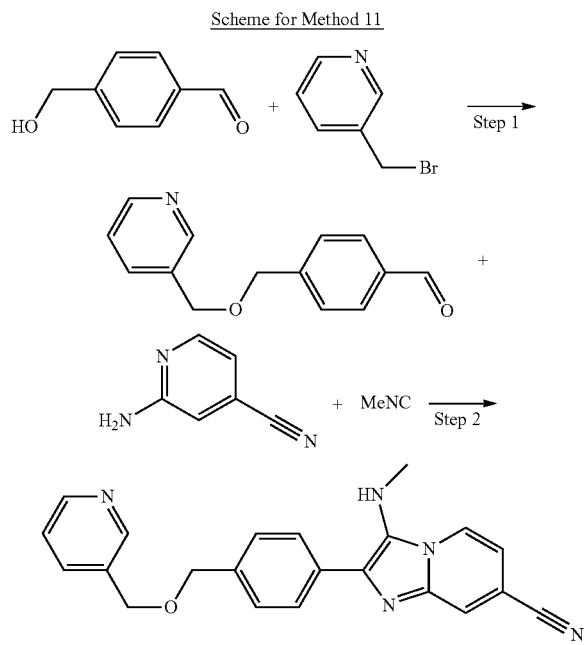 | 375.42 | 2-{5-[2-(Dimethylamino)ethoxy]-1-benzofuran-2-yl}-3-(methylamino)imidazo[1,2-a]pyridine-7-carbonitrile | Tr(MET-uHPLC-AB-101) = 1.69 min, (ES$^+$) (M + H)$^+$ 376 |

Method 11

Scheme for Method 11

Step 1, Method 11: 4-[(Pyridin-3-ylmethoxy)methyl]benzaldehyde 4-(Hydroxymethyl)benzaldehyde (100 mg, 0.72 mmol) and 3-(bromomethyl)pyridine hydrochloride (182 mg, 0.72

Step 2, Method 11: 3-(Methylamino)-2-{4-[(pyridin-3-ylmethoxy)methyl]phenyl}imidazo[1,2-a]pyridine-7-carbonitrile 4-[(Pyridin-3-ylmethoxy)methyl]benzaldehyde (50 mg, 0.22 mmol) and 2-aminoisonicotinonitrile (26 mg, 0.22 mmol) were dissolved in methanol (2 mL). Acetic acid (0.2 mL) and methyl isocyanide (12 µL, 0.22 mmol) were added and the mixture stirred at room temperature. The reaction mixture was quenched with 1 M hydrochloric acid (2 mL) and stirred at room temperature for 10 minutes. The organic solvents were removed in vacuo and the aqueous neutralised with saturated aqueous sodium bicarbonate. The solution was extracted with ethyl acetate (3×10 mL). The combined organic extracts were washed with brine (2×10 mL), dried, filtered and concentrated. Purification by preparative HPLC (acetonitrile-water-0.2% ammonium hydroxide) gave the title compound 28 mg (34% yield) as a yellow glass.

Example 1, Method 11: 3-(Methylamino)-2-{4-[(pyridin-3-ylmethoxy)methyl]phenyl}imidazo[1,2-a]pyridine-7-carbonitrile $\delta_H$ NMR (500 MHz, DMSO) 8.59 (d, J=1.5 Hz, 1H), 8.52 (dd, J=4.7, 1.4 Hz, 1H), 8.42 (d, J=7.1 Hz, 1H), 8.22 (s, 1H), 8.08 (d, J=8.2 Hz, 2H), 7.80 (d, J=7.8 Hz, 1H), 7.47 (d, J=8.2 Hz, 2H), 7.41 (dd, J=7.7, 4.8 Hz, 1H), 7.18 (dd, J=7.1, 1.5 Hz, 1H), 5.13 (q, J=5.4 Hz, 1H), 4.61 (s, 4H), 2.72 (d, J=5.4 Hz, 3H). Tr(MET-uHPLC-AB-101)=1.65 min, (ES$^+$) (M+H)$^+$370.

The following examples were prepared using Method 11 described above:

TABLE 11

| Ex. | Structure | Mol. Weight | IUPAC Name | LCMS data |
|---|---|---|---|---|
| 1 | 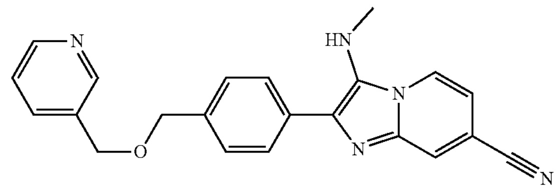 [SMILES: CNc1c(-c2ccc(COCc3cccnc3)cc2)nc2cc(C#N)ccn12] | 369.42 | 3-(Methylamino)-2-{4-[(pyridin-3-ylmethoxy)methyl]phenyl}imidazo[1,2-a]pyridine-7-carbonitrile | Tr(MET-uHPLC-AB-101) = 1.65 min, (ES⁺) (M + H)⁺ 370 |
| 2 | 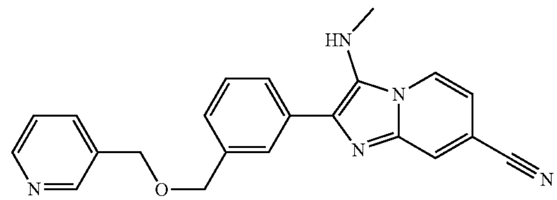 [SMILES: CNc1c(-c2cccc(COCc3cccnc3)c2)nc2cc(C#N)ccn12] | 369.42 | 3-(Methylamino)-2-{3-[(pyridin-3-ylmethoxy)methyl]phenyl}imidazo[1,2-a]pyridine-7-carbonitrile | Tr(MET-uHPLC-AB-101) = 1.72 min, (ES⁺) (M + H)⁺ 370 |

Method 12

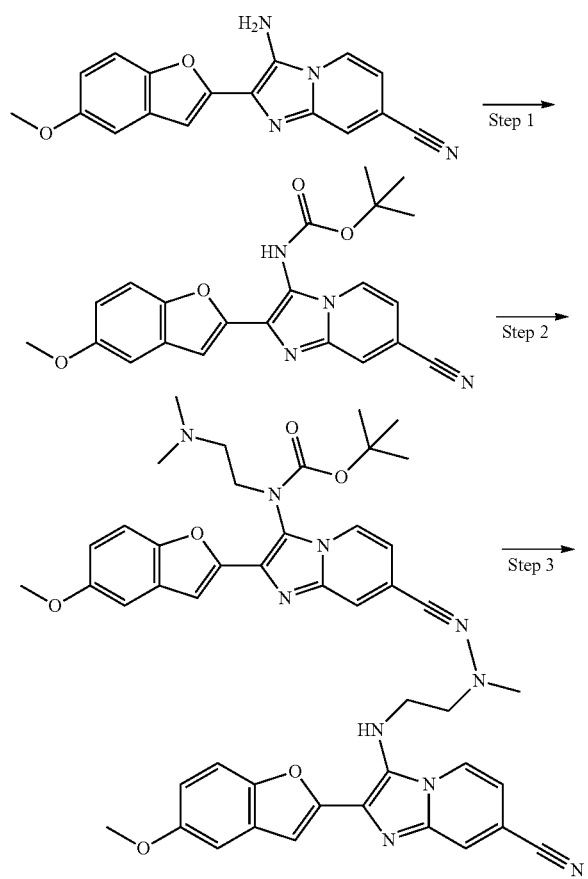

Scheme for Method 12

Step 1, Method 12: tert-Butyl N-[7-cyano-2-(5-methoxy-1-benzofuran-2-yl)imidazo[1,2-a]pyridin-3-yl]carbamate 3-Amino-2-(5-methoxy-1-benzofuran-2-yl)imidazo[1,2-a]pyridine-7-carbonitrile hydrochloride (prepared according to Method 8, 800 mg, 2.21 mmol) was suspended in anhydrous tetrahydrofuran (10 mL) under nitrogen. Triethylamine (308 μL, 2.21 mmol), Di-tert-butyl dicarbonate (963 mg, 4.41 mmol) and N,N-dimethylaminopyridine (27 mg, 0.22 mmol) were added and the mixture stirred at 60° C. for 18 hours. The reaction mixture was treated with additional triethylamine (308 μL, 2.21 mmol) and di-tert-butyl dicarbonate (963 mg, 4.41 mmol) and heated for 22 hours. Additional di-tert-butyl dicarbonate (963 mg, 4.41 mmol) was added and the mixture heated for 68 hours. Additional di-tert-butyl dicarbonate (963 mg, 4.41 mmol) and N,N-dimethylaminopyridine (50 mg) were added and the mixture heated for 2 hours. Additional di-tert-butyl dicarbonate (963 mg, 4.41 mmol) was added and the mixture heated for 2 hours. The reaction mixture was concentrated then dissolved in acetonitrile (20 mL) and treated with lithium iodide (590 mg, 4.41 mmol), heated to 70° C. and stirred at this temperature for 1 hour. The mixture was cooled to room temperature and concentrated. Purification by FCC (silica, 12%-100% ethyl acetate in heptane) gave the title compound 399 mg (33% yield) as an orange powder. ⁶H NMR (250 MHz, DMSO) 9.15 (s, 1H), 8.27 (dd, J=8.3, 1.3 Hz, 2H), 7.47 (d, J=8.9 Hz, 1H), 7.31-7.20 (m, 3H), 6.96 (dd, J=8.9, 2.6 Hz, 1H), 3.84 (s, 3H), 1.45 (s, 9H). Tr(METCR1278)=2.00 min, (ES⁺) (M+H)⁺405, 78%.

Step 2, Method 12: tert-Butyl N-[7-cyano-2-(5-methoxy-1-benzofuran-2-yl)imidazo[1,2-a]pyridin-3-yl]-N-[2-(dimethylamino)ethyl]carbamate tert-Butyl N-[7-cyano-2-(5-methoxy-1-benzofuran-2-yl)imidazo[1,2-a]pyridin-3-yl]carbamate (207 mg, 0.51 mmol) was dissolved in anhydrous N,N-dimethylformamide (10 mL). Sodium hydride (60% in mineral oil, 51 mg, 1.3 mmol) was added and the mixture stirred at room temperature for 10 minutes. 2-Chloro-N,N-dimethylethanamine hydrochloride (73 mg, 0.51 mmol) was added and the mixture stirred at room temperature for 18 hours. Additional sodium hydride (60% in mineral oil, 51 mg, 1.3 mmol) and 2-chloro-N,N-dimethylethanamine hydrochloride (73 mg, 0.51 mmol) were added and the mixture stirred at room temperature for 24 hours. Additional sodium hydride (60% in mineral oil, 51 mg, 1.3 mmol) and 2-chloro-N,N-dimethylethanamine hydrochloride (73 mg, 0.51 mmol) were added and the mixture stirred at room temperature for 18 hours.

The reaction mixture was quenched by the addition of water (10 mL) then extracted with ethyl acetate (3×15 mL). Combined organic extracts were washed with brine (5×10 mL), dried, filtered and concentrated. Purification by FCC (silica, ethyl acetate then 5-10% methanol in ethyl acetate) gave the title compound 25 mg (9% yield) as an orange oil. Tr(METCR1278)=1.59 min, (ES$^+$) (M+H)$^+$476, 83%.

Step 3, Method 12: 3-{[2-(Dimethylamino)ethyl] amino}-2-(5-methoxy-1-benzofuran-2-yl)imidazo[1, 2-a]pyridine-7-carbonitrile tert-Butyl-N-[7-cyano-2-(5-methoxy-1-benzofuran-2-yl) imidazo[1,2-a]pyridin-3-yl]-N-[2-(dimethylamino)ethyl] carbamate (25 mg, 0.04 mmol) was dissolved in 4 M hydrochloric acid in dioxane (1 mL) and stirred at room temperature for 1 hour. Additional 4 M hydrochloric acid in dioxane (1 mL) was added and the mixture stirred for 4 hours. The reaction mixture was then concentrated and re-treated with 4 M hydrochloric acid in dioxane (1 mL) and water (0.3 mL). The reaction mixture was concentrated and purified by preparative HPLC (acetonitrile-water-0.2% ammonium hydroxide) to give the title compound 6 mg (37% yield) as a yellow powder.

Example 1, Method 12: 3-{[2-(Dimethylamino) ethyl]amino}-2-(5-methoxy-1-benzofuran-2-yl)imidazo[1,2-a]pyridine-7-carbonitrile $\delta_H$ NMR (500 MHz, DMSO) 8.53-8.41 (m, 1H), 8.22 (s, 1H), 7.51 (d, J=8.9 Hz, 1H), 7.32-7.25 (m, 1H), 7.23-7.13 (m, 2H), 6.92 (dd, J=8.9, 2.6 Hz, 1H), 5.38 (t, J=6.2 Hz, 1H), 3.81 (s, 3H), 3.22 (q, J=6.1 Hz, 2H), 2.42 (t, J=6.1 Hz, 2H), 2.15 (s, 6H). Tr(MET-uHPLC-AB-101)=1.71 min, (ES$^+$) (M+H)$^+$376.

The following example was prepared using Method 12 described above:

Step 1, Method 13: tert-Butyl 4H,5H,6H,7H-furo[3,2-c]pyridine-5-carboxylate 4,5,6,7-Tetrahydrofuro[3,2-c]pyridine (425 mg, 3.45 mmol) was dissolved in dichloromethane (10 mL) and cooled to 0° C. Di tert-butyl dicarbonate (753 mg, 3.45 mmol) was added and the mixture stirred, allowing warming to room temperature over 16 hours. The reaction mixture was concentrated to give the title compound 801 mg (quantitative yield) as an orange syrup. $\delta_H$ NMR (500 MHz,

TABLE 12

| Ex. | Structure | Mol. Weight | IUPAC Name | LCMS data |
|---|---|---|---|---|
| 1 | 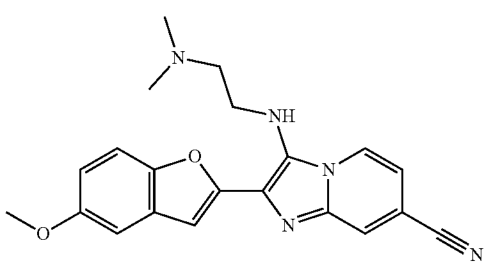 [SMILES: COc1ccc2oc(-c3nc4cc(C#N)ccn4c3NCCN(C)C)cc2c1] | 375.42 | 3-{[2-(Dimethylamino) ethyl]amino}-2-(5-methoxy-1-benzofuran-2-yl)imidazo[1,2-a]pyridine-7-carbonitrile | Tr(MET-uHPLC-AB-101) = 1.71 min, (ES$^+$) (M + H)$^+$ 376 |

Method 13

Scheme for Method 13

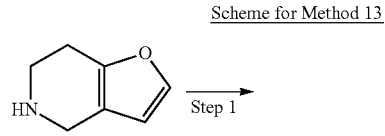

chloroform) 7.29 (s, 1H), 6.23 (d, J=1.6 Hz, 1H), 4.34 (s, 2H), 3.72 (s, 2H), 2.69 (s, 2H), 1.48 (s, 9H). Tr(METCR1278)=1.99 min, (ES$^+$) (M-Boc+H)$^+$124.

Step 2, Method 13: tert-Butyl 2-formyl-4H,5H,6H, 7H-furo[3,2-c]pyridine-5-carboxylate tert-Butyl 4H,5H,6H,7H-furo[3,2-c]pyridine-5-carboxylate (50 mg, 0.22 mmol) was dissolved in anhydrous tetrahydrofuran (3 mL) under nitrogen and cooled to −78° C. 1.5 M tert-butyllithium in pentane (0.30 mL, 0.45 mmol) was added drop-wise over 2 minutes and the mixture stirred at −78° C. for 15 minutes. Anhydrous N,N-dimethylformamide (52 uL, 0.67 mmol) was added and the mixture stirred at −78° C. The reaction mixture was quenched with water (5 mL) and extracted with ethyl acetate (3×10 mL). The combined organic extracts were washed with brine (10 mL), dried, filtered and concentrated. Purification by FCC (silica, 25% ethyl acetate in heptane) gave the title compound 26 mg (37% yield) as a colourless oil. $^6$H NMR (500 MHz, chloroform) 9.53 (s, 1H), 7.07 (s, 1H), 4.40 (br. s, 2H), 3.76 (br. s, 2H), 2.80 (br. s, 2H), 1.47 (s, 9H).

Step 3, Method 13: tert-Butyl 2-[7-cyano-3-(methylamino)imidazo[1,2-a]pyridin-2-yl]-4H,5H,6H,7H-furo[3,2-c]pyridine-5-carboxylate tert-Butyl 2-formyl-4H,5H,6H,7H-furo[3,2-c]pyridine-5-carboxylate (26 mg, 0.1 mmol) and 2-aminoisonicotinonitrile (10 mg, 0.08 mmol) were dissolved in methanol (1 mL). Acetic acid (0.1 mL) and methyl isocyanide (10 μL, 0.19 mmol) were added and the mixture stirred at room temperature for 72 hours. The reaction mixture was quenched with 1 M hydrochloric acid (2 mL) and stirred at room temperature for 30 minutes. The organic solvents were removed in vacuo and the aqueous neutralised with saturated aqueous sodium bicarbonate. The solution was extracted with ethyl acetate (3×10 mL). The combined organic extracts were washed with brine (2×10 mL), dried, filtered and concentrated. The residue was purified by preparative HPLC (acetonitrile-water-0.1% formic acid) to give the title compound 6 mg (18% yield) as a yellow powder.

Example 1, Method 13: tert-Butyl 2-[7-cyano-3-(methylamino)imidazo[1,2-a]pyridin-2-yl]-4H,5H,6H,7H-furo[3,2-c]pyridine-5-carboxylate $δ_H$ NMR (500 MHz, DMSO) 8.38-8.29 (m, 1H), 8.14 (s, 1H), 7.15 (dd, J=7.1, 1.6 Hz, 1H), 6.82 (s, 1H), 5.13 (q, J=5.4 Hz, 1H), 4.34 (s, 2H), 3.70 (t, J=5.7 Hz, 2H), 2.78 (d, J=5.5 Hz, 3H), 2.75 (t, J=5.6 Hz, 2H), 1.43 (s, 9H). Tr(MET-uHPLC-AB-101)=3.29 min, (ES$^+$) (M+H)$^+$394.

The following example was prepared using Method 13 described above:

Method 14

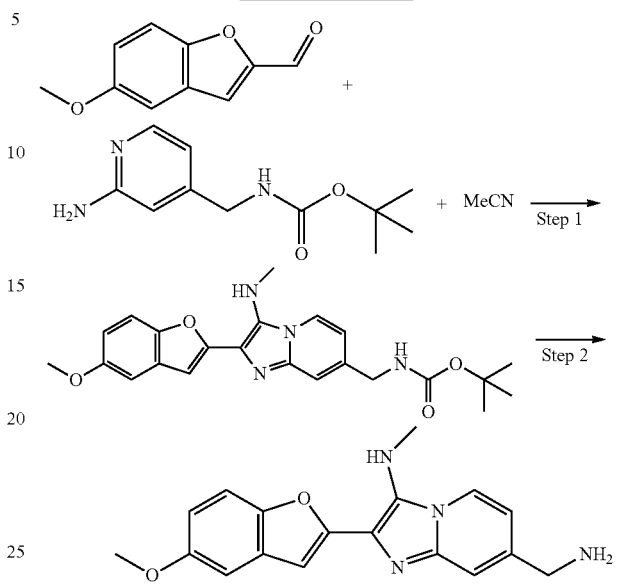

Scheme for Method 14

Step 1, Method 14: tert-Butyl N-{[2-(5-methoxy-1-benzofuran-2-yl)-3-(methylamino)imidazo[1,2-a]pyridin-7-yl]methyl}carbamate 5-Methoxy-1-benzofuran-2-carbaldehyde (200 mg, 1.13 mmol) and tert-butyl N-[(2-aminopyridin-4-yl)methyl]carbamate (253 mg, 1.14 mmol) were suspended in methanol (5 mL). Acetic acid (0.5 mL) and methyl isocyanide (59 μL, 1.13 mmol) were added and the mixture stirred at room temperature for 18 hours. The reaction mixture was quenched with 1 M hydrochloric acid (2 mL) and stirred at room temperature for 10 minutes. The organic solvents were removed in vacuo and the aqueous neutralised with saturated aqueous sodium bicarbonate. The solution was extracted with ethyl acetate (3×10 mL). The combined organic extracts were washed with brine (2×10 mL), dried, filtered and concentrated. Purification by FCC (silica, 25-100% ethyl acetate in heptane) gave the title compound 153 mg (31% yield) as a yellow powder. Tr(MET-uHPLC-AB-101)=2.38 min, (ES$^+$) (M+H)$^+$423, 92%.

TABLE 13

| Ex. | Structure | Mol. Weight | IUPAC Name | LCMS data |
| --- | --- | --- | --- | --- |
| 1 | 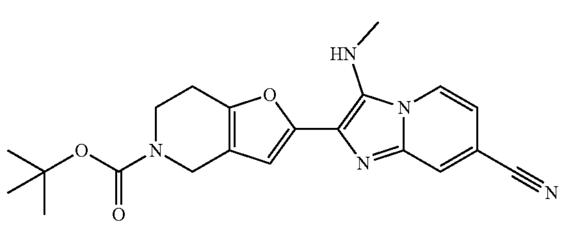 [SMILES: CNc1c(-c2cc3c(o2)CCN(C(=O)OC(C)(C)C)C3)nc2cc(C#N)ccn12] | 393.44 | tert-Butyl 2-[7-cyano-3-(methylamino)imidazo[1,2-a]pyridin-2-yl]-4H,5H,6H,7H-furo[3,2-c]pyridine-5-carboxylate | Tr(MET-uHPLC-AB-101) = 3.29 min, (ES$^+$) (M + H)$^+$ 394 |

Step 2, Method 14: 7-(Aminomethyl)-2-(5-methoxy-1-benzofuran-2-yl)-N-methylimidazo[1,2-a]pyridin-3-amine tert-Butyl-N-{[2-(5-methoxy-1-benzofuran-2-yl)-3-(methylamino)imidazo[1,2-a]pyridin-7-yl]methyl}carbamate (159 mg, 0.35 mmol) was dissolved in 4 M hydrochloric acid in dioxane (2 mL) and treated with water (0.2 mL). The mixture was stirred at room temperature for 1.5 hours. The reaction mixture was then concentrated and the residue was twice re-suspended in methyl tert-butyl ether (10 mL) and concentrated. Purification by preparative HPLC (acetonitrile-water) followed by SCX gave the title compound 9.9 mg (11% yield) as an orange solid.

Example 1, Method 14: 7-(Aminomethyl)-2-(5-methoxy-1-benzofuran-2-yl)-N-methylimidazo[1,2-a]pyridin-3-amine $\delta_H$ NMR (500 MHz, DMSO) 8.19 (d, J=7.0 Hz, 1H), 7.50 (d, J=8.9 Hz, 1H), 7.38 (s, 1H), 7.16 (d, J=2.6 Hz, 1H), 7.15 (s, 1H), 6.91 (dd, J=7.1, 1.4 Hz, 1H), 6.87 (dd, J=8.9, 2.6 Hz, 1H), 4.93 (q, J=5.5 Hz, 1H), 3.80 (s, 3H), 3.76 (s, 2H), 2.81 (d, J=5.5 Hz, 3H). Tr(MET-uHPLC-AB-101)=1.32 min, (ES$^+$) (M+H)$^+$323.

The following example was prepared using Method 14 described above:

TABLE 14

| Ex. | Structure | Mol. Weight | IUPAC Name | LCMS data |
|---|---|---|---|---|
| 1 | 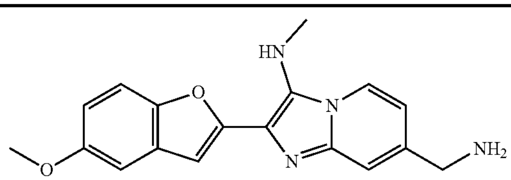 | 322.36 | 7-(Aminomethyl)-2-(5-methoxy-1-benzofuran-2-yl)-N-methylimidazo[1,2-a]pyridin-3-amine | Tr(MET-uHPLC-AB-101) = 1.32 min, (ES$^+$) (M + H)$^+$ 323 |

Method 15

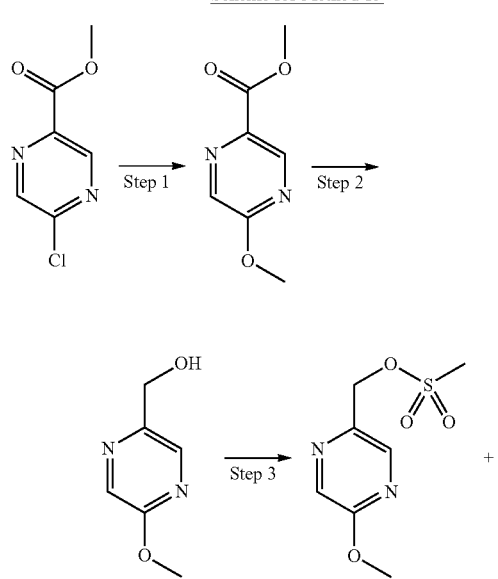

Scheme for Method 15

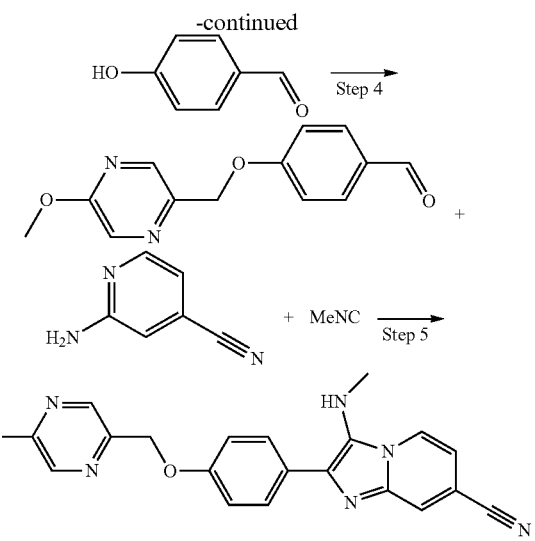

Step 1, Method 15: Methyl 5-methoxypyrazine-2-carboxylate

Methyl 5-chloropyrazine-2-carboxylate (2 g, 11.6 mmol) was dissolved in a 0.5 M sodium methoxide in methanol (27.8 mL, 13.9 mmol) under nitrogen. The mixture was refluxed for 15 minutes. The mixture was then dissolved with water (80 mL) and extracted with ethyl acetate (2×100 mL). The combined organic extracts were dried, filtered and concentrated to give the title compound 1.68 g (79% yield) as a white powder. $\delta_H$ NMR (500 MHz, chloroform) 8.88 (d, J=1.2 Hz, 1H), 8.28 (d, J=1.2 Hz, 1H), 4.05 (s, 3H), 4.00 (s, 3H). Tr(METCR1278)=1.23 min, (ES$^+$) (M+H)$^+$ 169.

Step 2, Method 15: (5-Methoxypyrazin-2-yl)methanol

Sodium borohydride (12.2 g, 323 mmol) was added to a stirred solution of methyl 5-methoxypyrazine-2-carboxylate (18.1 g, 108 mmol) in tetrahydrofuran (400 mL) under nitrogen. The mixture was refluxed for 15 minutes, after which methanol (40 mL) was added slowly. The reaction was refluxed for 1.5 hours then cooled to room temperature. The mixture was then quenched using water (200 mL), then extracted with ethyl acetate (3×150 mL). The combined organic extracts were dried, filtered and concentrated to give the title compound 9.33 g (62% yield) as a light yellow powder. $\delta_H$ NMR (500 MHz, DMSO) 8.28-8.16 (m, 2H), 5.41 (t, J=5.8 Hz, 1H), 4.54 (d, J=5.6 Hz, 2H), 3.90 (s, 3H). Tr(METCR1278)=0.74 min, (ES$^+$) (M+H)$^+$141.

Step 3, Method 15: (5-Methoxypyrazin-2-yl)methyl methanesulfonate (5-Methoxypyrazin-2-yl)methanol (73 mg, 0.52 mmol) was dissolved in dichloromethane (1 mL) under nitrogen. Triethylamine (0.08 mL, 0.73 mmol) was added, followed by methanesulfonyl chloride (42 µL, 0.55 mmol). The mixture was stirred at room temperature for 1 hour. The mixture was partitioned between dichloromethane (10 mL) and water (10 mL). The organic phase was dried, filtered and concentrated to give the title compound 59 mg (52% yield) as a yellow oil. Tr(METCR1278)=1.25 min, (ES$^+$) (M+H)$^+$ 219.

Step 4, Method 15: 4-[(5-Methoxypyrazin-2-yl)methoxy]benzaldehyde

A suspension of 4-hydroxybenzaldehyde (104 mg, 0.85 mmol), potassium carbonate (236 mg, 1.71 mmol) and (5-methoxypyrazin-2-yl)methyl methanesulfonate (73%, 255 mg, 0.85 mmol) in acetone (10 mL) was heated to reflux for 16 hours. The reaction mixture was filtered and concentrated. Purification by FCC (silica, 6-50% ethyl acetate in heptane) gave the title compound 101 mg (48% yield) as a white powder. δ$_H$ NMR (500 MHz, DMSO) 9.90 (s, 1H), 8.27 (s, 1H), 8.24 (s, 1H), 7.95-7.72 (m, 2H), 7.11 (d, J=8.7 Hz, 2H), 5.23 (s, 2H), 3.99 (s, 3H). Tr(METCR1278)=1.71 min, (ES$^+$) (M+H)$^+$245.

Step 5, Method 15: 2-{4-[(5-Methoxypyrazin-2-yl)methoxy]phenyl}-3-(methylamino)imidazo[1,2-a]pyridine-7-carbonitrile 4-[(5-Methoxypyrazin-2-yl)methoxy]benzaldehyde (101 mg, 0.41 mmol) and 2-aminoisonicotinonitrile (49 mg, 0.41 mmol) were dissolved in methanol (2 mL). Acetic acid (0.2 mL) and methyl isocyanide (22 µL, 0.41 mmol) were added and the mixture stirred at room temperature. After 18 hours, the reaction mixture was filtered, and the collected solid washed with methyl tert-butyl ether (2×5 mL). Drying under suction gave the title compound 55 mg (33% yield) as a yellow powder.

Example 1, Method 15: 2-{4-[(5-Methoxypyrazin-2-yl)methoxy]phenyl}-3-(methylamino)imidazo[1,2-a]pyridine-7-carbonitrile δ$_H$ NMR (500 MHz, DMSO) 8.42-8.38 (m, 2H), 8.35 (d, J=1.3 Hz, 1H), 8.18 (s, 1H), 8.04 (d, J=8.8 Hz, 2H), 7.20-7.13 (m, 3H), 5.21 (s, 2H), 5.05 (q, J=5.4 Hz, 1H), 3.93 (s, 3H), 2.71 (d, J=5.4 Hz, 3H). Tr(MET-uHPLC-AB-101)=2.67 min, (ES$^+$) (M+H)$^+$387.

The following example was prepared using Method 15 described above:

TABLE 15

| Ex. | Structure | Mol. Weight | IUPAC Name | LCMS data |
|---|---|---|---|---|
| 1 | 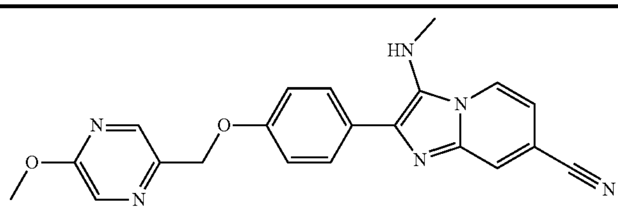 | 386.41 | 2-{4-[(5-Methoxypyrazin-2-yl)methoxy]phenyl}-3-(methylamino)imidazo[1,2-a]pyridine-7-carbonitrile | Tr(MET-uHPLC-AB-101) = 2.67 min, (ES$^+$) (M + H)$^+$ 387 |
| 2 | 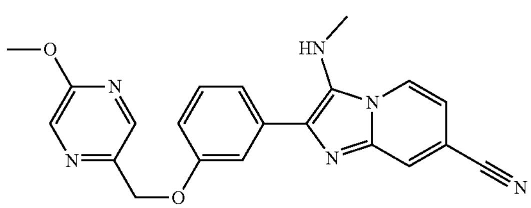 [SMILES: CNc1c(-c2cccc(OCc3cnc(OC)cn3)c2)nc2cc(C#N)ccn12] | 386.41 | 2-{3-[(5-Methoxypyrazin-2-yl)methoxy]phenyl}-3-(methylamino)imidazo[1,2-a]pyridine-7-carbonitrile | Tr(MET-uHPLC-AB-101) = 2.86 min, (ES$^+$) (M + H)$^+$ 387 |
| 3 | 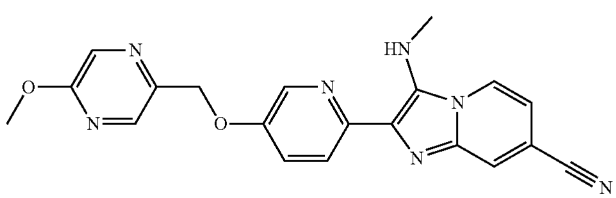 [SMILES: CNc1c(-c2ccc(OCc3cnc(OC)cn3)cn2)nc2cc(C#N)ccn12] | 387.39 | 2-{5-[(5-Methoxypyrazin-2-yl)methoxy]pyridin-2-yl}-3-(methylamino)imidazo[1,2-a]pyridine-7-carbonitrile | Tr(MET-uHPLC-AB-101) = 2.98 min, (ES$^+$) (M + H)$^+$ 388 |

Method 16

Scheme for Method 16

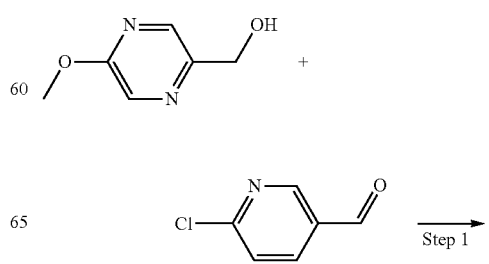

61

-continued

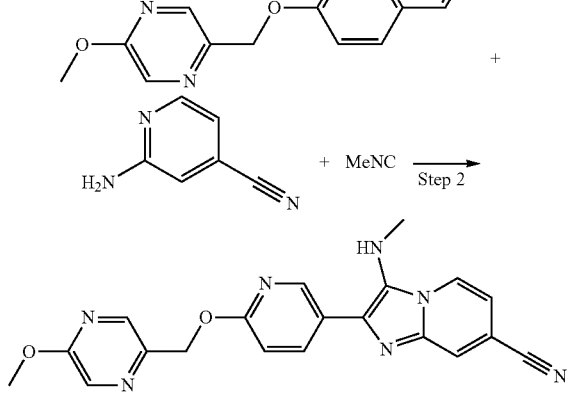

Step 1, Method 16: 6-[(5-Methoxypyrazin-2-yl)methoxy]pyridine-3-carbaldehyde (5-Methoxypyrazin-2-yl)methanol (prepared according to Method 15, 200 mg, 1.43 mmol) was dissolved in anhydrous N,N-dimethylformamide (3 mL) under nitrogen. Potassium tert-butoxide (88 mg, 0.78 mmol) was added and the mixture stirred for 15 minutes. 6-Chloropyridine-3-carbaldehyde (202 mg, 1.43 mmol) was added and the mixture stirred at room temperature for 18 hours. The reaction mixture was partitioned between ethyl acetate (10 mL) and saturated

62

Step 2, Method 16: 2-{6-[(5-Methoxypyrazin-2-yl)methoxy]pyridin-3-yl}-3-(methylamino)imidazo[1,2-a]pyridine-7-carbonitrile 6-[(5-Methoxypyrazin-2-yl)methoxy]pyridine-3-carbaldehyde (42 mg, 0.17 mmol) and 2-aminoisonicotinonitrile (20 mg, 0.17 mmol) were dissolved in methanol (2 mL). Acetic acid (0.2 mL) and methyl isocyanide (13 µL, 0.26 mmol) were added and the mixture stirred at room temperature for 64 hours. The reaction mixture was quenched with 1 M hydrochloric acid (2 mL) and stood at room temperature for 20 minutes. The organic solvents were removed in vacuo and the aqueous neutralised with saturated aqueous sodium bicarbonate. The solution was extracted with ethyl acetate (2×10 mL). Combined organic extracts were washed with brine (10 mL), dried, filtered and concentrated. Purification by preparative HPLC (acetonitrile-water-0.2% ammonium hydroxide) gave the title compound 15 mg (21% yield) as a yellow powder.

Example 1, Method 16: 2-{6-[(5-Methoxypyrazin-2-yl)methoxy]pyridin-3-yl}-3-(methylamino)imidazo[1,2-a]pyridine-7-carbonitrile $\delta_H$ NMR (500 MHz, DMSO) 8.84 (d, J=2.2 Hz, 1H), 8.42 (d, J=7.1 Hz, 1H), 8.39 (s, 1H), 8.36 (dd, J=8.6, 2.4 Hz, 1H), 8.33 (d, J=1.2 Hz, 1H), 8.22 (s, 1H), 7.19 (dd, J=7.1, 1.5 Hz, 1H), 7.02 (d, J=8.7 Hz, 1H), 5.46 (s, 2H), 5.13 (q, J=5.4 Hz, 1H), 3.92 (s, 3H), 2.72 (d, J=5.4 Hz, 3H). Tr(MET-uHPLC-AB-101)=2.78 min, (ES$^+$) (M+H)$^+$388.

The following examples were prepared using Method 16 described above:

TABLE 16

| Ex. | Structure | Mol. Weight | IUPAC Name | LCMS data |
|---|---|---|---|---|
| 1 | 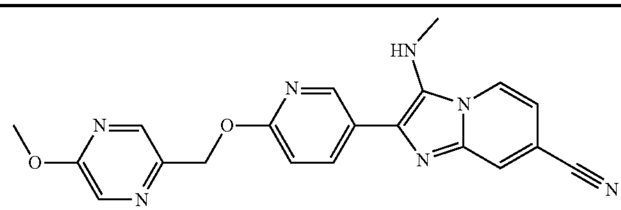 | 387.39 | 2-{6-[(5-Methoxypyrazin-2-yl)methoxy]pyridin-3-yl}-3-(methylamino)imidazo[1,2-a]pyridine-7-carbonitrile | Tr(MET-uHPLC-AB-101) = 2.78 min, (ES$^+$) (M + H)$^+$ 388 |
| 2 | | 387.40 | 2-{5-[(5-Methoxypyridin-2-yl)methoxy]pyrazin-2-yl}-3-(methylamino)imidazo[1,2-a]pyridine-7-carbonitrile | Tr(MET-uHPLC-AB-101) = 2.76 min, (ES$^+$) (M + H)$^+$ 388 | aqueous sodium bicarbonate (10 mL). The suspension was extracted with ethyl acetate (3×10 mL). Combined organic layers were washed with water (2×10 mL) and brine (2×10 mL), then dried, filtered and concentrated. Purification by FCC (silica, 12-100% ethyl acetate in heptane) gave the title compound 42 mg (10% yield) as a white powder. $^6$H NMR (500 MHz, DMSO) 9.97 (s, 1H), 8.78 (d, J=2.3 Hz, 1H), 8.39 (s, 1H), 8.33 (s, 1H), 8.15 (dd, J=8.6, 2.3 Hz, 1H), 7.06 (d, J=8.6 Hz, 1H), 5.51 (s, 2H), 3.92 (s, 3H). Tr(METCR1278)=1.65 min, (ES$^+$) (M+H)$^+$246, 81%.

Method 17

Scheme for Method 17

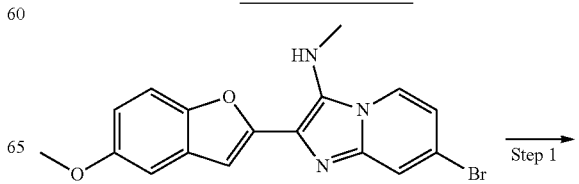

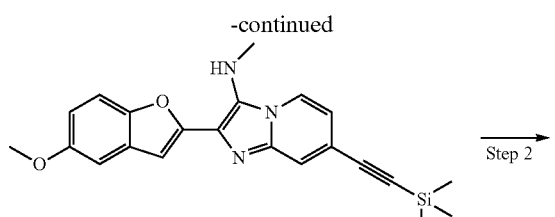

Step 1, Method 17: 2-(5-Methoxy-1-benzofuran-2-yl)-N-methyl-7-[2-(trimethylsilyl)ethynyl]imidazo[1,2-a]pyridin-3-amine 7-Bromo-2-(5-methoxy-1-benzofuran-2-yl)-N-methyl-imidazo[1,2-a]pyridin-3-amine (150 mg, 0.4 mmol, prepared by Method 1), trimethylsilylacetylene (69 µL, 0.48 mmol), copper(I) iodide (8 mg, 0.04 mmol) and bis(triphenylphosphine)palladium(II) dichloride (14 mg, 0.02 mmol) were dissolved in anhydrous dioxane (5 mL) in a pressure tube. The vessel was sealed and the mixture heated to 100° C. for 16 hours. The reaction mixture was cooled to room temperature and partitioned between ethyl acetate (20 mL) and water (20 mL). The layers were separated and the organic phase washed with brine (15 mL), then dried, filtered and concentrated. Purification by FCC (silica, 6-50% ethyl acetate in heptane) gave the title compound 87 mg (55% yield) as a yellow powder. $\delta_H$ NMR (500 MHz, DMSO) 8.24 (d, J=7.1 Hz, 1H), 7.59 (s, 1H), 7.52 (d, J=8.9 Hz, 1H), 7.19 (s, 1H), 7.18 (d, J=2.6 Hz, 1H), 6.94-6.86 (m, 2H), 5.18 (q, J=5.4 Hz, 1H), 3.80 (s, 3H), 2.84 (d, J=5.5 Hz, 3H), 0.26 (s, 9H). Tr(MET-uHPLC-AB-101)=3.98 min, (ES⁺) (M+H)⁺390.

Step 2, Method 17: 7-Ethynyl-2-(5-methoxy-1-benzofuran-2-yl)-N-methylimidazo[1,2-a]pyridin-3-amine 2-(5-Methoxy-1-benzofuran-2-yl)-N-methyl-7-[2-(trimethylsilyl)ethynyl]imidazo[1,2-a]pyridin-3-amine (77 mg, 0.2 mmol) was dissolved in ethanol (3 mL) and cooled to 0° C. Potassium carbonate (44 mg, 0.32 mmol) was added and the mixture stirred at 0° C. for 1.5 hours. The reaction mixture was partitioned between ethyl acetate (15 mL) and water (15 mL). The layers were separated and the organic phase washed with brine (10 mL), then dried, filtered and concentrated to give an orange powder (47 mg). The powder was triturated in boiling 2:1 acetonitrile:DMSO and filtered. The collected solid was purified by FCC (silica, 25% ethyl acetate in heptane) to give the title compound 7 mg (12% yield) as an orange powder.

Example 1, Method 17: 7-Ethynyl-2-(5-methoxy-1-benzofuran-2-yl)-N-methylimidazo[1,2-a]pyridin-3-amine $\delta_H$ NMR (500 MHz, DMSO) 8.26 (d, J=7.1 Hz, 1H), 7.65 (s, 1H), 7.52 (d, J=8.9 Hz, 1H), 7.19 (s, 1H), 7.18 (d, J=2.6 Hz, 1H), 6.90 (m, 2H), 5.15 (q, J=5.5 Hz, 1H), 4.43 (s, 1H), 3.80 (s, 3H), 2.84 (d, J=5.5 Hz, 3H). Tr(MET-uHPLC-AB-101)=2.7 min, (ES⁺) (M+H)⁺318.

The following examples were prepared using Method 17 described above:

TABLE 17

| Ex. | Structure | Mol. Weight | IUPAC Name | LCMS data |
|---|---|---|---|---|
| 1 | 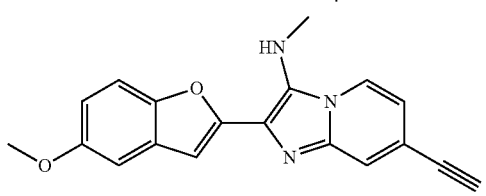 | 317.34 | 7-Ethynyl-2-(5-methoxy-1-benzofuran-2-yl)-N-methylimidazo[1,2-a]pyridin-3-amine | Tr(MET-uHPLC-AB-101) = 2.7 min, (ES⁺) (M + H)⁺ 318 |
| 2 | 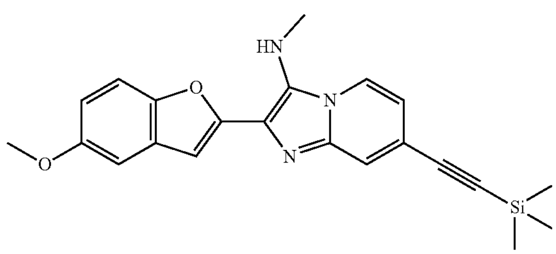 | 389.52 | 2-(5-Methoxy-1-benzofuran-2-yl)-N-methyl-7-[2-(trimethylsilyl)ethynyl]imidazo[1,2-a]pyridin-3-amine | Tr(MET-uHPLC-AB-101) = 3.98 min, (ES⁺) (M + H)⁺ 390 |

Method 18

Scheme for Method 18

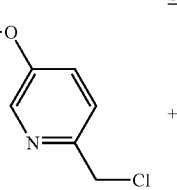

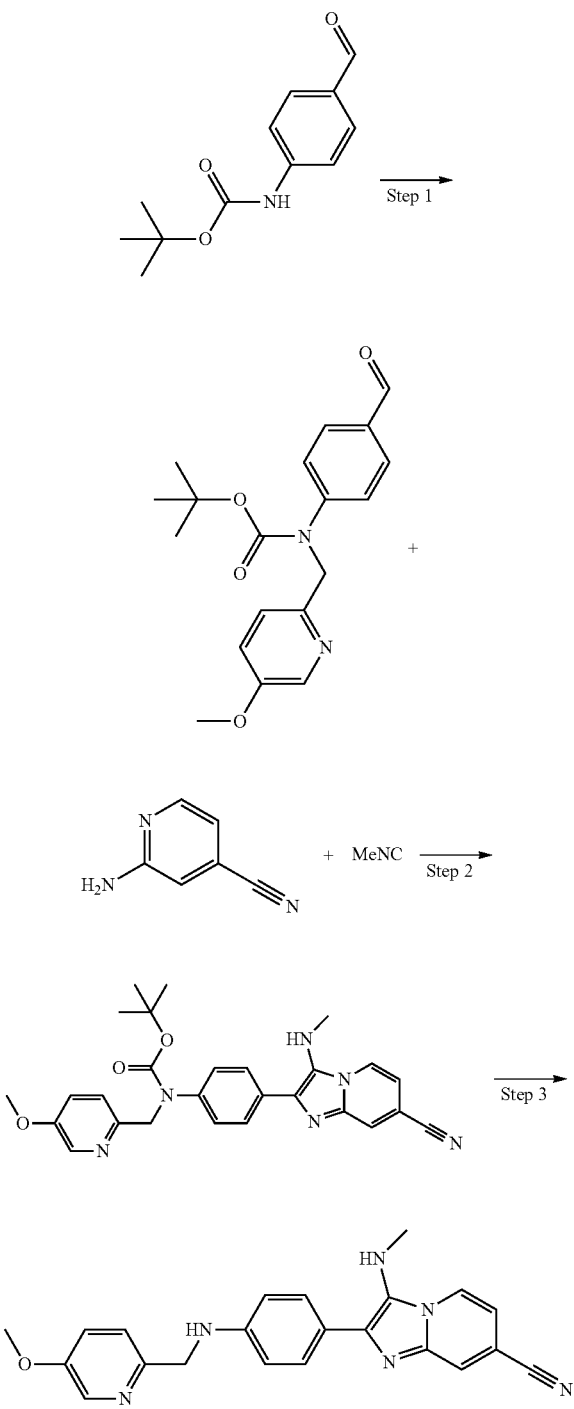

Step 1, Method 18: tert-Butyl N-(4-formylphenyl)-N-[(5-methoxypyridin-2-yl)methyl]carbamate tert-Butyl N-(4-formylphenyl)carbamate (200 mg, 1.8 mmol) and 2-(chloromethyl)-5-methoxypyridine hydrochloride (175 mg, 0.90 mmol) were dissolved in anhydrous N,N-dimethylformamide (5 mL) and cooled to 0° C. Potassium iodide (15 mg, 0.09 mmol) and sodium hydride (60% in mineral oil, 108 mg, 2.71 mmol) were added and the mixture stirred at room temperature for 64 hours. The reaction mixture was quenched by the addition of water (10 mL). The solution was extracted with ethyl acetate (3×15 mL). The combined organic extracts were washed with brine (3×10 mL), dried, filtered and concentrated. Purification by FCC (silica, 6-65% ethyl acetate in heptane) gave the title compound 74 mg (24% yield) as a colourless oil. $\delta_H$ NMR (500 MHz, chloroform) 9.93 (s, 1H), 8.24 (d, J=2.8 Hz, 1H), 7.90-7.71 (m, 2H), 7.49 (d, J=8.6 Hz, 2H), 7.23 (d, J=8.6 Hz, 1H), 7.18 (dd, J=8.6, 2.9 Hz, 1H), 4.97 (s, 2H), 3.85 (s, 3H), 1.42 (s, 9H). Tr(METCR1278)=1.87 min, (ES$^+$) (M+H)$^+$ 343.

Step 2, Method 18: tert-Butyl-N-{4-[7-cyano-3-(methylamino)imidazo[1,2-a]pyridin-2-yl]phenyl}-N-[(5-methoxypyridin-2-yl)methyl]carbamate tert-Butyl N-(4-formylphenyl)-N-[(5-methoxypyridin-2-yl)methyl]carbamate (74 mg, 0.22 mmol) and 2-aminoisonicotinonitrile (26 mg, 0.21 mmol) were dissolved in methanol (3 mL). Acetic acid (0.3 mL) and methyl isocyanide (17 μL, 0.32 mmol) were added and the mixture stirred at room temperature for 16 hours. The reaction mixture was quenched with 1 M hydrochloric acid (2 mL) and stirred at room temperature for 40 minutes. The organic solvents were removed in vacuo and the aqueous neutralised with saturated aqueous sodium bicarbonate. The solution was extracted with ethyl acetate (2×15 mL). The combined organic extracts were washed with brine (10 mL), dried, filtered and concentrated. Purification by FCC (silica, 50-100% ethyl acetate in heptane) gave the title compound 35 mg (33% yield) as a yellow powder. Tr(METCR1278)=1.27 min, (ES$^+$) (M+H)$^+$485.

Step 3, Method 18: (2-(4-{[(5-Methoxypyridin-2-yl)methyl]amino}phenyl)-3-(methylamino)imidazo[1,2-a]pyridine-7-carbonitrile tert-Butyl-N-{4-[7-cyano-3-(methylamino)imidazo[1,2-a]pyridin-2-yl]phenyl}-N-[(5-methoxypyridin-2-yl)methyl]carbamate (35 mg, 0.07 mmol) was dissolved in 4 M hydrochloric acid in dioxane (1 mL) and water (0.1 mL). The mixture was stirred at room temperature for 3 hours then concentrated. Purification using an SCX column to give the title compound 22 mg (75% yield) as an orange powder.

Example 1, Method 18: (2-(4-{[(5-Methoxypyridin-2-yl)methyl]amino}phenyl)-3-(methylamino)imidazo[1,2-a]pyridine-7-carbonitrile $\delta_H$ NMR (500 MHz, DMSO) 8.32 (d, J=7.1 Hz, 1H), 8.25 (d, J=2.7 Hz, 1H), 8.09 (s, 1H), 7.81 (d, J=8.7 Hz, 2H), 7.36 (dd, J=8.6, 2.8 Hz, 1H), 7.33 (d, J=8.6 Hz, 1H), 7.12 (dd, J=7.1, 1.6 Hz, 1H), 6.67 (d, J=8.7 Hz, 2H), 6.54 (t, J=6.0 Hz, 1H), 4.89 (q, J=5.4 Hz, 1H), 4.34 (d, J=6.1 Hz, 2H), 3.80 (s, 3H), 2.67 (d, J=5.4 Hz, 3H). Tr(MET-uHPLC-AB-101)=1.59 min, (ES$^+$) (M+H)$^+$385.

The following example was prepared using Method 18 described above:

TABLE 18

| Ex. | Structure | Mol. Weight | IUPAC Name | LCMS data |
|---|---|---|---|---|
| 1 | 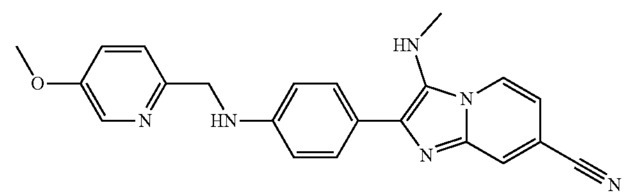 [SMILES: CNc1c(-c2ccc(NCc3ccc(OC)cn3)cc2)nc2cc(C#N)ccn12] | 384.43 | 2-(4-{[(5-Methoxypyridin-2-yl)methyl]amino}phenyl)-3-(methylamino)imidazo[1,2-a]pyridine-7-carbonitrile | Tr(MET-uHPLC-AB-101) = 1.59 min, (ES$^+$) (M + H)$^+$ 385 |

Method 19

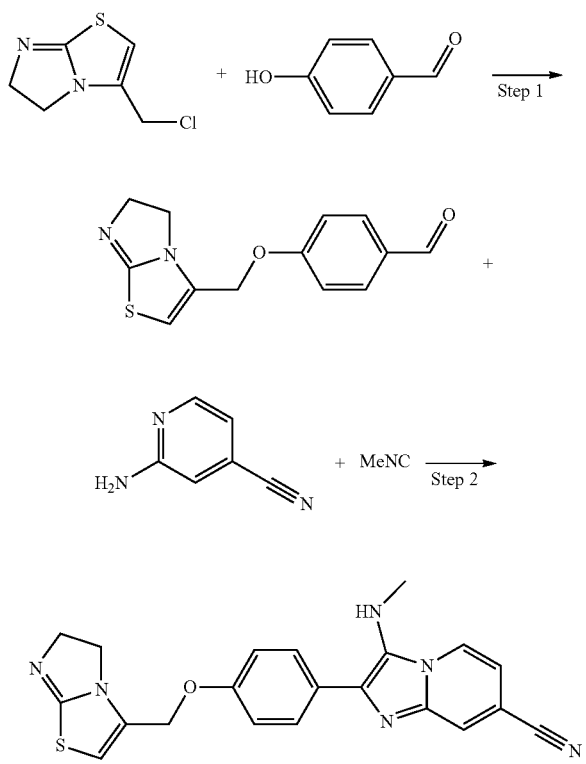

Scheme for Method 19

Step 1, Method 19: 4-{5H,6H-Imidazo[2,1-b][1,3]thiazol-3-ylmethoxy}benzaldehyde A suspension of 4-hydroxybenzaldehyde (100 mg, 0.82 mmol), potassium iodide (136 mg, 0.82 mmol) and 3-(chloromethyl)-5,6-dihydroimidazo[2,1-b][1,3]thiazole hydrochloride (173 mg, 0.82 mmol) in anhydrous N,N-dimethylformamide (5 mL) cooled to 0° C. under nitrogen was treated with sodium hydride (60% in mineral oil, 82 mg, 2.05 mmol). The mixture was stirred, warming to room temperature. After 20 hours, the reaction mixture was quenched with water (10 mL) and extracted with ethyl acetate (3×15 mL). Combined organic extracts were washed with brine (3×10 mL), dried, filtered and concentrated to give an off-white powder. The crude product was suspended in methyl tert-butyl ether (10 mL) and sonicated to form a fine suspension. The mixture was filtered, and the collected solid washed with further methyl tert-butyl ether (3×10 mL). Drying under suction gave the title compound 97 mg (44% yield) as an off-white powder. $\delta_H$ NMR (500 MHz, DMSO) 9.89 (s, 1H), 7.89 (d, J=8.7 Hz, 2H), 7.23 (d, J=8.7 Hz, 2H), 6.10 (s, 1H), 4.96 (s, 2H), 4.06 (t, J=9.4 Hz, 2H), 3.80 (t, J=9.4 Hz, 2H). Tr(METCR1278)=0.98 min, (ES$^+$) (M+H)$^+$ 261.

Step 2, Method 19: 2-(4-{5H,6H-Imidazo[2,1-b][1,3]thiazol-3-ylmethoxy}phenyl)-3-(methylamino)imidazo[1,2-a]pyridine-7-carbonitrile 4-{5H,6H-Imidazo[2,1-b][1,3]thiazol-3-ylmethoxy}benzaldehyde (97 mg, 0.37 mmol) and 2-aminoisonicotinonitrile (44 mg, 0.37 mmol) were dissolved in methanol (3 mL). Acetic acid (0.3 mL) and methyl isocyanide (29 µL, 0.29 mmol) were added and the mixture stirred at room temperature. The reaction mixture was quenched with 1 M hydrochloric acid (2 mL) and stirred at room temperature for 30 minutes. The organic solvents were removed in vacuo and the aqueous neutralised with saturated aqueous sodium bicarbonate. The solution was extracted with ethyl acetate (2×15 mL). The combined organic extracts were washed with brine (10 mL), dried, filtered and concentrated. The crude material was dissolved in 2:1 acetonitrile:DMSO (1.5 mL) and purified by preparative HPLC (acetonitrile-water-0.2% ammonium hydroxide) to give the title compound 3.2 mg (2% yield) as a yellow powder.

Example 1, Method 19: 2-(4-{5H,6H-Imidazo[2,1-b][1,3]thiazol-3-ylmethoxy}phenyl)-3-(methylamino)imidazo[1,2-a]pyridine-7-carbonitrile $\delta_H$ NMR (500 MHz, DMSO) 8.40 (d, J=7.1 Hz, 1H), 8.18 (s, 1H), 8.04 (d, J=8.8 Hz, 2H), 7.28-7.02 (m, 3H), 6.08 (s, 1H), 5.05 (q, J=5.2 Hz, 1H), 4.88 (s, 2H), 4.08 (t, J=9.4 Hz, 2H), 3.83 (t, J=9.4 Hz, 2H), 2.71 (d, J=5.4 Hz, 3H). Tr(MET-uHPLC-AB-101)=1.45 min, (ES$^+$) (M+H)$^+$ 403.

The following example was prepared using Method 19 described above:

TABLE 19

| Ex. | Structure | Mol. Weight | IUPAC Name | LCMS data |
|---|---|---|---|---|
| 1 | 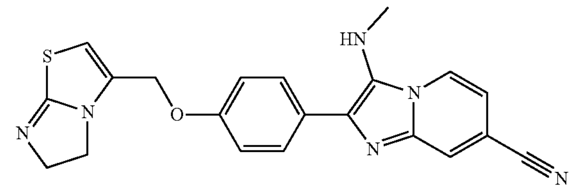 [SMILES: CNc1c(-c2ccc(OCC3=CSC4=NCCN34)cc2)nc2cc(C#N)ccn12] | 402.47 | 2-(4-{5H,6H-Imidazo[2,1-b][1,3]thiazol-3-ylmethoxy}phenyl)-3-(methylamino)imidazo[1,2-a]pyridine-7-carbonitrile | Tr(MET-uHPLC-AB-101) = 1.45 min, (ES+) (M + H)+ 403 |

Method 20

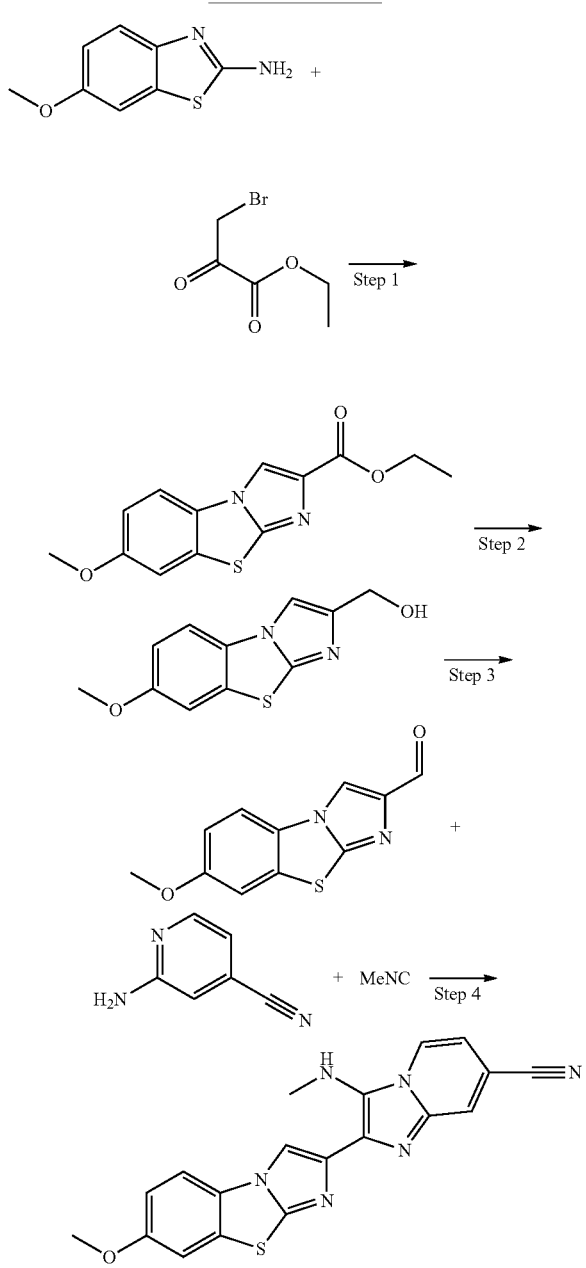

Scheme for Method 20

Step 1, Method 20: Ethyl 10-methoxy-7-thia-2,5-diazatricyclo[6.4.0.0$^{2,6}$]dodeca-1(12),3,5,8,10-pentaene-4-carboxylate 6-Methoxy-1,3-benzothiazol-2-amine (5 g, 27.7 mmol) was dissolved in 1,2-dimethoxyethane (60 mL). Ethyl 3-bromo-2-oxopropanoate (3.48 mL, 27.7 mmol) was added and the resulting mixture heated to reflux for 18 hours. The mixture was then cooled to room temperature and stood for 48 hours. The mixture was filtered, and collected solid washed with methyl tert-butyl ether (2×10 mL) then dried under suction. The solid was suspended in water and the mixture adjusted to pH 9 with ammonium hydroxide solution. The mixture was filtered, and collected solid washed with methyl tert-butyl ether (100 mL) then dried under suction (4.8 g). 1.45 g was purified by FCC (silica, 12-100% ethyl acetate in heptane) to give the title compound 122 mg (2% yield) as a yellow powder. $\delta_H$ NMR (500 MHz, DMSO) 8.96 (s, 1H), 8.08 (d, J=8.9 Hz, 1H), 7.69 (d, J=2.5 Hz, 1H), 7.15 (dd, J=8.9, 2.5 Hz, 1H), 4.29 (q, J=7.1 Hz, 2H), 3.83 (s, 3H), 1.31 (t, J=7.1 Hz, 3H). Tr(MET-uHPLC-AB-101)=2.8 min, (ES+) (M+H)+277.

Step 2, Method 20: {10-Methoxy-7-thia-2,5-diazatricyclo[6.4.0.0$^{2,6}$]dodeca-1(12),3,5,8,10-pentaen-4-yl}methanol Ethyl 10-methoxy-7-thia-2,5-diazatricyclo[6.4.0.0$^{2,6}$]dodeca-1(12),3,5,8,10-pentaene-4-carboxylate (500 mg, 1.81 mmol) was dissolved in anhydrous tetrahydrofuran (10 mL) under nitrogen and cooled to 0° C. 2.4 M Lithium aluminium hydride in tetrahydrofuran (904 μL, 2.17 mmol) was added drop-wise over 2 minutes. The reaction mixture was stirred at room temperature for 18 hours then quenched by the addition of water (60 μL) and 2 M sodium hydroxide (100 μL). The quenched mixture was then filtered through celite, washed with ethyl acetate (20 mL) and the filtrate concentrated to give the title compound 90 mg (19% yield) as a yellow powder. $\delta_H$ NMR (500 MHz, DMSO) 8.04 (s, 1H), 7.91 (d, J=8.8 Hz, 1H), 7.63 (d, J=2.5 Hz, 1H), 7.10 (dd, J=8.8, 2.5 Hz, 1H), 5.10 (s, 1H), 4.47 (s, 2H), 3.82 (s, 3H). Tr(METCR1673)=0.84 min, (ES+) (M+H)+235, 89%.

Step 3, Method 20: 10-Methoxy-7-thia-2,5-diazatricyclo[6.4.0.0$^{2,6}$]dodeca-1(12),3,5,8,10-pentaene-4-carbaldehyde {10-Methoxy-7-thia-2,5-diazatricyclo[6.4.0.0$^{2,6}$]dodeca-1(12),3,5,8,10-pentaen-4-yl}methanol (90%, 80 mg, 0.31 mmol) was dissolved in dichloromethane (5 mL) and treated with Dess-Martin periodinane (156 mg, 0.37 mmol). The mixture was stirred at room temperature for 64 hours. The reaction was then quenched by the addition of saturated aqueous sodium sulphite (2 mL) and saturated aqueous sodium bicarbonate (2 mL). The mixture was stirred for 5 minutes. The mixture was diluted with water (10 mL) and dichloromethane (10 mL). The layers were separated and the aqueous further extracted with dichloromethane (2×10 mL). The combined organic extracts were washed with brine (10 mL), dried, filtered and concentrated to give the title compound 65 mg (77% yield) as a light orange powder. $\delta_H$ NMR (500 MHz, DMSO) 9.83 (s, 1H), 9.06 (s, 1H), 8.08 (d, J=8.9 Hz, 1H), 7.72 (d, J=2.5 Hz, 1H), 7.18 (dd, J=8.9, 2.5 Hz, 1H), 3.85 (s, 3H). Tr(METCR1673)=1.10 min, (ES$^+$) (M+H)$^+$233, 85%.

Step 4, Method 20: 2-{10-Methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile 10-Methoxy-7-thia-2,5-diazatricyclo[6.4.0.0$^{2,6}$]dodeca-1(12),3,5,8,10-pentaene-4-carbaldehyde (65 mg, 0.28 mmol) and 2-aminoisonicotinonitrile (33 mg, 0.28 mmol) were suspended in methanol (5 mL). Acetic acid (0.5 mL) and methyl isocyanide (22 µL, 0.42 mmol) were added and the mixture stirred at room temperature for 18 hours. The reaction mixture was filtered, and collected solid dried under suction to give the title compound 28 mg (26% yield) as a yellow powder.

Example 1, Method 20: 2-{10-Methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile $\delta_H$ NMR (500 MHz, DMSO) 8.71 (s, 1H), 8.35 (d, J=7.1 Hz, 1H), 8.15 (s, 1H), 8.05 (d, J=8.9 Hz, 1H), 7.70 (d, J=2.5 Hz, 1H), 7.16 (dd, J=8.9, 2.5 Hz, 1H), 7.11 (dd, J=7.1, 1.6 Hz, 1H), 5.63 (q, J=5.8 Hz, 1H), 3.84 (s, 3H), 2.90 (d, J=5.9 Hz, 3H). Tr(MET-uHPLC-AB-101)=3.12 min, (ES$^+$) (M+H)$^+$375.

The following examples were prepared using Method 20 described above:

Biology Examples

Q46 Radioligand Binding Assay

For radioligand binding assays (RBA) GST-Q46 protein was generated based on a previous publication (Scherzinger et al. Cell, Vol. 90, 549-558, Aug. 8, 1997). For experiments 33 µM GST-Q46 was incubated with 150 µg/mL thrombin in assay buffer (150 mM NaCl, 50 mM Tris pH 8.0) and 2 mM CaCl$_2$ for 16 hours at 37° C. Aggregated Q46 was pelleted by centrifugation for 5 minutes at 13,000 rpm in a bench top centrifuge and re-dissolved in the same volume of assay buffer. Test compounds were prepared by titration in DMSO at 11 concentrations from 33 µM to 1 nM. For the RBA, Q46 protein aggregates and test compounds were pre-incubated in assay buffer for 20 minutes at room temperature, in 140 µL/well in a 96-well plate (pp, round bottom). Then, ligand was added in 10 µL/well and incubated for 60 minutes at 37° C. Final assay concentrations were 1 µM to 30 µM test compound, 5 µM Q46 protein (equivalent monomer concentration) and 10 nM ligand [$^3$H$_3$]MK-3328 (Harrision et al., ACS Med. Chem. Lett., 2 (2011), pp 498-502). Samples were transferred onto GF/B filter plates and washed 2× with 200 µL PBS using a Filtermate Harvester. After drying filter plates for 1 hour at 37° C., the back of the plates was sealed with foil and 30 µl/well scintillation fluid (Packard MicroScint 40) was added, incubated for incubated for 15 minutes in the dark and counted in a TopCount reader. For analysis, replicate data from independent assay plates were normalized towards 0% and 100% inhibition using control wells of vehicle (0% inhibition) and 3 µM unlabelled MK-3328 (100% inhibition). IC$_{50}$ values were determined with a sigmoidal inhibition model with four variables (top, bottom, slope, IC$_{50}$) in a global fit using the normalized replicate data.

TABLE 20

| Ex. | Structure | Mol. Weight | IUPAC Name | LCMS data |
|---|---|---|---|---|
| 1 | 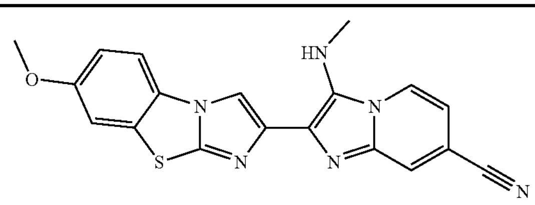 | 374.42 | 2-{10-Methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile | Tr(MET-uHPLC-AB-101) = 3.12 min, (ES$^+$) (M + H)$^+$ 375 |
| 2 | 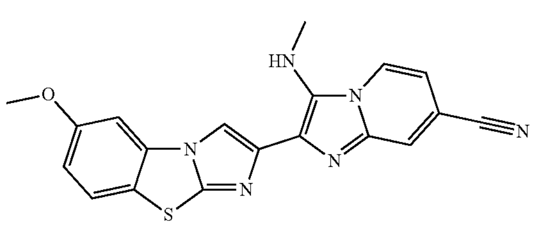 [SMILES: CNc1c(-c2cn3c(n2)sc2ccc(OC)cc23)nc2cc(C#N)ccn12] | 374.42 | 2-{11-Methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile | Tr(MET-uHPLC-AB-101) = 3.29 min, (ES$^+$) (M + H)$^+$ 375 |

| Structure | IUPAC Name | Activity |
|---|---|---|
| 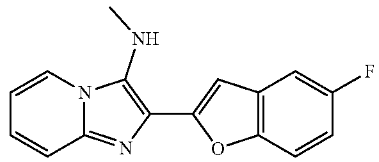 [SMILES: CNc1c(-c2cc3cc(F)ccc3o2)nc2ccccn12] | 2-(5-fluoro-1-benzofuran-2-yl)-N-methylimidazo[1,2-a]pyridin-3-amine | + |
| 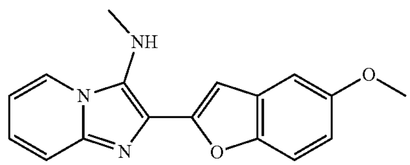 [SMILES: CNc1c(-c2cc3cc(OC)ccc3o2)nc2ccccn12] | 2-(5-methoxy-1-benzofuran-2-yl)-N-methylimidazo[1,2-a]pyridin-3-amine | ++ |
| 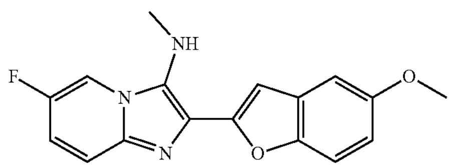 [SMILES: CNc1c(-c2cc3cc(OC)ccc3o2)nc2ccc(F)cn12] | 6-fluoro-2-(5-methoxy-1-benzofuran-2-yl)-N-methylimidazo[1,2-a]pyridin-3-amine | +++ |
| 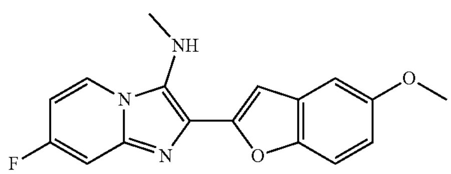 [SMILES: CNc1c(-c2cc3cc(OC)ccc3o2)nc2cc(F)ccn12] | 7-fluoro-2-(5-methoxy-1-benzofuran-2-yl)-N-methylimidazo[1,2-a]pyridin-3-amine | +++ |
| 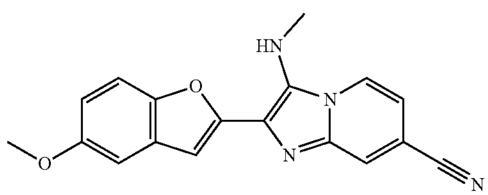 [SMILES: CNc1c(-c2cc3cc(OC)ccc3o2)nc2cc(C#N)ccn12] | 2-(5-methoxy-1-benzofuran-2-yl)-3-(methylamino)imidazo[1,2-a]pyridine-7-carbonitrile | +++ |
| 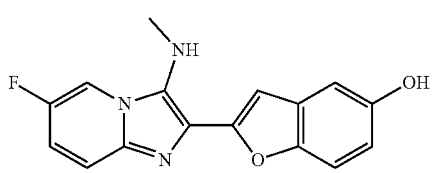 [SMILES: CNc1c(-c2cc3cc(O)ccc3o2)nc2ccc(F)cn12] | 2-[6-fluoro-3-(methylamino)imidazo[1,2-a]pyridin-2-yl]-1-benzofuran-5-ol | ++ |
| 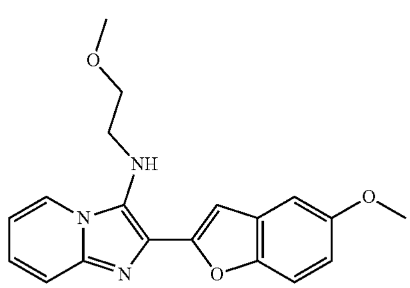 [SMILES: COCCNc1c(-c2cc3cc(OC)ccc3o2)nc2ccccn12] | 2-(5-methoxy-1-benzofuran-2-yl)-N-(2-methoxyethyl)imidazo[1,2-a]pyridin-3-amine | ++ |
| | 2-[7-fluoro-3-(methylamino)imidazo[1,2-a]pyridin-2-yl]-1-benzofuran-5-ol | +++ |

RBA IC$_{50}$ activity summary: <100 nM +++, 100-500 nM ++, >500 nM +

-continued

RBA IC$_{50}$ activity summary: <100 nM +++, 100-500 nM ++, >500 nM +

| Structure | IUPAC Name | Activity |
|---|---|---|
| 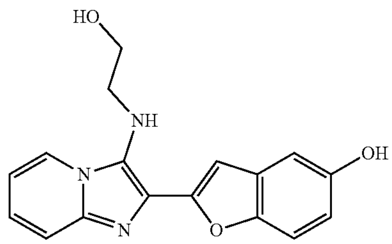 [SMILES: OCCNc1c(-c2cc3cc(O)ccc3o2)nc2ccccn12] | 2-{3-[(2-hydroxyethyl)amino]imidazo[1,2-a]pyridin-2-yl]-1-benzofuran-5-ol | ++ |
| 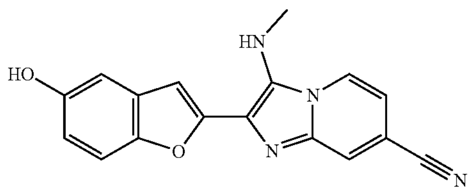 [SMILES: CNc1c(-c2cc3cc(O)ccc3o2)nc2cc(C#N)ccn12] | 2-(5-hydroxy-1-benzofuran-2-yl)-3-(methylamino)imidazo[1,2-a]pyridine-7-carbonitrile | +++ |
| 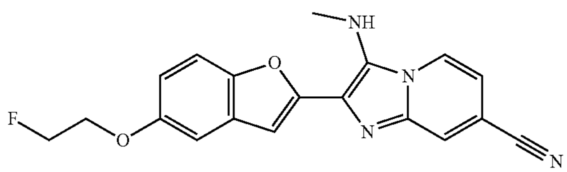 [SMILES: CNc1c(-c2cc3cc(OCCF)ccc3o2)nc2cc(C#N)ccn12] | 2-[5-(2-fluoroethoxy)-1-benzofuran-2-yl]-3-(methylamino)imidazo[1,2-a]pyridine-7-carbonitrile | |
| 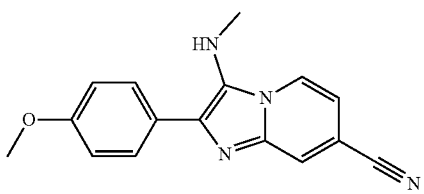 [SMILES: CNc1c(-c2ccc(OC)cc2)nc2cc(C#N)ccn12] | 2-(4-methoxyphenyl)-3-(methylamino)imidazo[1,2-a]pyridine-7-carbonitrile | +++ |
| 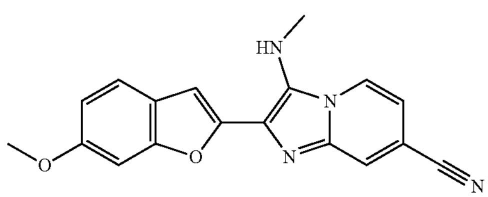 [SMILES: CNc1c(-c2cc3ccc(OC)cc3o2)nc2cc(C#N)ccn12] | 2-(6-methoxy-1-benzofuran-2-yl)-3-(methylamino)imidazo[1,2-a]pyridine-7-carbonitrile | +++ |
| 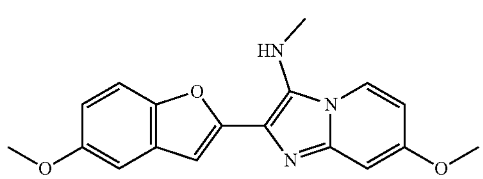 | 7-methoxy-2-(5-methoxy-1-benzofuran-2-yl)-N-methylimidazo[1,2-a]pyridin-3-amine | +++ |
| 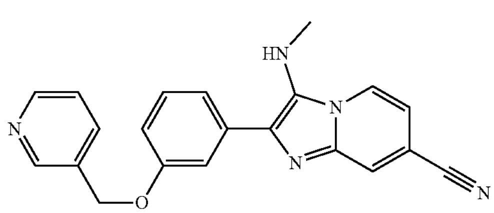 [SMILES: CNc1c(-c2cccc(OCc3cccnc3)c2)nc2cc(C#N)ccn12] | 3-(methylamino)-2-[3-(pyridin-3-ylmethoxy)phenyl]imidazo[1,2-a]pyridine-7-carbonitrile | +++ |

-continued

RBA IC$_{50}$ activity summary: <100 nM +++, 100-500 nM ++, >500 nM +

| Structure | IUPAC Name | Activity |
|---|---|---|
| 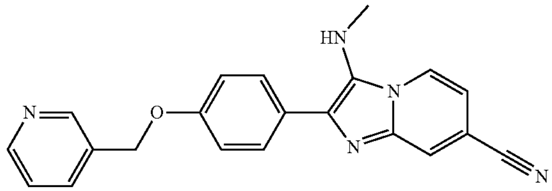 [SMILES: CNc1c(-c2ccc(OCc3cccnc3)cc2)nc2cc(C#N)ccn12] | 3-(methylamino)-2-[4-(pyridin-3-ylmethoxy)phenyl]imidazo[1,2-a]pyridine-7-carbonitrile | +++ |
| 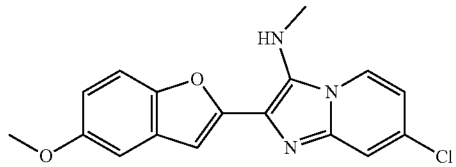 [SMILES: CNc1c(-c2cc3cc(OC)ccc3o2)nc2cc(Cl)ccn12] | 7-chloro-2-(5-methoxy-1-benzofuran-2-yl)-N-methylimidazo[1,2-a]pyridin-3-amine | +++ |
| 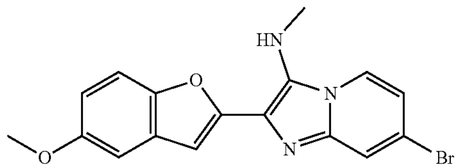 [SMILES: CNc1c(-c2cc3cc(OC)ccc3o2)nc2cc(Br)ccn12] | 7-bromo-2-(5-methoxy-1-benzofuran-2-yl)-N-methylimidazo[1,2-a]pyridin-3-amine | +++ |
| 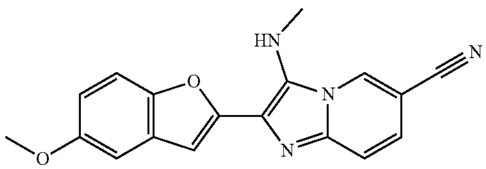 [SMILES: CNc1c(-c2cc3cc(OC)ccc3o2)nc2ccc(C#N)cn12] | 2-(5-methoxy-1-benzofuran-2-yl)-3-(methylamino)imidazo[1,2-a]pyridine-6-carbonitrile | +++ |
| 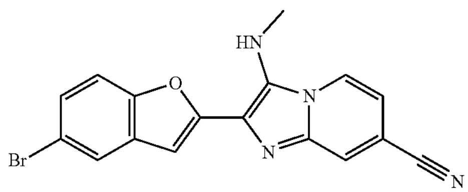 [SMILES: CNc1c(-c2cc3cc(Br)ccc3o2)nc2cc(C#N)ccn12] | 2-(5-bromo-1-benzofuran-2-yl)-3-(methylamino)imidazo[1,2-a]pyridine-7-carbonitrile | +++ |
| 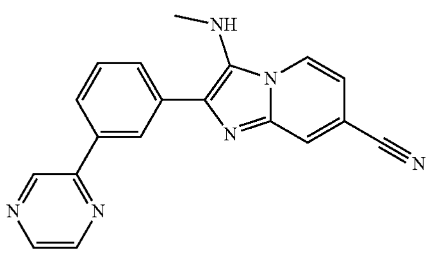 [SMILES: CNc1c(-c2cccc(-c3cnccn3)c2)nc2cc(C#N)ccn12] | 3-(methylamino)-2-[3-(pyrazin-2-yl)phenyl]imidazo[1,2-a]pyridine-7-carbonitrile | +++ |
| 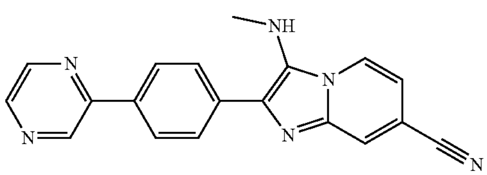 [SMILES: CNc1c(-c2ccc(-c3cnccn3)cc2)nc2cc(C#N)ccn12] | 3-(methylamino)-2-[4-(pyrazin-2-yl)phenyl]imidazo[1,2-a]pyridine-7-carbonitrile | +++ |
| 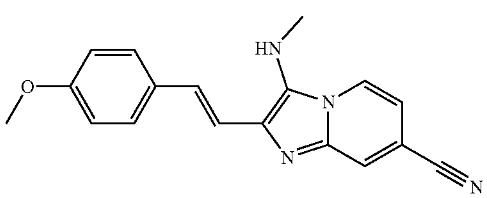 [SMILES: CNc1c(/C=C/c2ccc(OC)cc2)nc2cc(C#N)ccn12] | 2-[(E)-2-(4-methoxyphenyl)ethenyl]-3-(methylamino)imidazo[1,2-a]pyridine-7-carbonitrile | +++ |

-continued

| RBA IC$_{50}$ activity summary: <100 nM +++, 100-500 nM ++, >500 nM + | | |
|---|---|---|
| Structure | IUPAC Name | Activity |
| | 2-(5-methoxy-1-benzofuran-2-yl)-3-[(2-methoxyethyl)amino]imidazo[1,2-a]pyridine-7-carbonitrile | +++ |
| | 2-(2,3-dihydro-1,4-benzodioxin-6-yl)-3-(methylamino)imidazo[1,2-a]pyridine-7-carbonitrile | ++ |
| | 2-(5-bromofuran-2-yl)-3-(methylamino)imidazo[1,2-a]pyridine-7-carbonitrile | ++ |
| | 2-(4-cyanophenyl)-3-(methylamino)imidazo[1,2-a]pyridine-7-carbonitrile | +++ |
| | 2-(1-benzofuran-5-yl)-3-(methylamino)imidazo[1,2-a]pyridine-7-carbonitrile | ++ |
| | 3-(methylamino)-2-[4-(prop-2-yn-1-yloxy)phenyl]imidazo[1,2-a]pyridine-7-carbonitrile | ++ |
| | 2-(5-fluoro-1-benzofuran-2-yl)-3-(methylamino)imidazo[1,2-a]pyridine-7-carbonitrile | +++ |

-continued

| Structure | IUPAC Name | Activity |
|---|---|---|
| 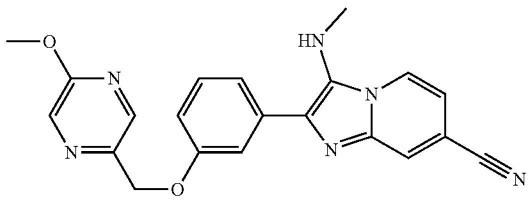 [SMILES: CNc1c(-c2cccc(OCc3cnc(OC)cn3)c2)nc2cc(C#N)ccn12] | 2-{3-[(5-methoxypyrazin-2-yl)methoxy]phenyl}-3-(methylamino)imidazo[1,2-a]pyridine-7-carbonitrile | +++ |
| 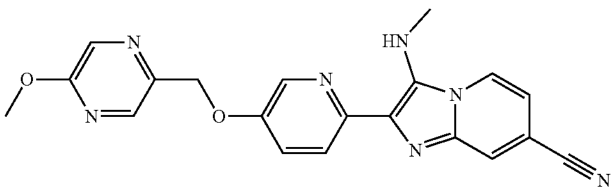 [SMILES: CNc1c(-c2ccc(OCc3cnc(OC)cn3)cn2)nc2cc(C#N)ccn12] | 2-{5-[(5-methoxypyrazin-2-yl)methoxy]pyridin-2-yl}-3-(methylamino)imidazo[1,2-a]pyridine-7-carbonitrile | +++ |
| 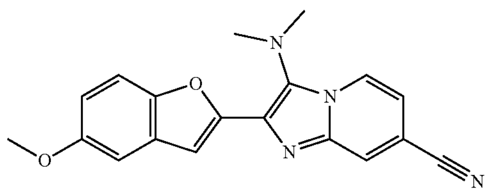 [SMILES: COc1ccc2oc(-c3nc4cc(C#N)ccn4c3N(C)C)cc2c1] | 3-(dimethylamino)-2-(5-methoxy-1-benzofuran-2-yl)imidazo[1,2-a]pyridine-7-carbonitrile | ++ |
| 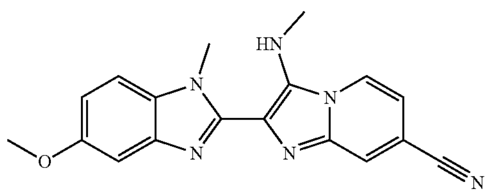 [SMILES: CNc1c(-c2nc3cc(OC)ccc3n2C)nc2cc(C#N)ccn12] | 2-(5-methoxy-1-methyl-1H-1,3-benzodiazol-2-yl)-3-(methylamino)imidazo[1,2-a]pyridine-7-carbonitrile | +++ |
| 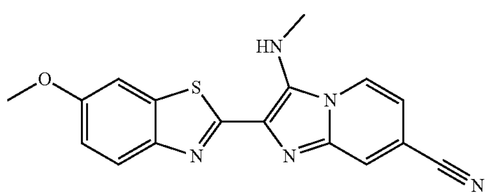 [SMILES: CNc1c(-c2nc3ccc(OC)cc3s2)nc2cc(C#N)ccn12] | 2-(6-methoxy-1,3-benzothiazol-2-yl)-3-(methylamino)imidazo[1,2-a]pyridine-7-carbonitrile | +++ |
| 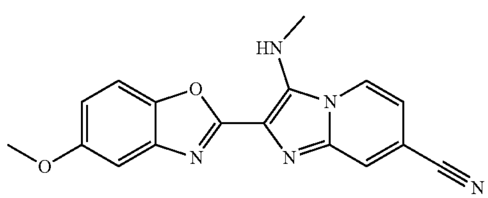 [SMILES: CNc1c(-c2nc3cc(OC)ccc3o2)nc2cc(C#N)ccn12] | 2-(5-methoxy-1,3-benzoxazol-2-yl)-3-(methylamino)imidazo[1,2-a]pyridine-7-carbonitrile | +++ |
| 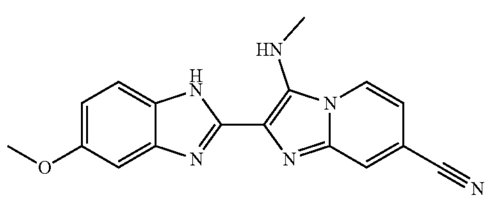 [SMILES: CNc1c(-c2nc3cc(OC)ccc3[nH]2)nc2cc(C#N)ccn12] | 2-(5-methoxy-1H-1,3-benzodiazol-2-yl)-3-(methylamino)imidazo[1,2-a]pyridine-7-carbonitrile | +++ |
| 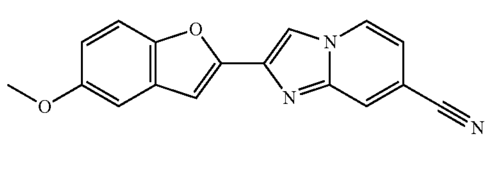 [SMILES: COc1ccc2oc(-c3cn4ccc(C#N)cc4n3)cc2c1] | 2-(5-methoxy-1-benzofuran-2-yl)imidazo[1,2-a]pyridine-7-carbonitrile | +++ |

RBA IC$_{50}$ activity summary: <100 nM +++, 100-500 nM ++, >500 nM +

-continued

| RBA IC$_{50}$ activity summary: <100 nM +++, 100-500 nM ++, >500 nM + | | |
|---|---|---|
| Structure | IUPAC Name | Activity |
| | 2-(6-methoxy-1-methyl-1H-1,3-benzodiazol-2-yl)-3-(methylamino)imidazo[1,2-a]pyridine-7-carbonitrile | +++ |
| | 3-(methylamino)-2-[5-(pyridin-3-ylmethoxy)-1-benzofuran-2-yl]imidazo[1,2-a]pyridine-7-carbonitrile | +++ |
| | 3-amino-2-[5-(2-fluoroethoxy)-1-benzofuran-2-yl]imidazo[1,2-a]pyridine-7-carbonitrile | +++ |
| | 3-amino-2-(5-methoxy-1-benzofuran-2-yl)imidazo[1,2-a]pyridine-7-carbonitrile | +++ |
| | 2-(5-methoxy-1-benzofuran-2-yl)-3-(methoxymethyl)imidazo[1,2-a]pyridine-7-carbonitrile | +++ |
| | 3-[(dimethylamino)methyl]-2-(5-methoxy-1-benzofuran-2-yl)imidazo[1,2-a]pyridine-7-carbonitrile | ++ |
| | 2-{5-[2-(dimethylamino)ethoxy]-1-benzofuran-2-yl}-3-(methylamino)imidazo[1,2-a]pyridine-7-carbonitrile | ++ |

-continued

RBA IC$_{50}$ activity summary: <100 nM +++, 100-500 nM ++, >500 nM +

| Structure | IUPAC Name | Activity |
|---|---|---|
| 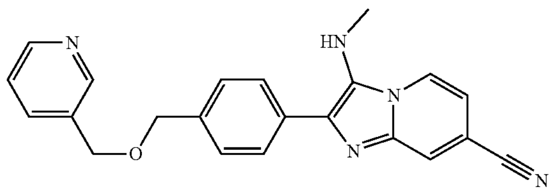 [SMILES: CNc1c(-c2ccc(COCc3cccnc3)cc2)nc2cc(C#N)ccn12] | 3-(methylamino)-2-{4-[(pyridin-3-ylmethoxy)methyl]phenyl}imidazo[1,2-a]pyridine-7-carbonitrile | ++ |
| 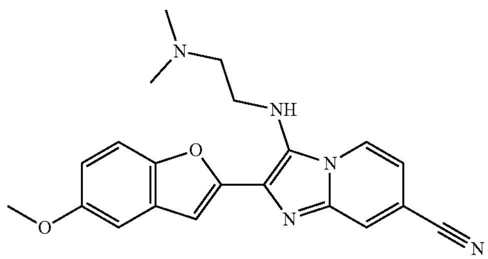 [SMILES: COc1ccc2oc(-c3nc4cc(C#N)ccn4c3NCCN(C)C)cc2c1] | 3-{[2-(dimethylamino)ethyl]amino}-2-(5-methoxy-1-benzofuran-2-yl)imidazo[1,2-a]pyridine-7-carbonitrile | ++ |
| 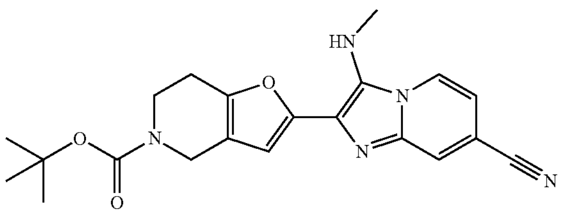 [SMILES: CNc1c(-c2cc3c(o2)CCN(C(=O)OC(C)(C)C)C3)nc2cc(C#N)ccn12] | tert-butyl 2-[7-cyano-3-(methylamino)imidazo[1,2-a]pyridin-2-yl]-4H,5H,6H,7H-furo[3,2-c]pyridine-5-carboxylate | ++ |
| 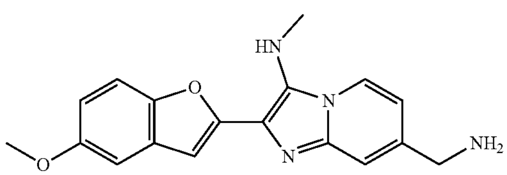 [SMILES: CNc1c(-c2cc3cc(OC)ccc3o2)nc2cc(CN)ccn12] | 7-(aminomethyl)-2-(5-methoxy-1-benzofuran-2-yl)-N-methylimidazo[1,2-a]pyridin-3-amine | ++ |
| 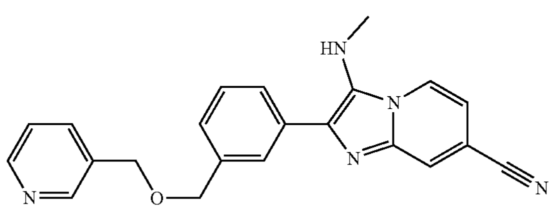 [SMILES: CNc1c(-c2cccc(COCc3cccnc3)c2)nc2cc(C#N)ccn12] | 3-(methylamino)-2-{3-[(pyridin-3-ylmethoxy)methyl]phenyl}imidazo[1,2-a]pyridine-7-carbonitrile | ++ |
| 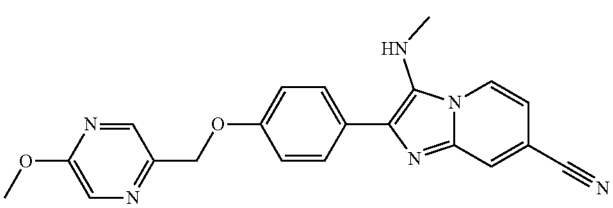 [SMILES: CNc1c(-c2ccc(OCc3cnc(OC)cn3)cc2)nc2cc(C#N)ccn12] | 2-{4-[(5-methoxypyrazin-2-yl)methoxy]phenyl}-3-(methylamino)imidazo[1,2-a]pyridine-7-carbonitrile | +++ |
| 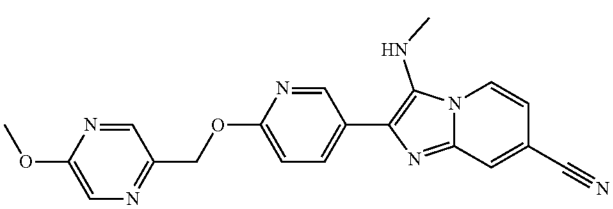 [SMILES: CNc1c(-c2ccc(OCc3cnc(OC)cn3)nc2)nc2cc(C#N)ccn12] | 2-{6-[(5-methoxypyrazin-2-yl)methoxy]pyridin-3-yl}-3-(methylamino)imidazo[1,2-a]pyridine-7-carbonitrile | +++ |

-continued

| Structure | IUPAC Name | Activity |
|---|---|---|
| 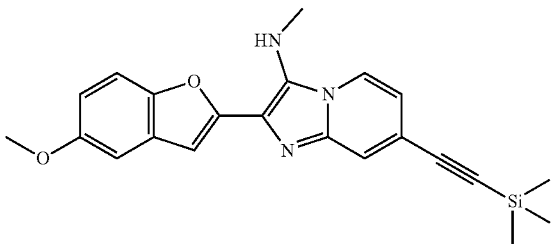 | 2-(5-methoxy-1-benzofuran-2-yl)-N-methyl-7-[2-(trimethylsilyl)ethynyl]imidazo[1,2-a]pyridin-3-amine | +++ |
| 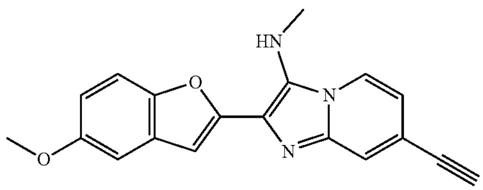 [SMILES: C#Cc1ccn2c(NC)c(-c3cc4cc(OC)ccc4o3)nc2c1] | 7-ethynyl-2-(5-methoxy-1-benzofuran-2-yl)-N-methylimidazo[1,2-a]pyridin-3-amine | +++ |
| 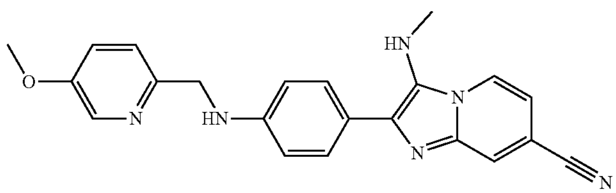 [SMILES: CNc1c(-c2ccc(NCc3ccc(OC)cn3)cc2)nc2cc(C#N)ccn12] | 2-(4-{[(5-methoxypyridin-2-yl)methyl]amino}phenyl)-3-(methylamino)imidazo[1,2-a]pyridine-7-carbonitrile | +++ |
| 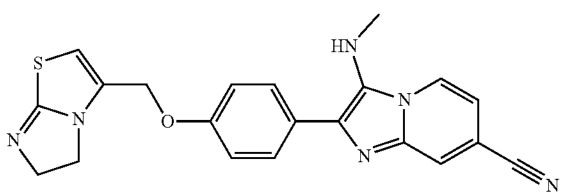 [SMILES: CNc1c(-c2ccc(OCC3=CSC4=NCCN34)cc2)nc2cc(C#N)ccn12] | 2-(4-{5H,6H-imidazo[2,1-b][1,3]thiazol-3-ylmethoxy}phenyl)-3-(methylamino)imidazo[1,2-a]pyridine-7-carbonitrile | +++ |
| 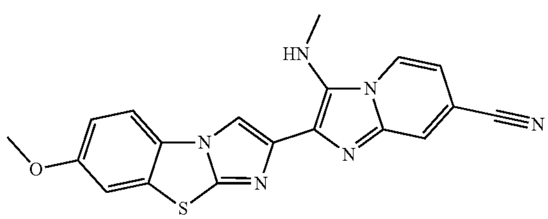 [SMILES: CNc1c(-c2cn3c(n2)sc2cc(OC)ccc23)nc2cc(C#N)ccn12] | 2-{10-methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile | +++ |
| 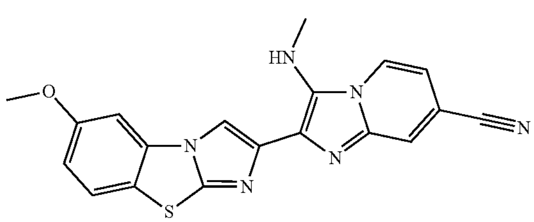 [SMILES: CNc1c(-c2cn3c(n2)sc2ccc(OC)cc23)nc2cc(C#N)ccn12] | 2-{11-methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile | +++ |
| 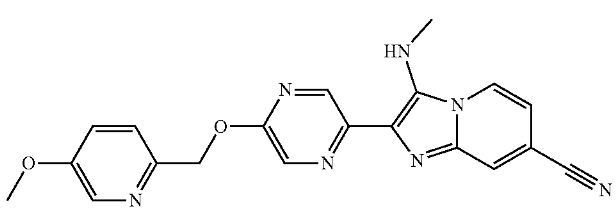 [SMILES: CNc1c(-c2cnc(OCc3ccc(OC)cn3)cn2)nc2cc(C#N)ccn12] | 2-{5-[(5-methoxypyridin-2-yl)methoxy]pyrazin-2-yl}-3-(methylamino)imidazo[1,2-a]pyridine-7-carbonitrile | +++ |

RBA IC$_{50}$ activity summary: <100 nM +++, 100-500 nM ++, >500 nM +

Various modifications, additions, substitutions, and variations to the illustrative examples set forth herein will be apparent to those skilled in the art from the foregoing description. Such modifications are also intended to fall within the scope of the appended claims.

What is claimed is:
1. A compound of Formula I,

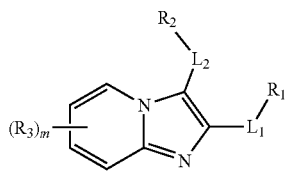

(I)

or a pharmaceutically acceptable salt thereof, wherein
$L_1$ is —CH=CH— or $L_1$ is absent;
$R_1$ is chosen from 5-(tert-butoxycarbonyl)-4,5,6,7-tetrahydrofuro[3,2-c]pyridin-2-yl, 2,3-dihydro-1,4,-benzodioxin-6-yl, 5-bromofuran-2-yl, 1-benzofuran-5-yl, 11-methoxy-7-thia-2,5-diazatricyclo[6.4.0.0$^{2,6}$]dodeca-1(12),3,5,8,10-pentaen-4-yl, and 10-methoxy-7-thia-2,5-diazatricyclo[6.4.0.0$^{2,6}$]dodeca-1(12),3,5,8,10-pentaen-4-yl;
$L_2$ is —N($R_4$)—;
$R_2$ is chosen from
  hydrogen,
  lower alkyl, and
  lower alkyl substituted with lower alkoxy, amino, (alkyl)amino, (dialkyl)amino, or hydroxy;
for each occurrence, $R_3$ is independently chosen from
  halo,
  cyano,
  lower alkyl optionally substituted with amino, (alkyl)amino, or di(alkyl)amino, and
  ethynyl optionally substituted with tri(alkyl)silyl;
$R_4$ is chosen from hydrogen and lower alkyl; and
m is 0, 1, or 2.
2. The compound of claim 1, wherein $L_1$ is absent.
3. The compound of claim 1, wherein $L_1$ is —CH=CH—.
4. The compound of claim 1, wherein $R_4$ is hydrogen or methyl.
5. The compound of claim 4, wherein $R_2$ is chosen from hydrogen, lower alkyl and lower alkyl substituted with hydroxy, lower alkoxy, amino, (alkyl)amino or (dialkyl)amino.
6. The compound of claim 1, wherein m is 1.
7. The compound of claim 6, wherein $R_3$ is chosen from bromo, chloro, fluoro, aminomethyl, 2-(trimethylsilyl)ethynyl, ethynyl, and cyano.
8. The compound of claim 1, wherein m is 0.
9. A compound, or a pharmaceutically acceptable salt thereof, chosen from:
2-(5-fluoro-1-benzofuran-2-yl)-N-methylimidazo[1,2-a]pyridin-3-amine;
2-(5-methoxy-1-benzofuran-2-yl)-N-methylimidazo[1,2-a]pyridin-3-amine;
6-fluoro-2-(5-methoxy-1-benzofuran-2-yl)-N-methylimidazo[1,2-a]pyridin-3-amine;
7-fluoro-2-(5-methoxy-1-benzofuran-2-yl)-N-methylimidazo[1,2-a]pyridin-3-amine;
2-(5-methoxy-1-benzofuran-2-yl)-3-(methylamino)imidazo[1,2-c]pyridine-7-carbonitrile;
2-[6-fluoro-3-(methylamino)imidazo[1,2-c]pyridin-2-yl]-1-benzofuran-5-ol;
2-(5-methoxy-1-benzofuran-2-yl)-N-(2-methoxyethyl)imidazo[1,2-c]pyridin-3-amine;
2-[7-fluoro-3-(methylamino)imidazo[1,2-c]pyridin-2-yl]-1-benzofuran-5-ol;
2-{3-[(2-hydroxyethyl)amino]imidazo[1,2-c]pyridin-2-yl}-1-benzofuran-5-ol;
2-(5-hydroxy-1-benzofuran-2-yl)-3-(methylamino)imidazo[1,2-c]pyridine-7-carbonitrile;
2-[5-(2-fluoroethoxy)-1-benzofuran-2-yl]-3-(methylamino)imidazo[1,2-c]pyridine-7-carbonitrile;
2-(4-methoxyphenyl)-3-(methylamino)imidazo[1,2-c]pyridine-7-carbonitrile;
2-(6-methoxy-1-benzofuran-2-yl)-3-(methylamino)imidazo[1,2-c]pyridine-7-carbonitrile;
7-methoxy-2-(5-methoxy-1-benzofuran-2-yl)-N-methylimidazo[1,2-c]pyridin-3-amine;
3-(methylamino)-2-[3-(pyridin-3-ylmethoxy)phenyl]imidazo[1,2-c]pyridine-7-carbonitrile;
3-(methylamino)-2-[4-(pyridin-3-ylmethoxy)phenyl]imidazo[1,2-c]pyridine-7-carbonitrile;
7-chloro-2-(5-methoxy-1-benzofuran-2-yl)-N-methylimidazo[1,2-c]pyridin-3-amine;
7-bromo-2-(5-methoxy-1-benzofuran-2-yl)-N-methylimidazo[1,2-c]pyridin-3-amine;
2-(5-methoxy-1-benzofuran-2-yl)-3-(methylamino)imidazo[1,2-c]pyridine-6-carbonitrile;
2-(5-bromo-1-benzofuran-2-yl)-3-(methylamino)imidazo[1,2-c]pyridine-7-carbonitrile;
3-(methylamino)-2-[3-(pyrazin-2-yl)phenyl]imidazo[1,2-c]pyridine-7-carbonitrile;
3-(methylamino)-2-[4-(pyrazin-2-yl)phenyl]imidazo[1,2-c]pyridine-7-carbonitrile;
2-[(E)-2-(4-methoxyphenyl)ethenyl]-3-(methylamino)imidazo[1,2-c]pyridine-7-carbonitrile;
2-(5-methoxy-1-benzofuran-2-yl)-3-[(2-methoxyethyl)amino]imidazo[1,2-c]pyridine-7-carbonitrile;
2-(2,3-dihydro-1,4-benzodioxin-6-yl)-3-(methylamino)imidazo[1,2-c]pyridine-7-carbonitrile;
2-(5-bromofuran-2-yl)-3-(methylamino)imidazo[1,2-c]pyridine-7-carbonitrile;
2-(4-cyanophenyl)-3-(methylamino)imidazo[1,2-c]pyridine-7-carbonitrile;
2-(1-benzofuran-5-yl)-3-(methylamino)imidazo[1,2-c]pyridine-7-carbonitrile;
3-(methylamino)-2-[4-(prop-2-yn-1-yloxy)phenyl]imidazo[1,2-c]pyridine-7-carbonitrile;
2-(5-fluoro-1-benzofuran-2-yl)-3-(methylamino)imidazo[1,2-c]pyridine-7-carbonitrile;
2-{3-[(5-methoxypyrazin-2-yl)methoxy]phenyl}-3-(methylamino)imidazo[1,2-c]pyridine-7-carbonitrile;
2-{5-[(5-methoxypyrazin-2-yl)methoxy]pyridin-2-yl}-3-(methylamino)imidazo[1,2-a]pyridine-7-carbonitrile;
3-(dimethylamino)-2-(5-methoxy-1-benzofuran-2-yl)imidazo[1,2-c]pyridine-7-carbonitrile;
2-(5-methoxy-1-methyl-1H-1,3-benzodiazol-2-yl)-3-(methylamino)imidazo[1,2-c]pyridine-7-carbonitrile;
2-(6-methoxy-1,3-benzothiazol-2-yl)-3-(methylamino)imidazo[1,2-c]pyridine-7-carbonitrile;
2-(5-methoxy-1,3-benzoxazol-2-yl)-3-(methylamino)imidazo[1,2-c]pyridine-7-carbonitrile;
2-(5-methoxy-1H-1,3-benzodiazol-2-yl)-3-(methylamino)imidazo[1,2-a]pyridine-7-carbonitrile;
2-(5-methoxy-1-benzofuran-2-yl)imidazo[1,2-a]pyridine-7-carbonitrile;

2-(6-methoxy-1-methyl-1H-1,3-benzodiazol-2-yl)-3-(methylamino)imidazo[1,2-c]pyridine-7-carbonitrile;
3-(methylamino)-2-[5-(pyridin-3-ylmethoxy)-1-benzofuran-2-yl]imidazo[1,2-c]pyridine-7-carbonitrile;
3-amino-2-[5-(2-fluoroethoxy)-1-benzofuran-2-yl]imidazo[1,2-c]pyridine-7-carbonitrile;
3-amino-2-(5-methoxy-1-benzofuran-2-yl)imidazo[1,2-c]pyridine-7-carbonitrile;
2-(5-methoxy-1-benzofuran-2-yl)-3-(methoxymethyl)imidazo[1,2-c]pyridine-7-carbonitrile;
3-[(dimethylamino)methyl]-2-(5-methoxy-1-benzofuran-2-yl)imidazo[1,2-c]pyridine-7-carbonitrile;
2-{5-[2-(dimethylamino)ethoxy]-1-benzofuran-2-yl}-3-(methylamino)imidazo[1,2-c]pyridine-7-carbonitrile;
3-(methylamino)-2-{4-[(pyridin-3-ylmethoxy)methyl]phenyl}imidazo[1,2-a]pyridine-7-carbonitrile;
3-{[2-(dimethylamino)ethyl]amino}-2-(5-methoxy-1-benzofuran-2-yl)imidazo[1,2-c]pyridine-7-carbonitrile
tert-butyl 2-[7-cyano-3-(methylamino)imidazo[1,2-c]pyridin-2-yl]-4H,5H,6H,7H-furo[3,2-c]pyridine-5-carboxylate;
7-(aminomethyl)-2-(5-methoxy-1-benzofuran-2-yl)-N-methylimidazo[1,2-c]pyridin-3-amine;
3-(methylamino)-2-{3-[(pyridin-3-ylmethoxy)methyl]phenyl}imidazo[1,2-a]pyridine-7-carbonitrile;
2-{4-[(5-methoxypyrazin-2-yl)methoxy]phenyl}-3-(methylamino)imidazo[1,2-c]pyridine-7-carbonitrile;
2-{6-[(5-methoxypyrazin-2-yl)methoxy]pyridin-3-yl}-3-(methylamino)imidazo[1,2-c]pyridine-7-carbonitrile;
2-(5-methoxy-1-benzofuran-2-yl)-N-methyl-7-[2-(trimethylsilyl)ethynyl]imidazo[1,2-c]pyridin-3-amine;
7-ethynyl-2-(5-methoxy-1-benzofuran-2-yl)-N-methylimidazo[1,2-c]pyridin-3-amine;
2-(4-{[(5-methoxypyridin-2-yl)methyl]amino}phenyl)-3-(methylamino)imidazo[1,2-a]pyridine-7-carbonitrile;
2-(4-{5H,6H-imidazo[2,1-b][1,3]thiazol-3-ylmethoxy}phenyl)-3-(methylamino)imidazo[1,2-c]pyridine-7-carbonitrile;
2-{10-methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile;
2-{11-methoxy-7-thia-2,5-diazatricyclo[6.4.0.0$^{2,6}$]dodeca-1(12),3,5,8,10-pentaen-4-yl}-3-(methylamino)imidazo[1,2-a]pyridine-7-carbonitrile; and
2-{5-[(5-methoxypyridin-2-yl)methoxy]pyrazin-2-yl}-3-(methylamino)imidazo[1,2-a]pyridine-7-carbonitrile.

\* \* \* \* \*